(12) United States Patent
Kehrel et al.

(10) Patent No.: US 8,034,769 B2
(45) Date of Patent: *Oct. 11, 2011

(54) OXIDIZED PROTEINS AND OXIDIZED PROTEIN INHIBITOR COMPOSITIONS AND METHODS OF USE THEREOF

(75) Inventors: Beate Kehrel, Muenster (DE); Martin Brodde, Muenster (DE)

(73) Assignee: Hamburger Stiftung zur Foerderung Von Wissenschaft und Kultur, Hamburg (DE)

( * ) Notice: Subject to any disclaimer, the term of this patent is extended or adjusted under 35 U.S.C. 154(b) by 1564 days.

This patent is subject to a terminal disclaimer.

(21) Appl. No.: 10/399,824

(22) PCT Filed: Oct. 19, 2001

(86) PCT No.: PCT/EP01/12129
§ 371 (c)(1),
(2), (4) Date: Sep. 4, 2003

(87) PCT Pub. No.: WO02/32445
PCT Pub. Date: Apr. 25, 2002

(65) Prior Publication Data
US 2004/0047861 A1    Mar. 11, 2004

(30) Foreign Application Priority Data
Oct. 20, 2001 (DE) .................................. 101 48 624

(51) Int. Cl.
A61K 38/02    (2006.01)
A61K 38/17    (2006.01)
A61K 38/36    (2006.01)
A61K 38/38    (2006.01)

(52) U.S. Cl. ........ 514/3.8; 514/13.3; 514/13.7; 514/14.9
(58) Field of Classification Search .................. None
See application file for complete search history.

(56) References Cited

U.S. PATENT DOCUMENTS
4,035,483 A * 7/1977 Bunyan .................. 424/665
(Continued)

FOREIGN PATENT DOCUMENTS
WO    91/10684    7/1991
(Continued)

OTHER PUBLICATIONS
CD36 Mediates the In Vitro Inhibitory Effects of Thrombospondin-1 on Endothelial Cells, The Journal of Cell Biology, David W. Dawson, Aug. 11, 1997, vol. 138, No. 2, pp. 707-717.
(Continued)

Primary Examiner — Jeffrey E Russel
(74) Attorney, Agent, or Firm — Novak Druce + Quigg LLP

(57) ABSTRACT

The invention relates to substances which inhibit the binding of oxidized proteins to CD36 or inhibit the functions of CD36 that are induced by the interaction of CD36 with oxidized proteins. The invention also relates to the use of these substances as medicaments for humans and animals. In one embodiment, a medicament includes an oxidized protein, an oxidized peptide, or structural analog or mimetic thereof. Methods for prophylaxis or therapy of acute infections, inhibition of angiogenesis, and improvement of hemostasis include administering to an animal or human in need thereof an effective amount of a medicament including an oxidized protein, an oxidized peptide, or structural analog or mimetic thereof. An example of an acute infection is Human Immunodeficiency Virus (HIV).

6 Claims, 40 Drawing Sheets

U.S. PATENT DOCUMENTS

Figure 2:
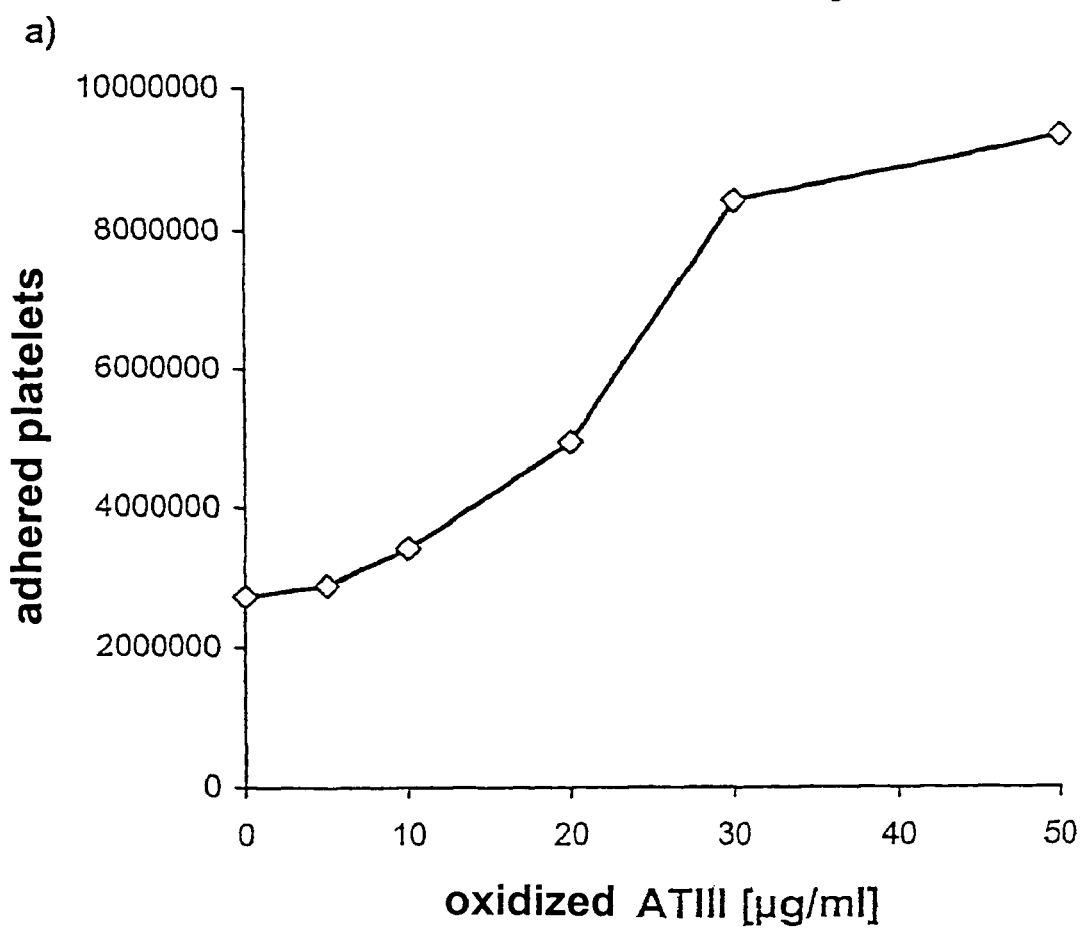

| | | | | |
|---|---|---|---|---|
| 5,045,531 | A * | 9/1991 | Berkowitz et al. | 514/12 |
| 5,366,440 | A * | 11/1994 | Fossel | 604/5.03 |
| 5,552,307 | A * | 9/1996 | Kessler et al. | 435/171 |
| 5,776,912 | A * | 7/1998 | Patel et al. | 514/54 |
| 6,193,953 | B1 * | 2/2001 | Lohrmann et al. | 424/9.52 |
| 6,251,868 | B1 * | 6/2001 | Kubota et al. | 514/19 |
| 6,265,377 | B1 * | 7/2001 | Dasseux et al. | 514/12 |
| 6,270,791 | B1 * | 8/2001 | Van Dyke et al. | 424/443 |
| 6,312,713 | B1 * | 11/2001 | Korol et al. | 424/443 |
| 6,953,666 | B1 * | 10/2005 | Kinkade et al. | 435/7.1 |
| 7,388,075 | B2 * | 6/2008 | Kehrel et al. | 530/350 |

FOREIGN PATENT DOCUMENTS

| | | |
|---|---|---|
| WO | WO 96/16663 A1 * | 6/1996 |
| WO | WO 97/21443 A1 * | 6/1997 |
| WO | 00/28072 | 5/2000 |

OTHER PUBLICATIONS

Lovaststin Reduces Expression of the Combined Adhesion and Scavenger Receptor CD36 in Human Monocytic Cells, Biochemical Pharmacology, Angelika Pietsch, vol. 52, pp. 433-439, 1996.

Oxidized Low-Density Lipoprotein Induces Macrophage Respiratory Burst via its Protein Moiety: A Novel Pathway in Atheregenesis, Biochemical and Biophysical Research Communications, Thao Nguyen-Khoa et al., pp. 804-809, vol. 263, No. 3. Oct. 5, 1999.

Activation of Primary Human Monocytes by the Oxidized Form of a1-Antitrypsin, The Journal of Biological Chemistry, Fabian Moraga et al., vol. 275, No. 11, 2000, pp. 7693-7700.

Identification of a CD36-Related Thrombospondin 1-Binding Domain in HIV-1 Envelope Glycoprotein GP120: Relationship to HIV-1-Specific Inhibitory Factors in Human Saliva, J. Exp. Med., Rene Crombie et al., vol. 187, No. 1, Jan. 5, 1998, pp. 25-35.

Peroxynitrite-Mediated Oxidation of Fibrinogen Inhibits Clot Formation, Federation of European Biochemical Societies, G. Lupidi et al., pp. 236-240, vol. 462, No. 3. Dec. 3, 1999.

Hazell, et al., "Oxidation of Low-Density Lipoprotein with Hypochlorite Causes Transformation of the Lipoprotein", Biochem. J., vol. 290, No. 1, 1993, pp. 165-172.

Nozaki, et al., "Reduced Uptake of Oxidized Low Density Lipoproteins in Monocyte-Derived Macrophages," J. Clin. Invest., vol. 96, No. 4, Oct. 1995, pp. 1859-1865.

Yamaguchi, et al., "PS-Liposome and Ox-LDL Bind to Different Sites of the Immunodominant Domain (#155-183) of CD36," Thrombosis Research, vol. 97, No. 5, 2000. pp. 317-326.

Nakata, et al., "CD36, A Novel Receptor for Oxidized Low-Density Lipoproteins is Highly Expressed," Arterioscler. Thromb. Vasc. Biol., vol. 19, No. 5, 1999, pp. 1333-1339.

Endemann, et al., "CD36 is a Receptor for Oxidized Low Density Lipoprotein," J. Biol. Chem., vol. 268, No. 16, 1999, pp. 11811-11816.

Luc, et al., "Oxidation of Lipoproteins and Atherosclerosis," Am. J. Clin. Nutr., vol. 53, No. 1, pp. 206S-209S, (1991).

Schacter, et al., "Oxidative Modification of Fibrinogen Inhibits Thrombin-Catalyzed Clot Formation," Free Radical Biol. Med., vol. 18, No. 4, 1995, pp. 815-821.

Bergt, et al., "Hypochlorite Modification of High Density Lipoprotein: Effects on Cholesterol Efflux From J774 Macrophages," FEBS LEtt., vol. 452, No. 3, 1999, pp. 295-300.

Carr, et al., "Oxidation of Neutrophil Glutathione and Protein Thiols by Myeloperoxidase-derived Hypochlorous Acid", Biochem. J., vol. 327, 1997, pp. 275-281.

Glutathione, http://en.wikipedia.org/wiki/Glutathione., downloaded 2010.

* cited by examiner

FIG. 1

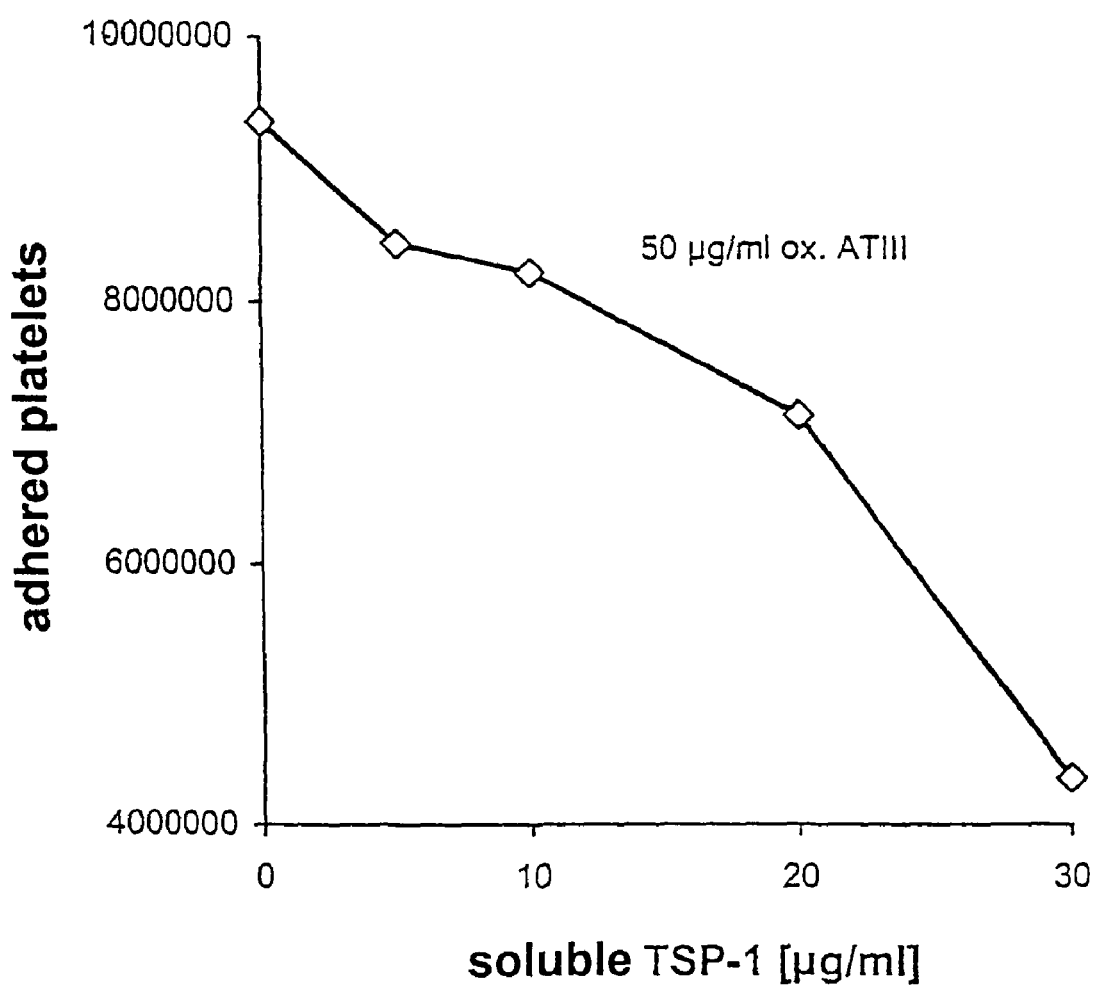

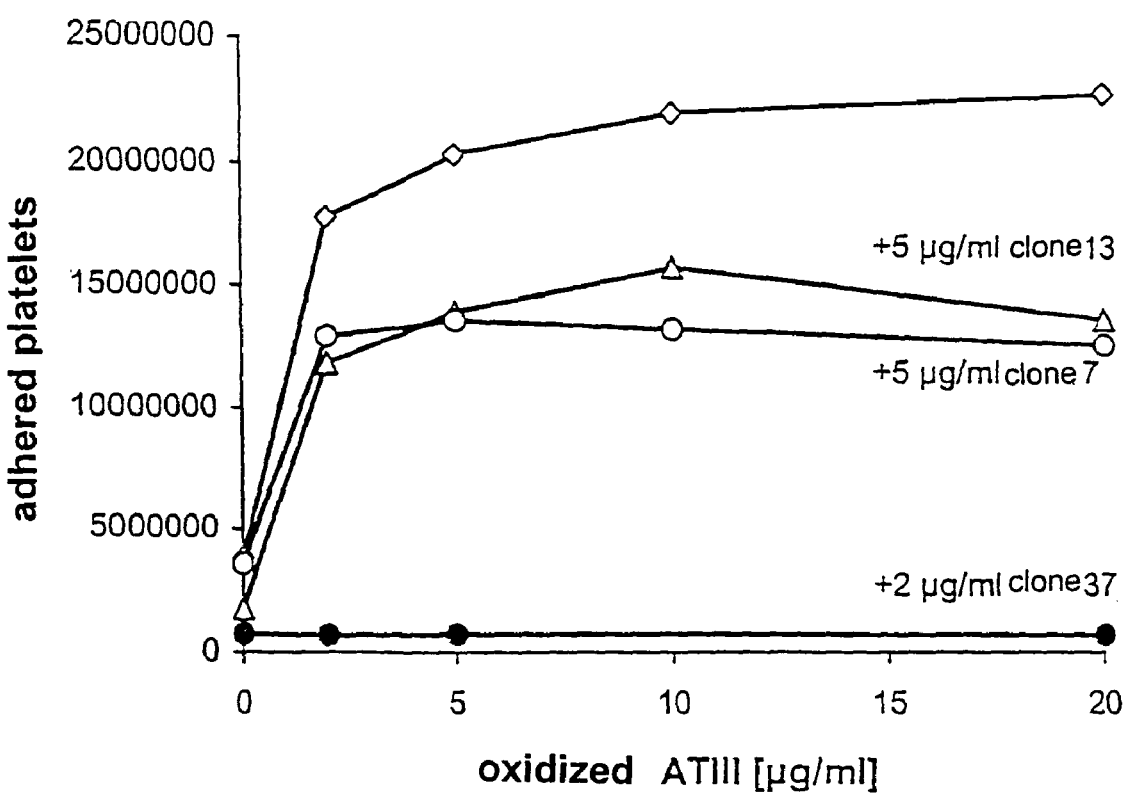

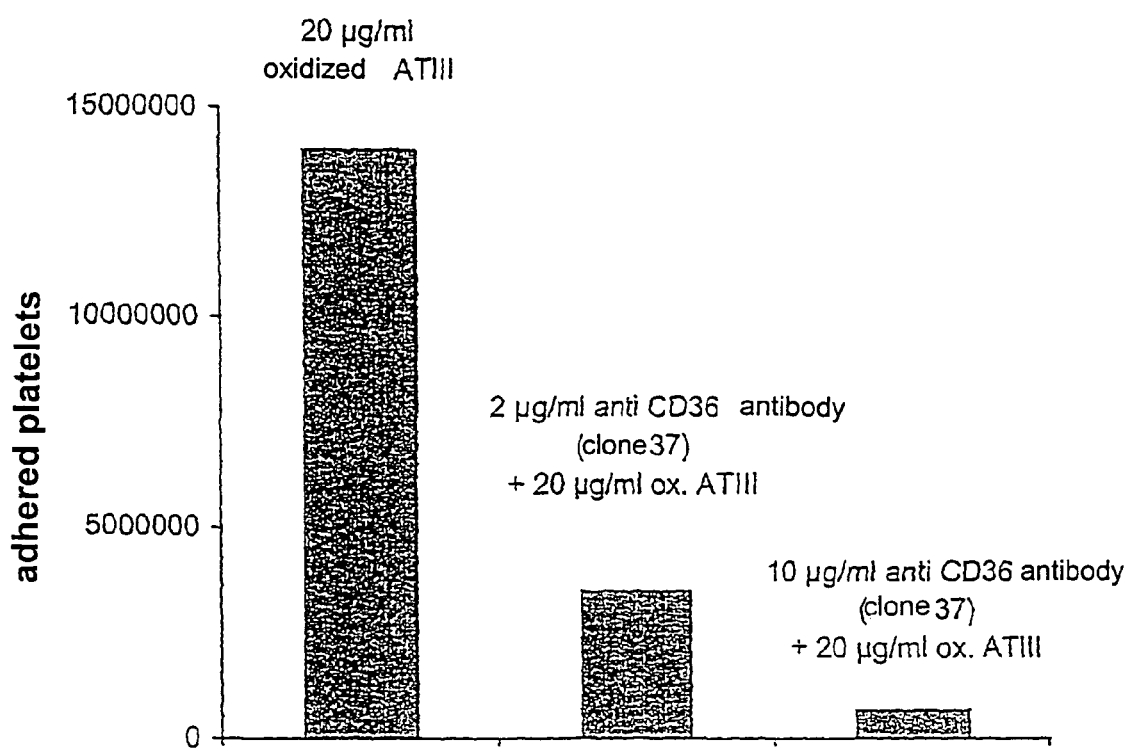

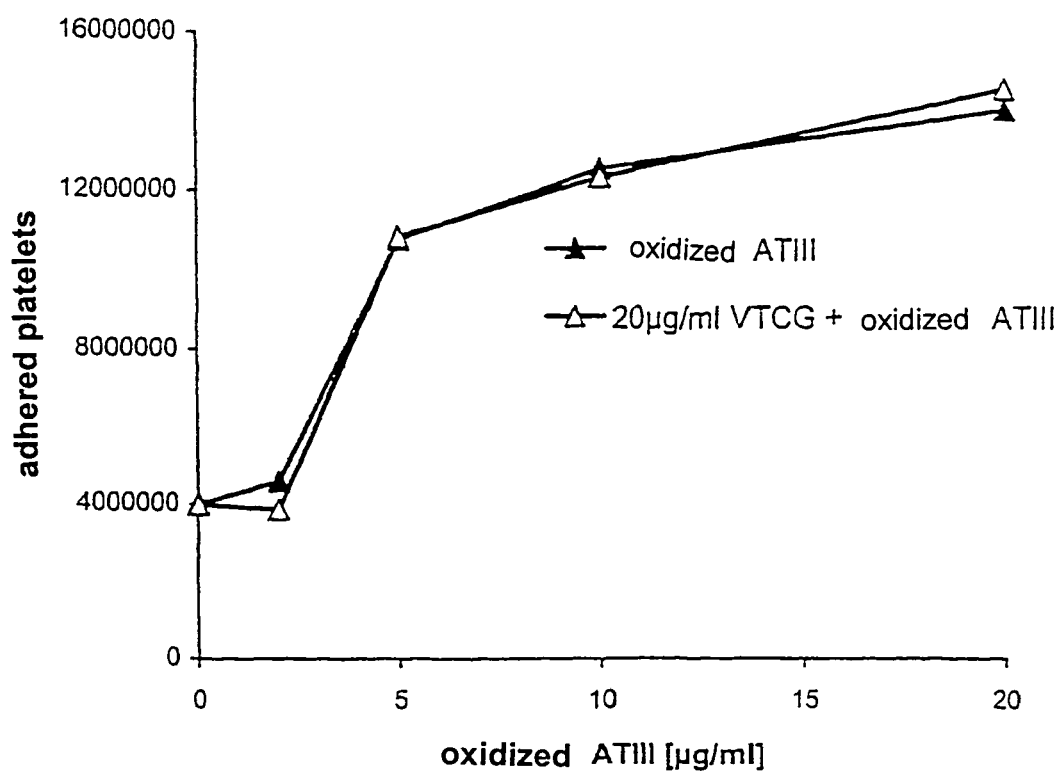

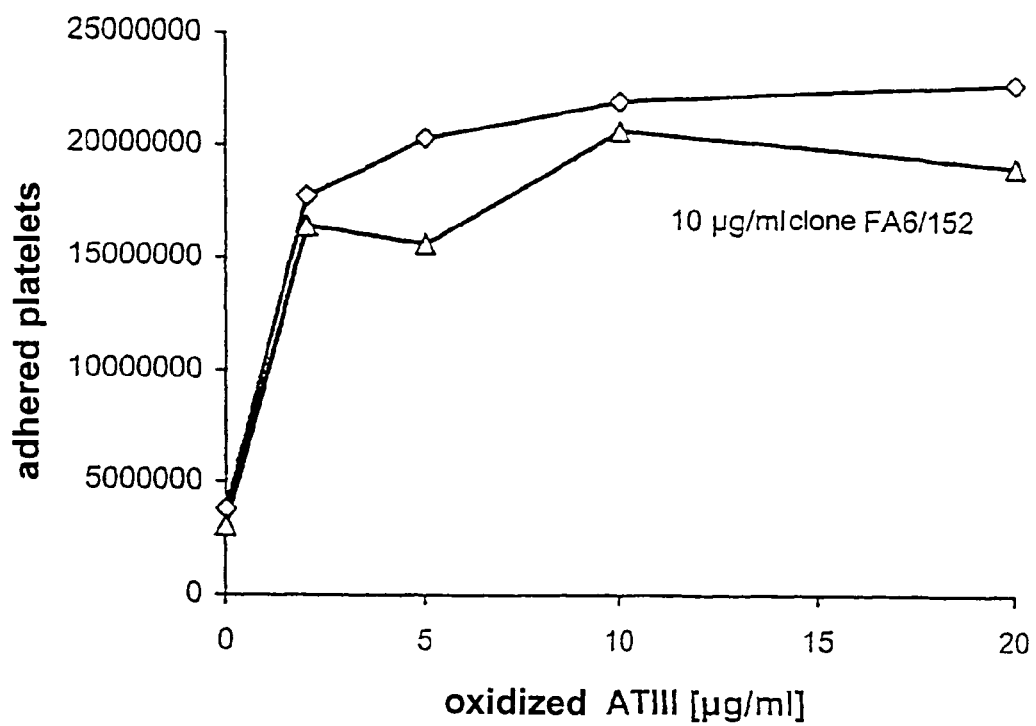

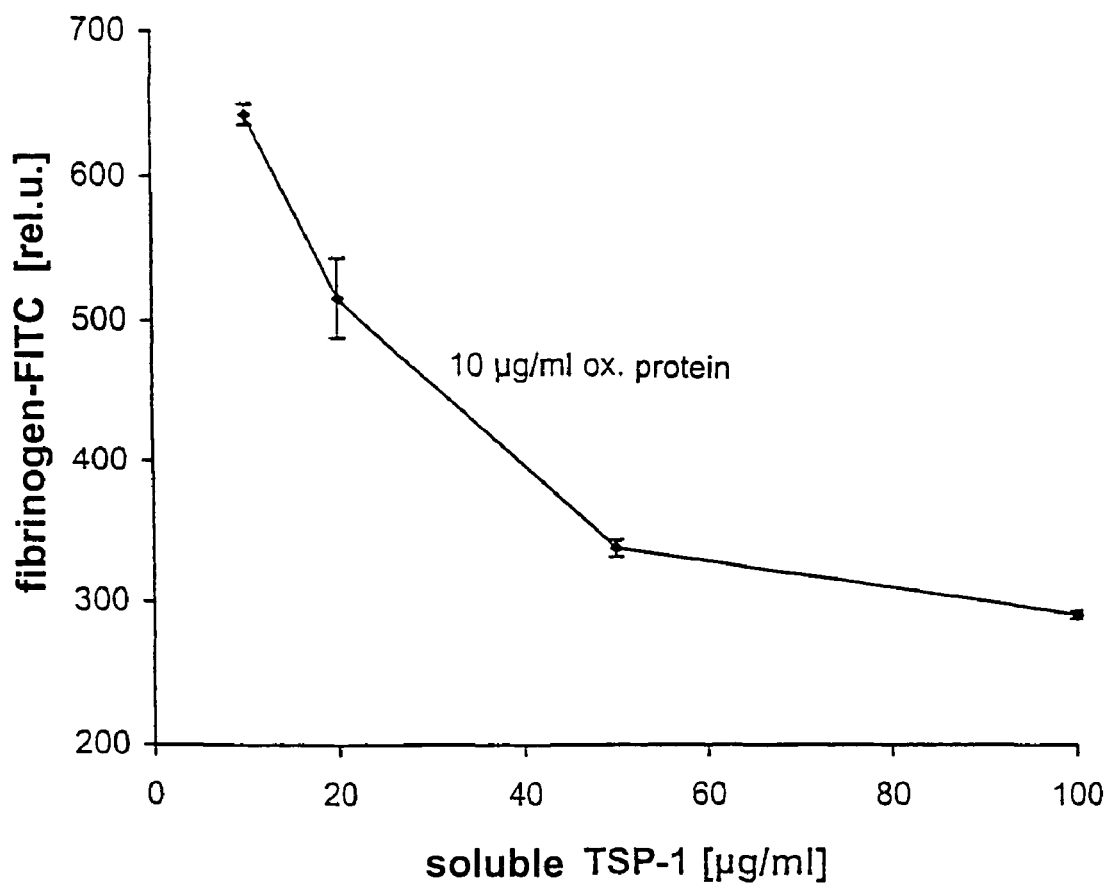

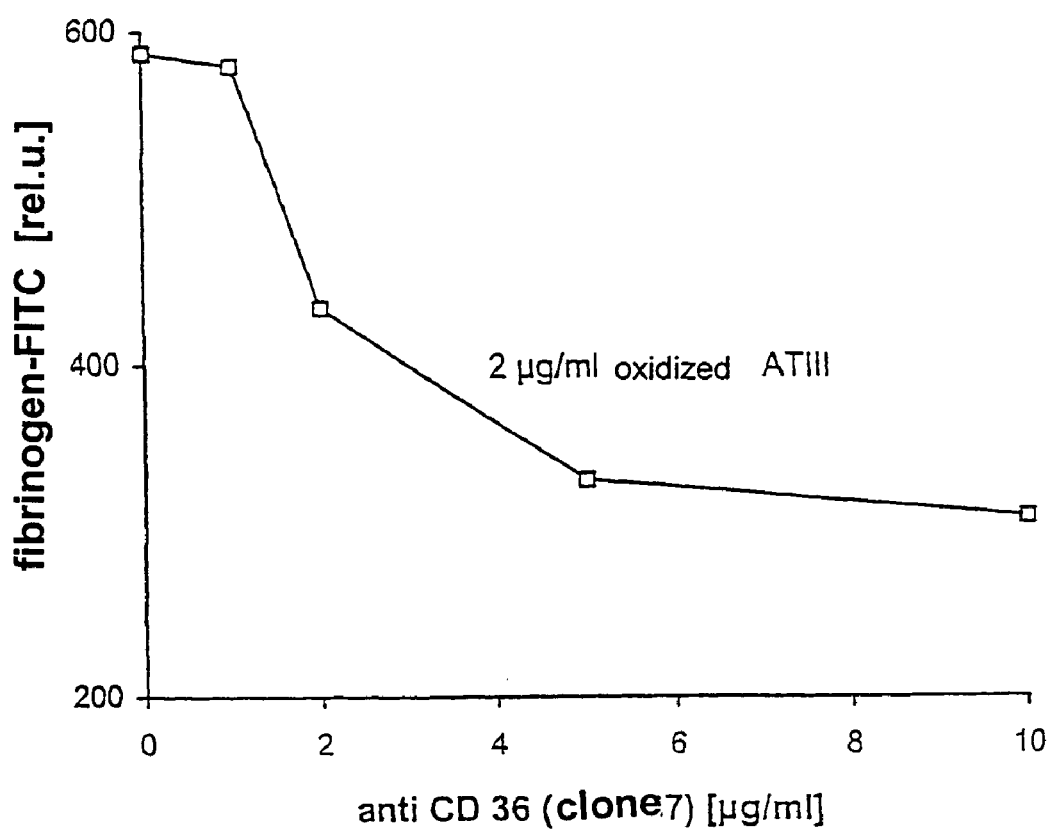

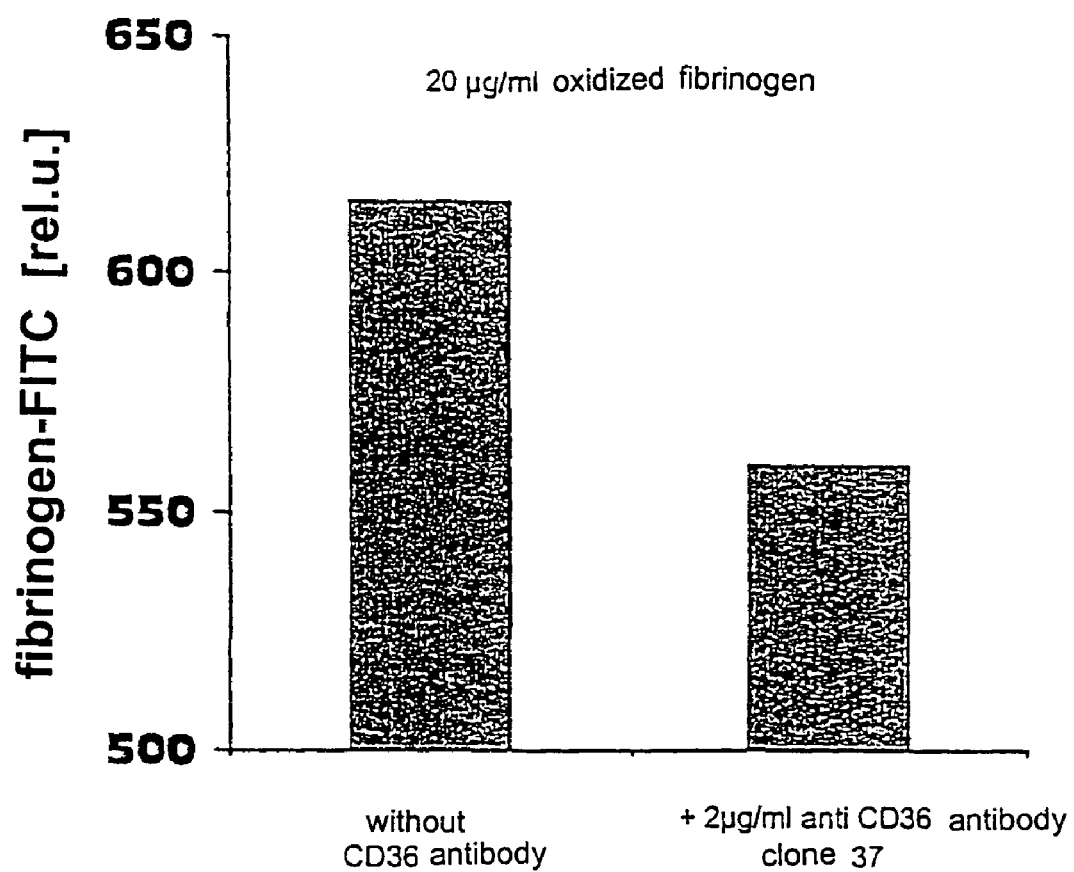

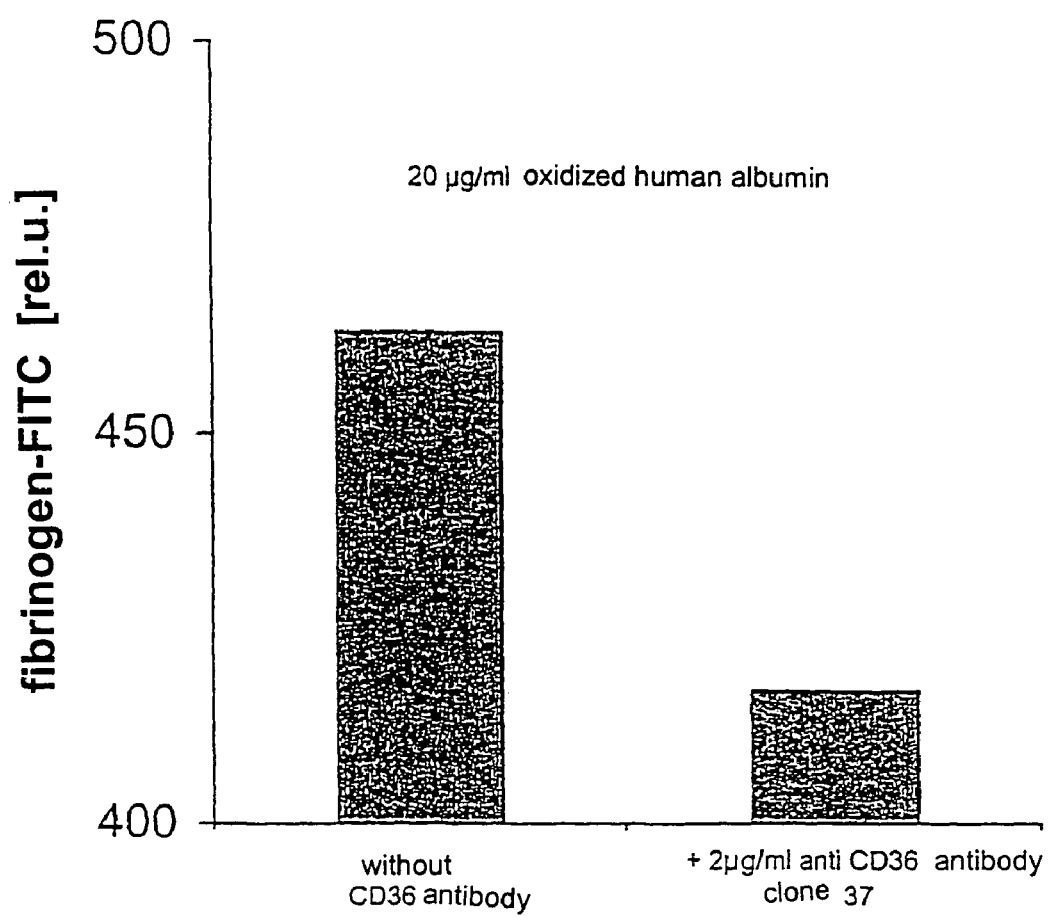

NATIVE PROTEIN

2 µg/ml OXIDIZED PROTEIN

5 µg/ml OXIDIZED PROTEIN

10 µg/ml OXIDIZED PROTEIN

4b)
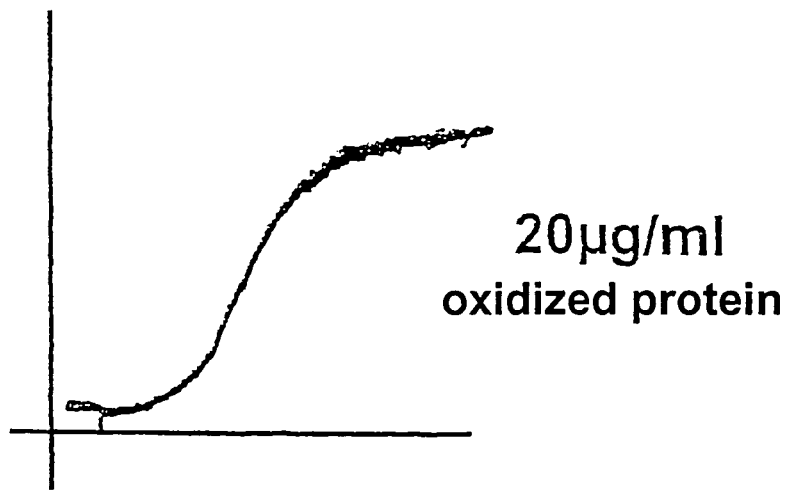
20µg/ml
oxidized protein
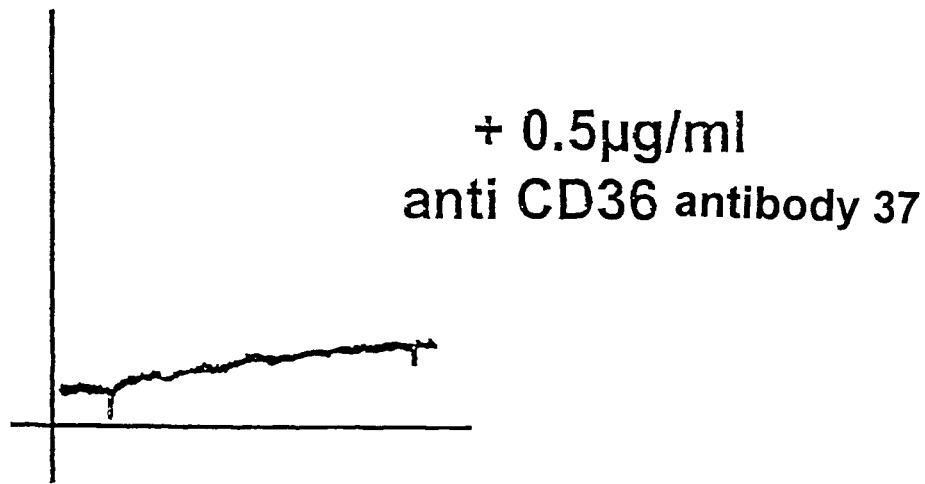
+ 0.5µg/ml
anti CD36 antibody 37
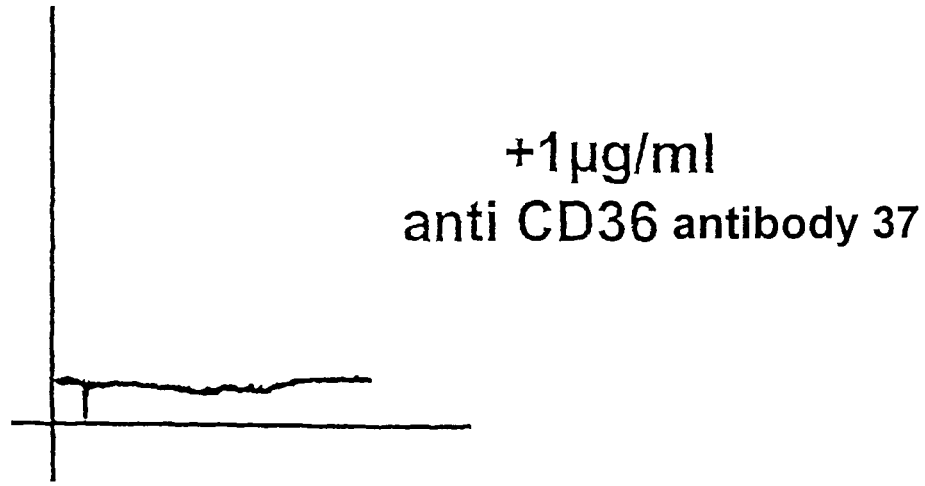
+1µg/ml
anti CD36 antibody 37

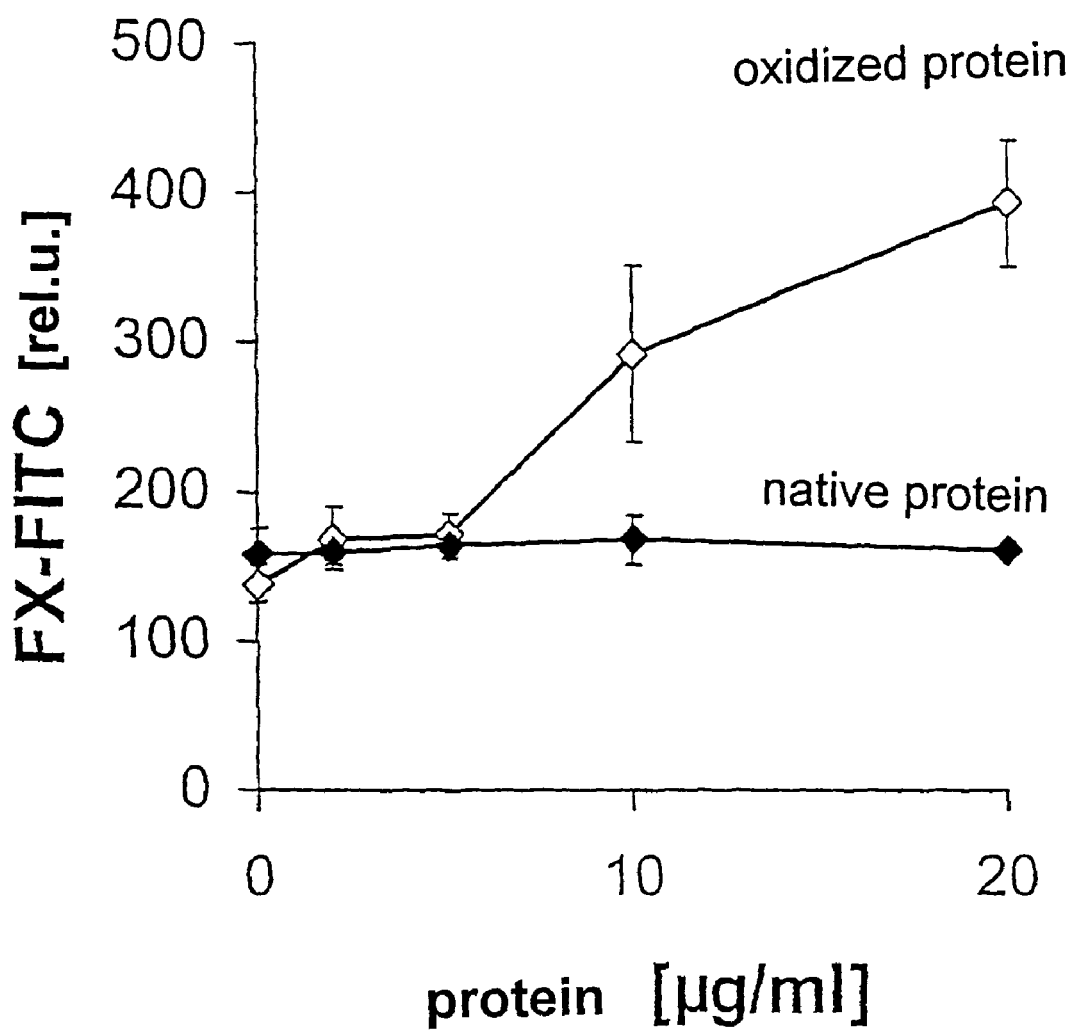

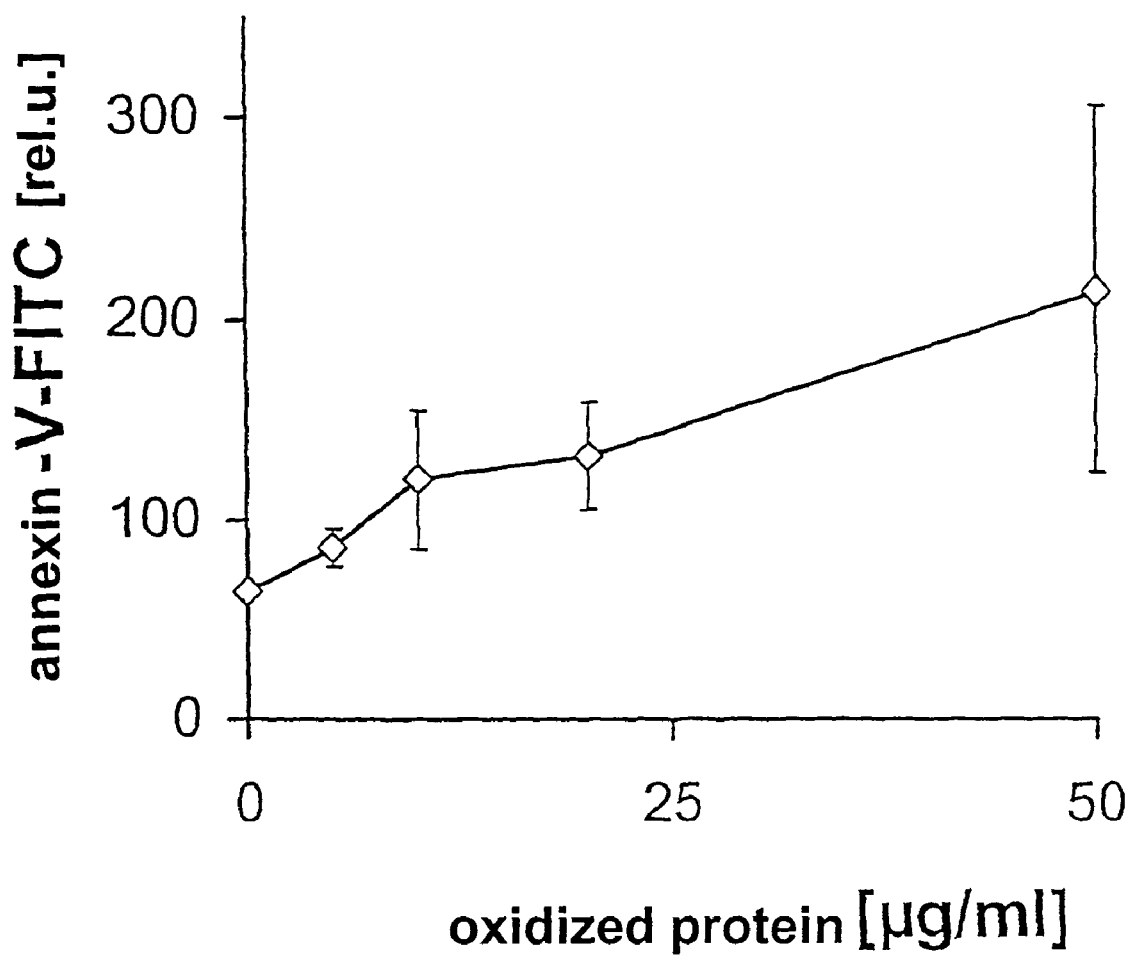

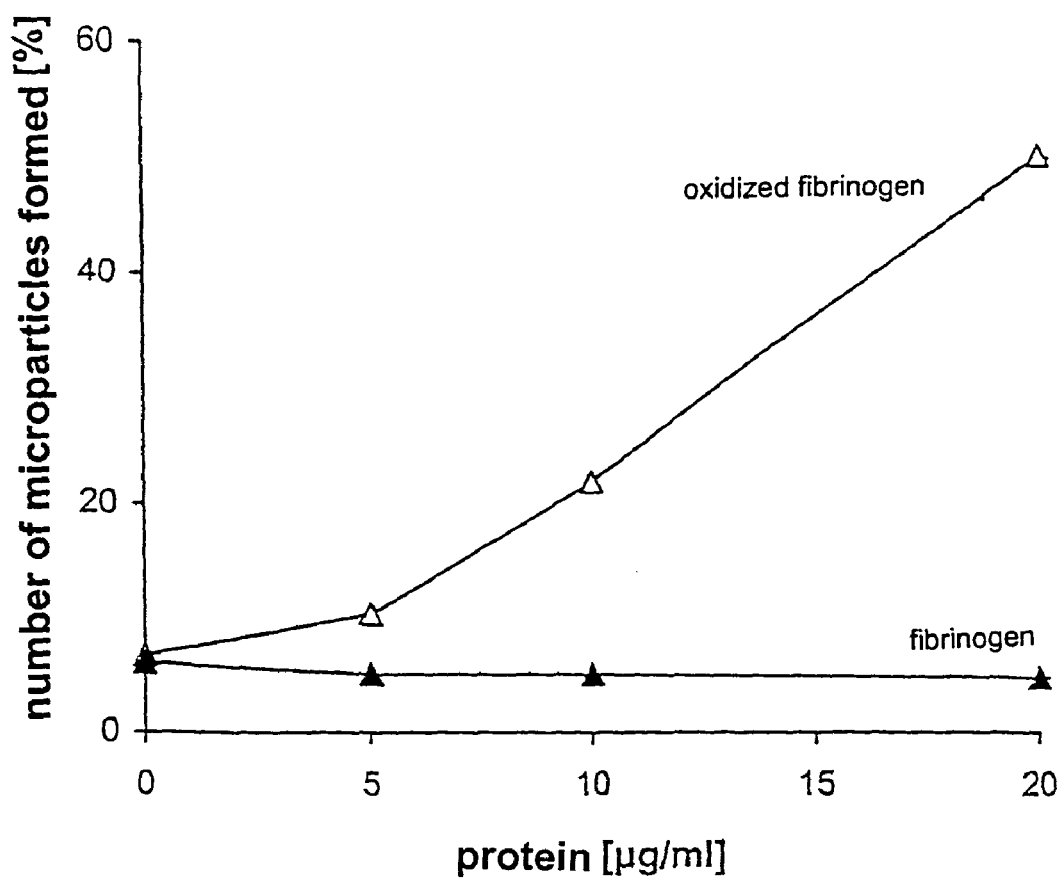

5e)
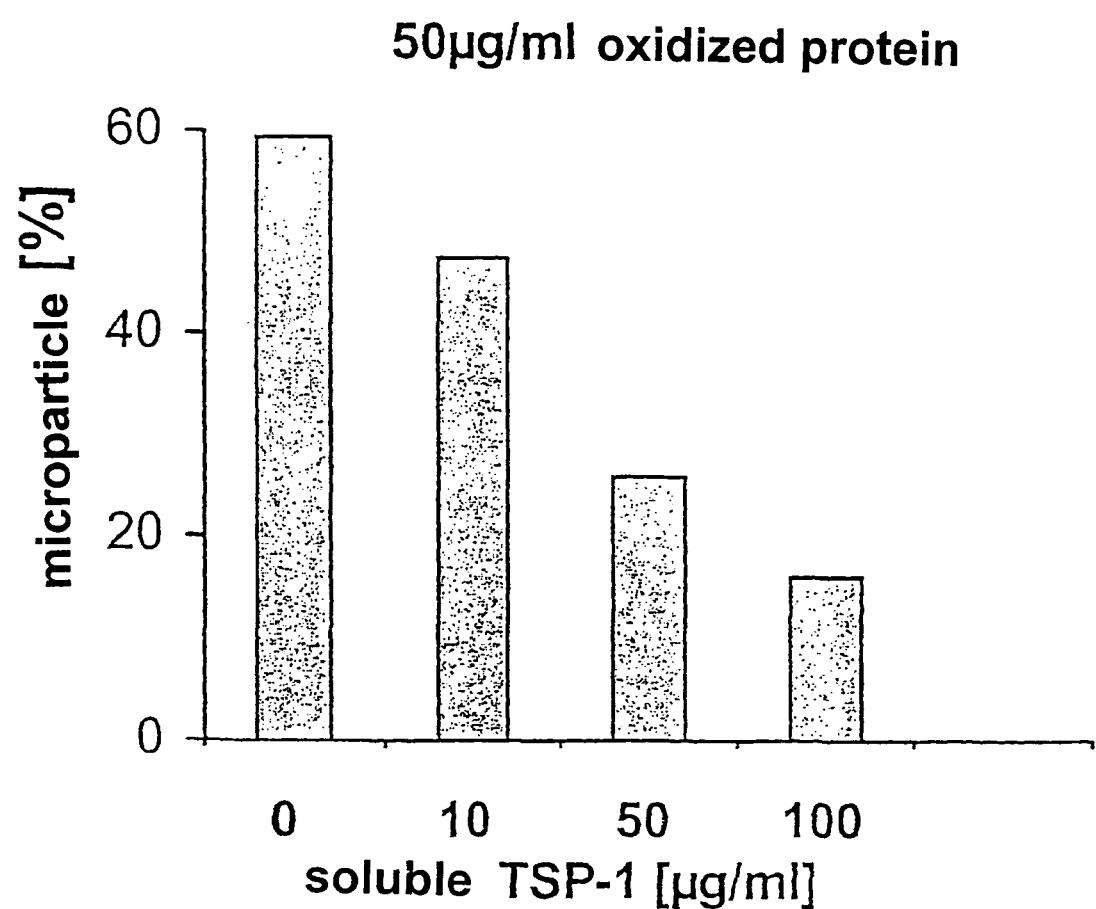

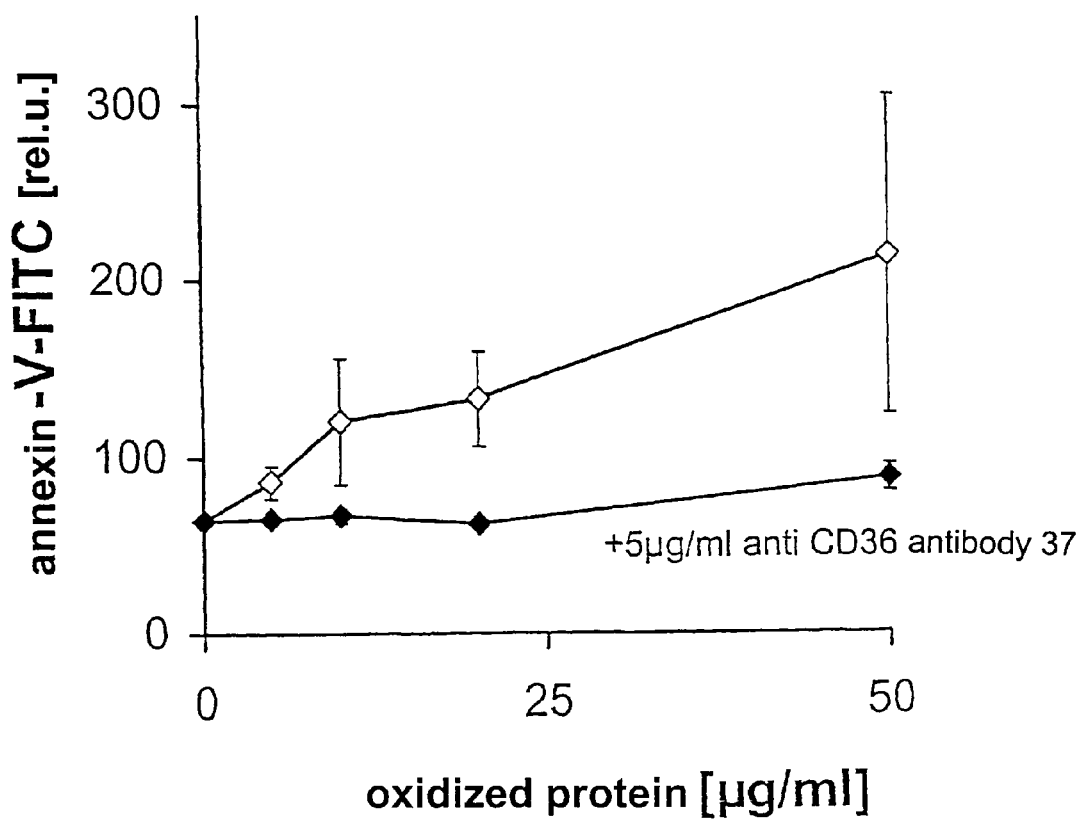

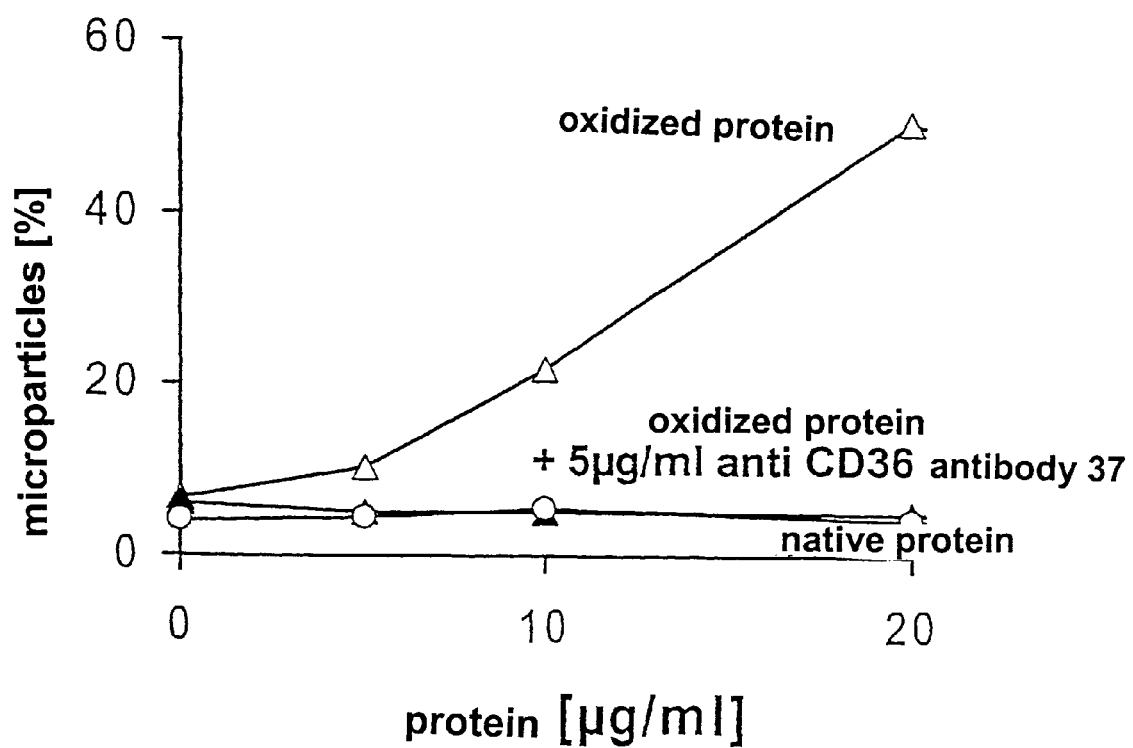
5g)

a)

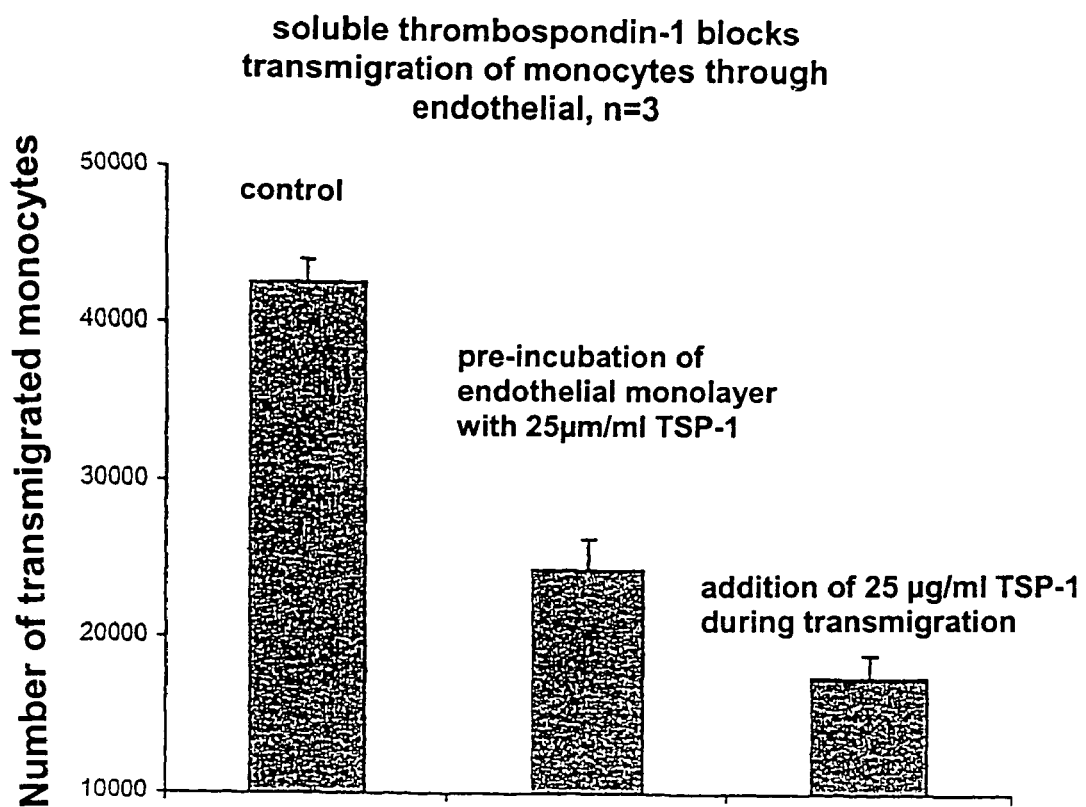

a)

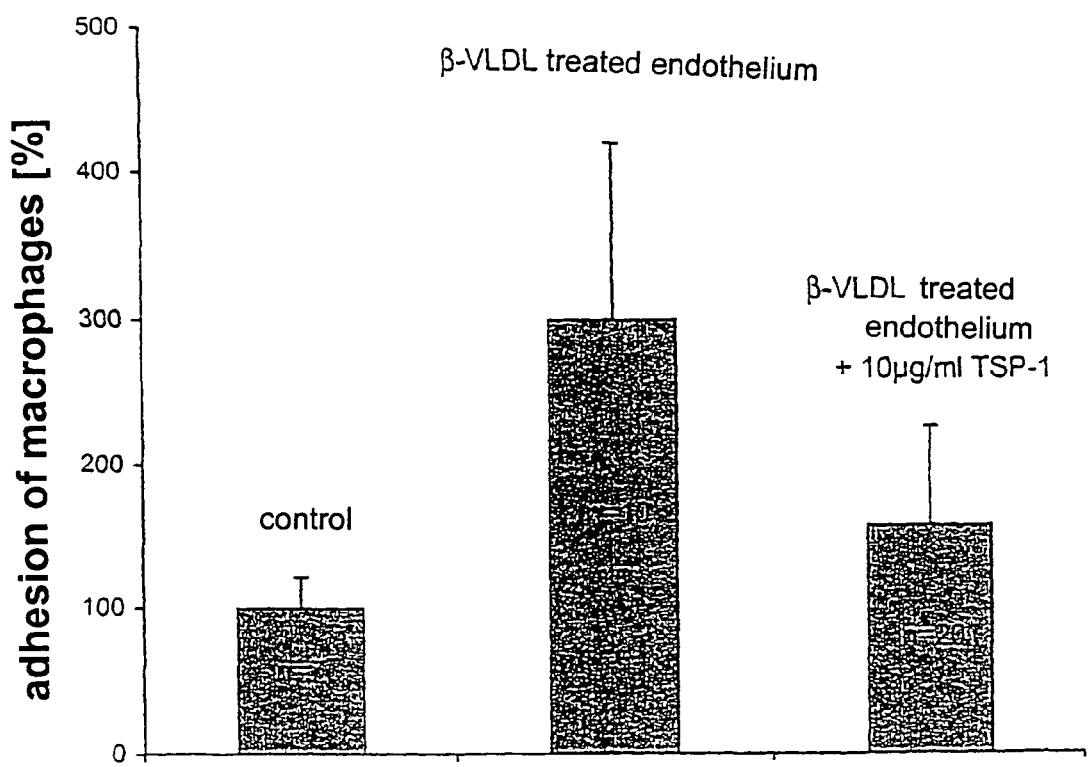

a)

TSP-1 prevents Arthus reaction

11b)
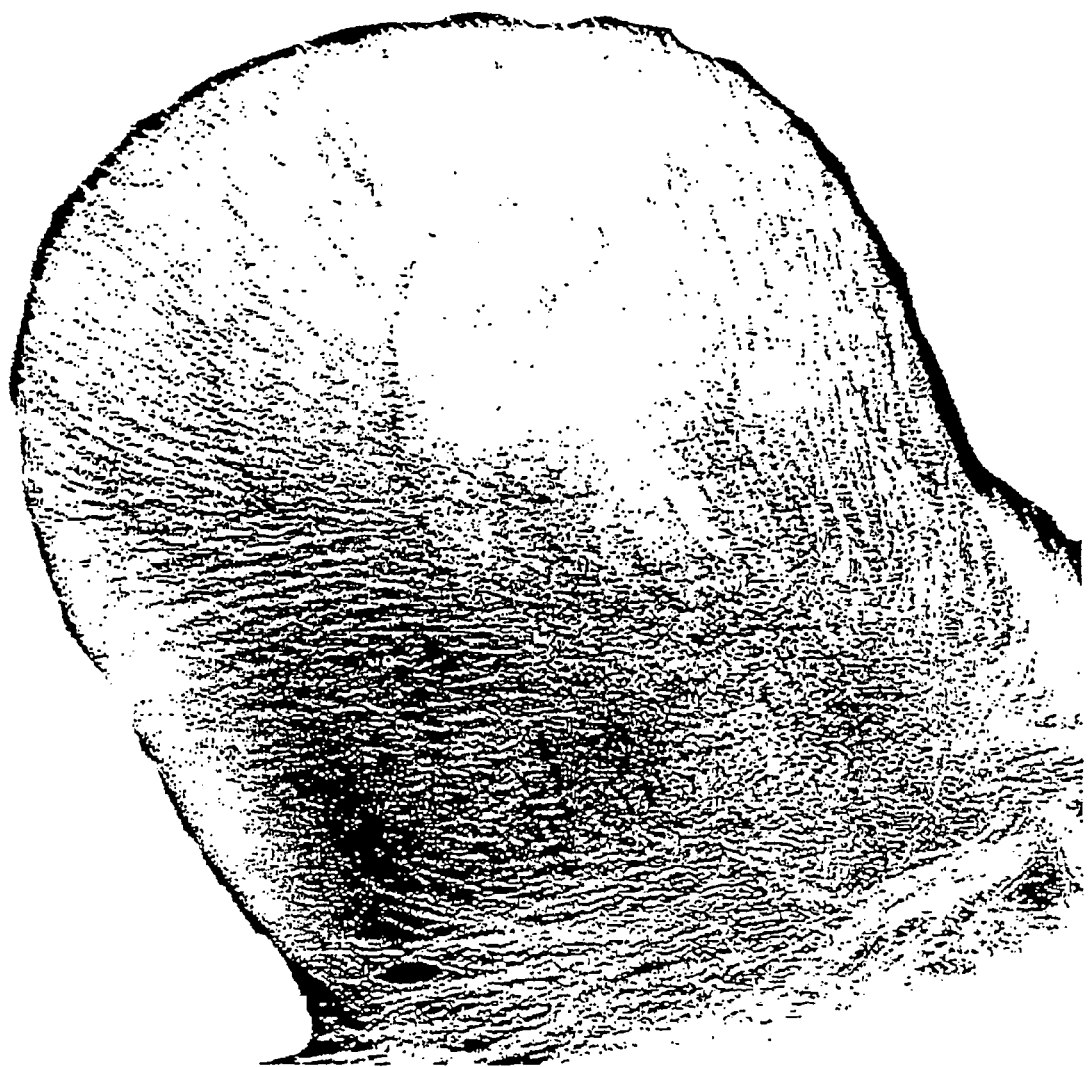
Arthus reaction with control buffer

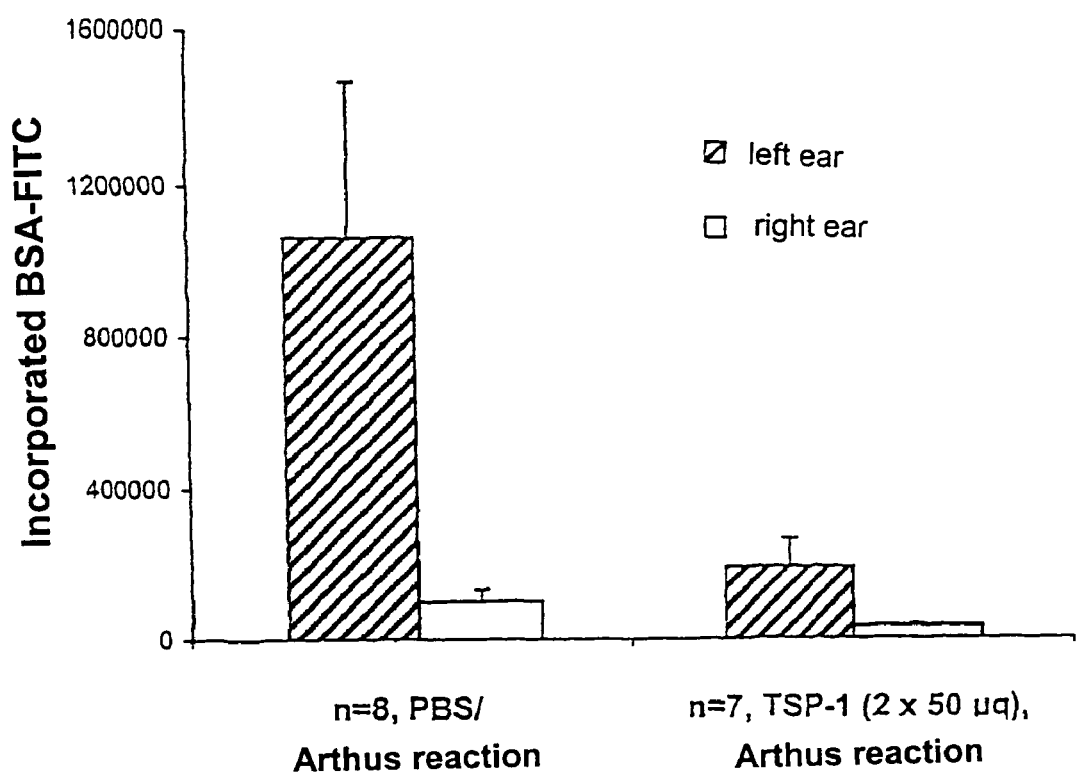

a) thrombocytes 15b) microvascular endothelial cells
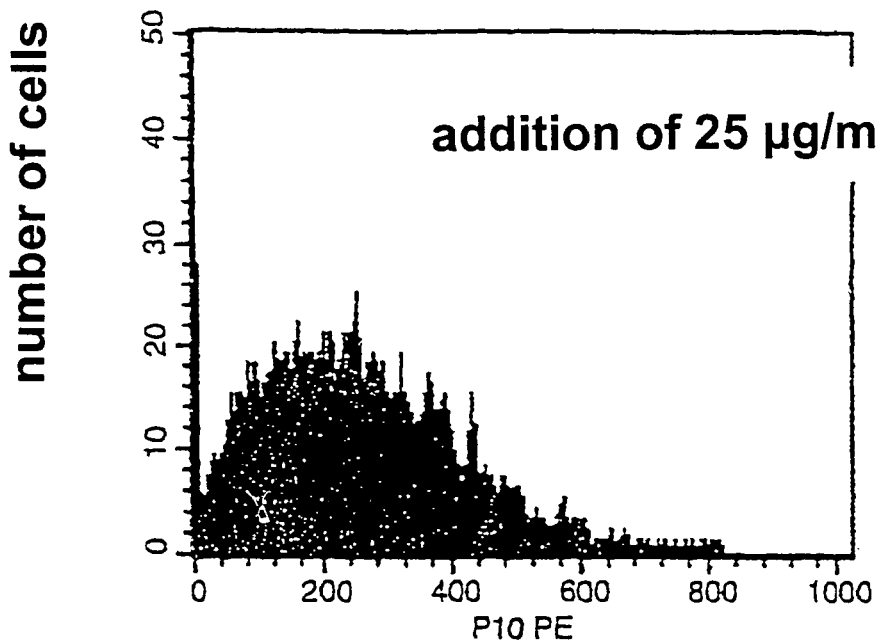
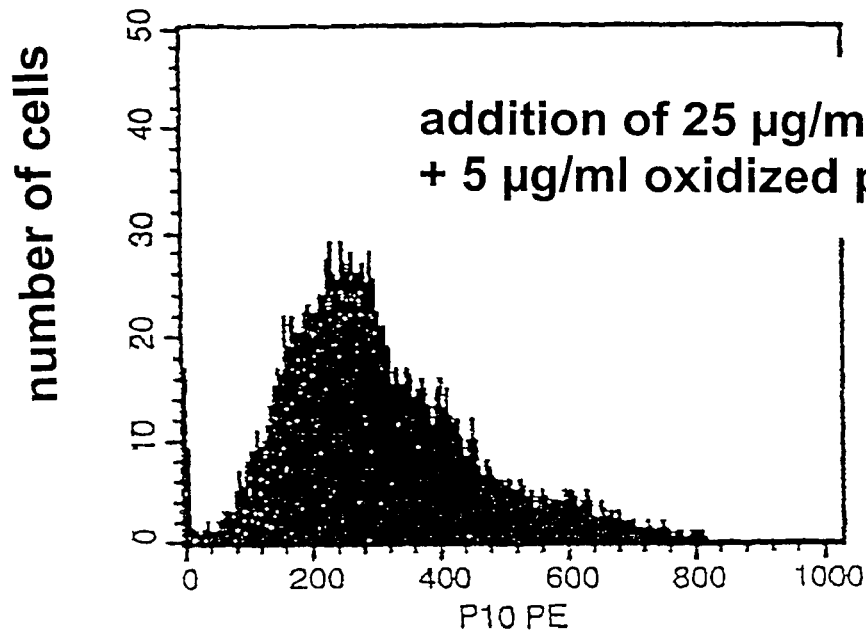

15c) monocytes
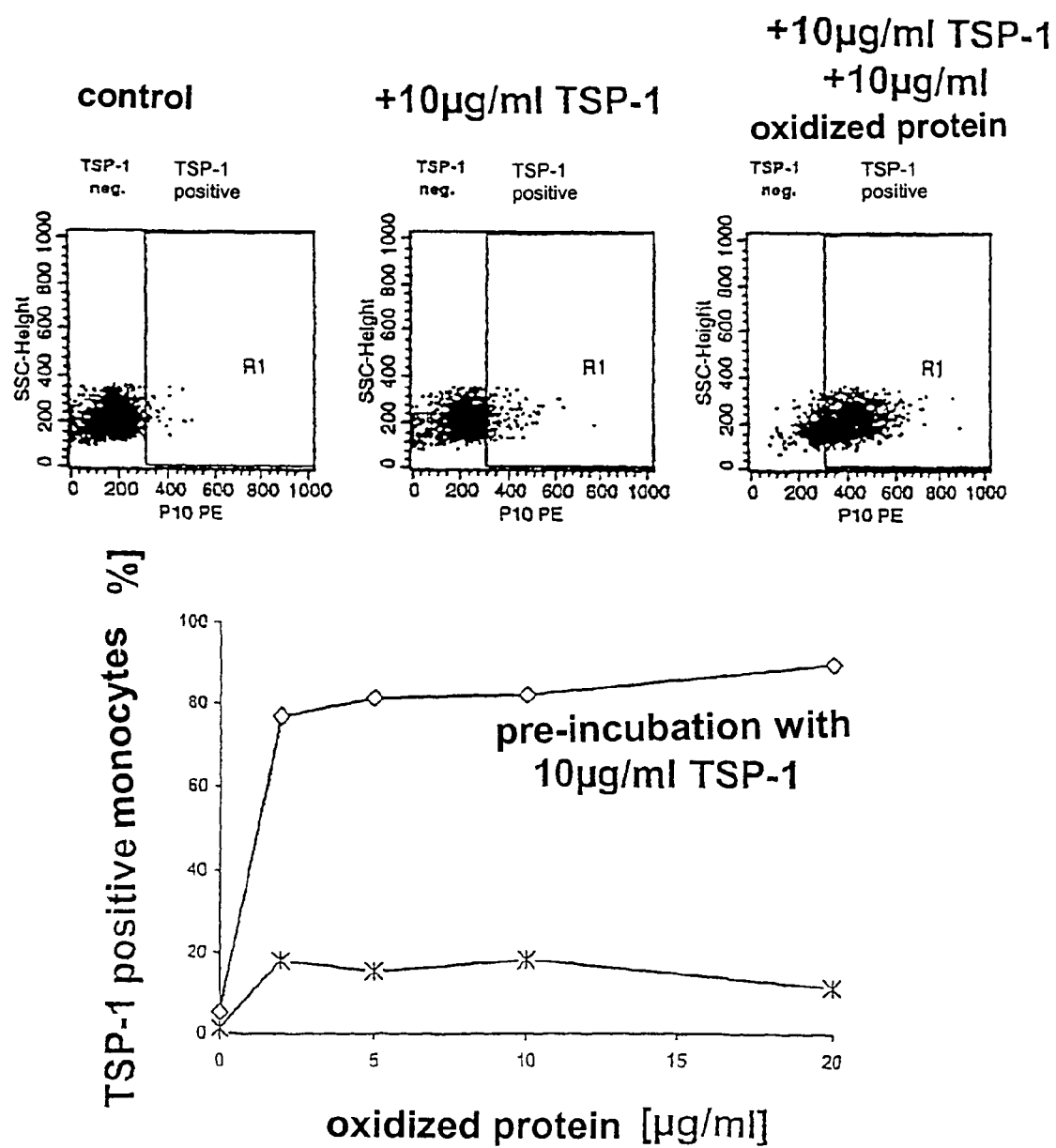

15d) Jurkat- cells
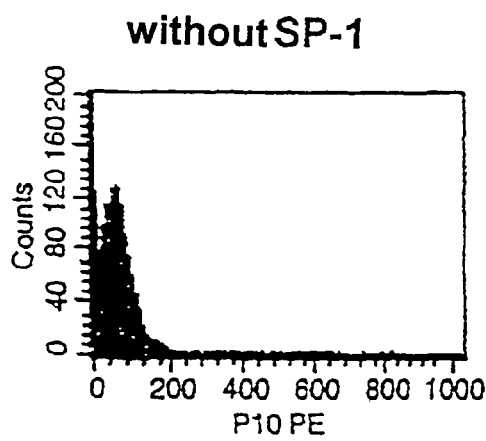
without SP-1
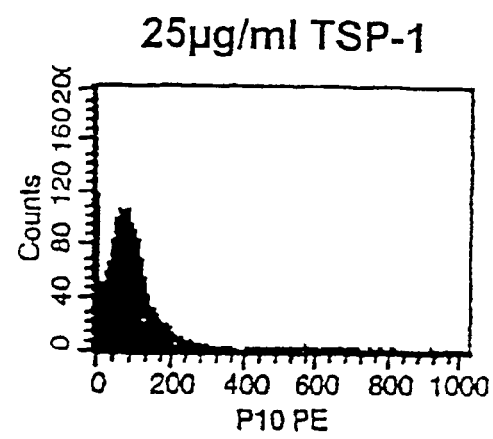
25µg/ml TSP-1
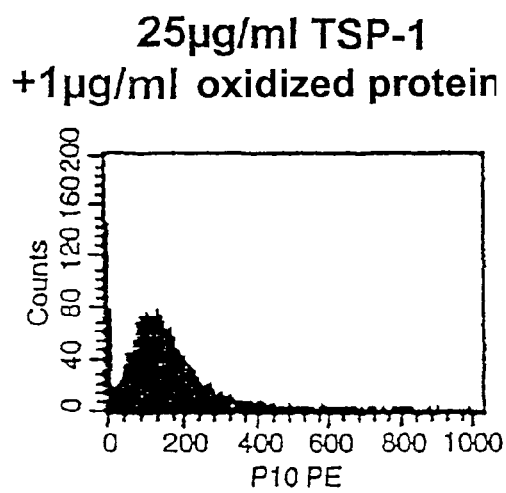
25µg/ml TSP-1 +1µg/ml oxidized protein
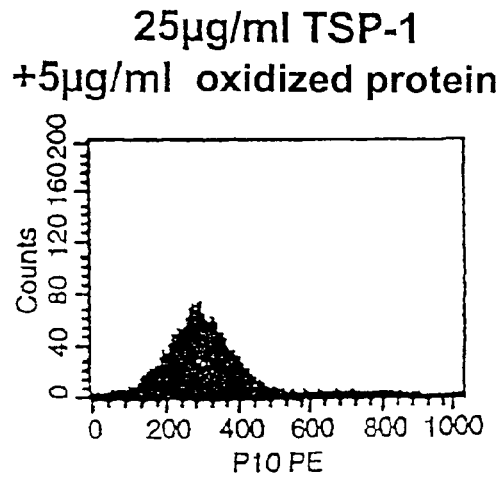
25µg/ml TSP-1 +5µg/ml oxidized protein

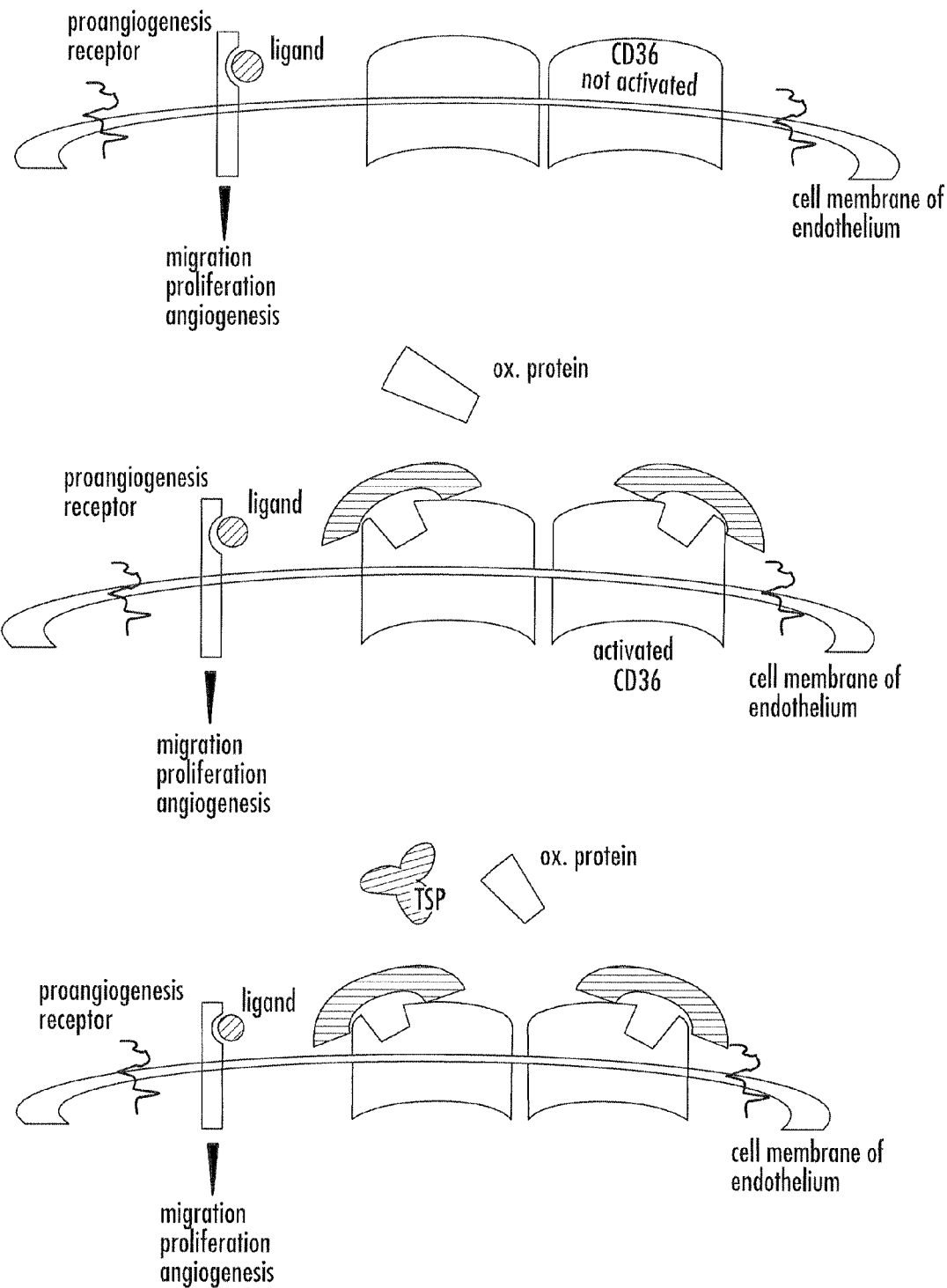

OXIDIZED PROTEINS AND OXIDIZED PROTEIN INHIBITOR COMPOSITIONS AND METHODS OF USE THEREOF

The present invention relates to substances that inhibit the binding of oxidized proteins to CD36 or that inhibit functions of CD36 induced by the interaction of CD36 with oxidized proteins, and their use as a medicament for humans and animals.

Oxidative modification of proteins is regarded as a critical step for the pathogenesis of various diseases, which range from atherosclerosis (arteriosclerosis) and neurodegenerative diseases to the process of aging itself (Holvoet and Collen, 1997 Curr Opin Lipidol, Witztum and Steinberg 1991, J Clin Invest 88, 1785-92, Smith M A et al., 1996, Nature, Oxidative damage in Alzheimers, Stadtmann E R, Protein Oxidation and Aging, 1992, Science 257: 1220-24). High LDL concentrations in the blood are considered to be the major risk factor for the development of arteriosclerotic vessel diseases (Brown M S, Goldstein I L, 1986, Science 232: 34-37).

However, today there is overwhelming evidence to believe that not LDL itself but its oxidized form is the decisive trigger for changes leading to diseases that lead to arteriosclerosis (Steinberg D, Circulation 95: 1062-71, 1997). U.S. Pat. No. 5,756,067 discloses that measurement of cholesterin, triglycerides, and lipoproteins, as risk markers for developing arteriosclerosis is not sufficient, because approximately half of all heart diseases based on arteriosclerosis is present in patients who show normal plasma triglyceride and normal cholesterin values, and because arteriosclerosis can also be demonstrated angiographically in patients with normal lipid values. Therefore, processes that have not yet been published must play a causal role in the development of arteriosclerosis.

Oxidation of lipids in LDL, either in vitro, e.g. by copper induced oxidation, or in vivo, leads to the formation of reactive aldehydes (WO 98/59248). Uptake of oxidized LDL (oxLDL) by macrophages leads to the formation of so-called foam cells, a process which is regarded as initial step in the development of arteriosclerosis (WO 98/59248).

Oxidation of the lipid portion of LDL is regarded as responsible for this process. Therefore, oxLDL is induced by almost all scientists in order to investigate the formation of arteriosclerosis, by the addition of $CuSO_4$ or malonedialdehyde, an end product in lipid peroxidation. The concentration of oxLDL in plasma of patients with coronary primary heart disease or transplantation associated coronary heart disease corresponds closely to the progression of the disease, while in healthy control persons no elevated oxLDL levels can be measured (Holvoet et al., Circulation 98: 1487-94, 1998). Also chronic kidney diseases and transplant rejections are associated with high oxLDL levels (Holvoet, Collen Thromb Haemost 76(5): 663-9, 1996+ATVB 18(1) 100-7, 1998).

Also oxidations of the protein portion of LDL can lead to physiological/pathophysiological modifications. Thus, delipidated HOCl-oxLDL induces oxidative burst in macrophages (Nguyen-Khoa et al., BBRC 263: 804-9, 1999) and HOCl-oxLDL leads to thrombocyte aggregation (Volf et al., ATVB 20(8): 2011-18, 2000).

Reactive oxidants can be released from the body by phagocytes and play a decisive role in the defense against pathogenic agents, tumor monitoring and all inflammatory processes (Babior, NEJ Med 298: 659-663, 1978, Weiss J, NEJ Med 320: 365-376, 1989). Besides "professional" phagocytes, like granulocytes and monocytes, other cells like e.g. endothelial cells or smooth muscle cells also produce and release reactive oxidants.

Among these oxidative substances are $O_2$, superoxide, hydrogen peroxide, peroxynitrite, OH-radicals, hypochloric acid HOCl, $Cl_2$-gas and chloramine. It remains unclear which processes in detail contribute to the development of these oxidative substances. Ceruloplasmine, 15-lipooxygenase, myeloperoxidase (MPO) and nitric oxide synthase (NOS) were found in arteriosclerotical lesions in animals and humans and may contribute to oxidation of LDL (Carr et al., ATVB 20:1716-23, 2000). A possible oxidation pathway involves MPO. MPO, a heme-protein enzyme can halogenate and peroxidate (Carr et al.,). The best-described product of myeloperoxidase is hypochloric acid $HOCl^-$, $Cl^- + H_2O_2 + H^+ \rightarrow HOCl + H_2O$. Hypochlorite-modified proteins, in particular HOCl-oxLDL, are found in arteriosclerotical lesions (Hazell et al., 1996). HOCl modification of proteins also plays a role in other diseases, e.g. inflammatory diseases of the joints (Davies et al., Free-Radical-Biol-Med 15(6): 637-43, 1993), coagulation disorders (oxidation of thrombomodulin) (Glaser et al., J Clin Invest 90(6): 2565-73, 1992), tissue destruction mediated by granulocytes in inflammatory reactions in general (Schraufstatter et al., J Clin Invest 85(2): 554-62, 1990), ischemia, reperfusion damage (Samanta et al., Fee Radic Res Commun 7(2): 73-82, 1989), glomerulonephritis (Shah et al., J Clin Invest 79(1): 25-31, 1987), and immune regulation (NK-cell-apoptosis) (Hansson et al., J Immunol 156(1): 42-7, 1996).

CD36, also named glycoprotein IIIb (GPIIIb) or glycoprotein IV (GB IV), is a major glycoprotein of platelets, endothelial cells, monocytes, erythroblasts, epithelial cells, and some tumor cell lines such as melanoma cells and osteosarcoma cells (Asch et al J. Clin. Invest. 79:1054-1061 (1987), Knowles et al., J. Immunol. 132, 2170-2173 (1984), Kieffer et al., Biochem. J. 262:835-842 (1989)). CD36 belongs to the family of class B scavenger receptors. Members of the family also include the integral lysosomal membrane protein LIMP-II (lysosomal integral membrane protein II, Vega et al., 1991), the CLA-1 (CD36 and LIMP-II analogous, Calvo and Vega 1993), the FAT protein of adipocyte membrane (Abumrad et al., 1993), PAS IV from breast epithelial cells (Greenwalt et al., 1990 and 1992), and SR-B1 (Acton et al., (1994).

FAT protein of adipocytes is involved in binding and transportation of long chain fatty acids. PAS IV protein is an integral membrane protein of lactating breast epithelial cells, and is concentrated in apical plasmalemma. With secretion of triglycerides, it reaches the milk and is found in the milk fat globule membrane (MFGM) fraction. The sequence of PAS IV is almost identical to CD36, but there are differences in glycosylation.

SR-B1 is a scavenger receptor for LDL (Acton et al., 1994). CD36 consists of a single heavy glycosylated polypeptide chain with an apparent molecular weight of 88,000 in reduced and non-reduced condition, and has an isoelectric range between 4.4 and 6.3 (McGregor et al., 1980, Clementson 1987). The reason for not being able to determine a clearly defined isoelectric point is the variable content of sialylic acid (McGregor et al., 1981). The carbohydrate portion of 26% and a strong hydrophobicity provides CD36 with a high resistance towards degradation by proteases as long as the protein is located in the membrane (Greenwalt et al., 1992). This explains the observation that the protein is protected from attacks in regions in which inflammatory processes take place. CD36 has N- and O-linked glycosidic modifications. The amino acid sequence for CD36 derived from placenta cDNA (Oquendo et al., 1989) shows multiple hydrophobic regions and two presumably transmembrane regions.

Certain functions have been postulated for CD36. It has been described as a receptor for collagen (Tandon et al., 1989). Purified CD36 binds to fibrils of collagen type I, and Fab fragments of a polyclonal antibody directed against CD36 inhibit collagen-induced aggregation.

However, analysis of platelets, which lack CD36, show that CD36 is not strictly required for activation of platelets by collagen. Our joint experiments with colleagues of the group of J. J. Sixma (Utrecht) showed no difference in adhesion of CD36-deficient platelets and control platelets to bovine or human collagen type I or III in a static system or under the influence of low, intermediate, and high shear rates in a perfusion chamber when using heparin blood and physiological $Ca^{2+}$ concentrations (Saelman et al., 1994).

CD36 deficient platelets aggregate normal with horn collagen, a mixture of equine type I and type III collagen, and with purified bovine and human collagen type I and III (Kehrel et al., 1991 and 1993). The secretion of α-granulae and dense granulae induced by type I or III collagen is not different in CD36 deficient platelets and control platelets (Kehrel et al., 1993). Daniel and coworkers showed that the signal transduction after activation with collagen type I in CD36 deficient platelets and control platelets is equal (Daniel et al., 1993).

CD36 is a receptor for thrombospondin-1 (TSP-1) (Asch et al., 1987, McGregor et al., 1989). On resting, thrombocyte CD36 threonine (92) is phosphorylated. Dephosphorylation allows the binding of thrombospondin (Asch, Science 1993). Purified CD36 binds specifically to thrombospondin. This binding is $Ca^{2+}$-dependent and cannot be inhibited by RGE peptides. The monoclonal antibody OKM5, which is directed against CD36, inhibits binding of thrombospondin to platelets activated by thrombin (Asch et al., 1989). Leung and coworkers reported that two peptide regions on CD36 influence binding of thrombospondin. Peptide 139-155 enhances platelet aggregation in platelet-rich plasma, which has been induced by ADP or collagen. However, peptide 93-110 partly inhibits collagen-induced aggregation, and also blocks binding of CD36 to immobilized thrombospondin. This peptide is not able to bind thrombospondin on its own, but can in the presence of peptide 139-155 (Leung et al., 1992, Pearce et al., 1993). The sequence SVTCG (SEQ ID NO:3) of thrombospondin binds to CD36 with high affinity (Li et al., 1993). Silverstein et al., (1992) demonstrated the relevance of CD36 for thrombospondin binding by experiments with "sense" and "antisense" transfected melanoma cells. The binding site for thrombospondin on CD36 is between amino acids 93-120 (Frieda et al., 1995).

CD36 is also described as a binding mediator between platelets, endothelial cells, monocytes, or C32 melanoma cells on the one hand and erythrocytes infected with malaria parasite *Plasmodium falciparum* on the other hand (Barnwell et al., 1989). Binding of infected erythrocytes to caterpillar endothelial cells, called sequestration, is of decisive significance for the often deadly end of malaria tropica, if sequestration takes place in the brain (celebral malaria). Infected erythrocytes bind to immobilized purified CD36 (Ockenhouse et al., 1989). COS cells in which cDNA for CD36 is expressed are capable of binding to malaria-infected erythrocytes (Oquendo et al., 1989). With the help of antiidiotype antibodies against the monoclonal anti-CD36 antibody OKM5, a binding partner on infected erythrocytes, the sequestrine was found (Ockenhouse et al., 1991). Contact with infected erythrocytes activates platelets and monocytes (Ockenhouse et al., 1989). CD36-deficient platelets do not show any binding capability for infected erythrocytes in the hands of Tandon et al., (1991). In contrast, we have observed that binding is only disrupted in the presence of EDTA. In the presence of $Ca^{2+}$ and $Mg^{2+}$ we could clearly observe rosetting of *Plasmodium falciparum*-infected erythrocytes and CD36-deficient platelets (Kronenberg et al., 1992). Besides CD36, further binding mediators for malaria infected erythrocytes have been described and among these are thrombospondin, which needs bivalent cations for this function (Berendt et al., 1989, Roberts et al., 1985). Thrombospondin might be able to mediate the binding of CD36-deficient platelets to infected erythrocytes, which was observed by us. Binding of *Plasmodium falciparum*-infected erythrocytes to CD36 is inhibited by CD36 peptides 145-171 and 156-184 (Baruch et al., 1999). Also, a role of CD36 in signal transduction is often discussed (Shattil and Brugge 1991). In immunoprecipitation of CD36 from resting platelets, tyrosine kinases of the src gene family $pp60^{fyn}$, $pp62^{yes}$ and $pp54/581^{lyn}$ are coprecipitated, which indicates a close association with CD36 (Huang et al., 1991). The meaning of this discovery is still unclear. Some antibodies against CD36 activate platelets and monocytes (Aiken et al., 1990, Schuepp et al., 1991). IgM antibody NLO7 activates platelets with the help of the complement system (Alessio et al., 1993). As a further function of CD36, its role in thrombotic thrombocytopenic purpura (TTP) is described (Llan et al., 1991). A protein (p37), which is present in plasma of TTP patients, agglutinates platelets, mediated by CD36. The meaning of this finding is still unknown. Peptide VTCG (SEQ ID NO:4) from thrombospondin inhibits the phosphatidylinositol (3,4) bisphosphate synthesis in platelets activated with thrombin. CD36 is one of the thrombospondin receptors, which mediate the later activation of PI-3-kinase and phospholipase C (Trumel, Payrastre, Mazarguil, Chap, Plantavid, personal communication).

CD36 is involved in the transport of long chain fatty acids in muscle tissue cells.

Overexpression of CD36 in muscle cells of transgenic mice led to enhanced cellular uptake of fatty acids, increased fatty acid oxidation by contractile muscles, and reduced the concentration of triglycerides and free fatty acids in the plasma. The mice had reduced body weight, in particular reduced body fat in comparison to control mice.

The lack of CD36 in humans leads to the loss of uptake of long chain fatty acids, which are the main energy source for the heart muscle, in heart muscle cells, and consequently to elevated appearance of innate hypertrophic cardiomyopathies (Fuse et al., 1998). Also, CD36-deficient mice show a defect in the transport of fatty acids in cells and a disturbed lipoprotein metabolism (Febrraio et al., 1999).

CD36 mediates the arachidonic acid-mediated platelet aggregation (Dutta-Roy et al., 1996) and binds to negatively charged phospholipids in cell membranes (Ryeom et al., 1996). In particular, phosphatidylserine (PS) and phosphatidylinositol (PI) are specifically bound by CD36 with high affinity (Rigotti et al., 1995). Because apoptotic cells express phosphatidylserines on their surface, contact with phagocytotic cells can be mediated by CD36 (Fadok et al., 1998, Alberts et al., 1998). Phosphatidylserine presumably binds to the CD36 sequence 162-183 (Yamaguchi et al., 2000). CD36 binds to cholesteryl hemisuccinate and can be easily purified by this reaction (Kronenberg et al., 1998).

The main function of CD36 might be its role as receptor for oxidized LDL. This role was first described by Endemann et al., 1993. Transfection experiments with a cDNA clone, which codes for CD36 in the human macrophages-like-THP-cell line, led to a newly identified binding capability of the cell for $Cu^{2+}$-oxidized LDL. The monoclonal CD36-specific antibody OKM5 inhibits binding of $Cu^{2+}$-oxLDL to platelets by 54%. The binding site for $Cu^{2+}$-oxLDL lies in the region of the CD36 sequence 155-183 (Puente et al., 1996). Nicholson et al. suggested that $Cu^{2+}$-oxLDL presumably binds to CD36 by its lipid portion (Nicholson et al., 1995). Macrophages from blood donors, which are deficient for CD36 on monocytes, have significantly reduced (~40%) uptake of oxLDL in comparison to controls (Nozaki et al., 1995).

Vitamin E (alpha-tocopherol) inhibits the uptake of $Cu^{2+}$-oxLDL in smooth muscle cells of the aorta by inhibiting CD36 (Ricciarelli et al., 2000). The binding of oxLDL to murine CD36 is partly prevented by oxidized phospholipids, which are associated with the lipid and protein portion (Boullier et al., 2000). It has recently been found that CD36 is not only the receptor for $Cu^{2+}$-oxLDL, but also for $NO_2$-LDL, and that CD36 is responsible for $NO_2$-LDL-mediated foam cell formation (Podrez et al., 2000).

This binding is competitively inhibited by oxidation products of the lipid 1-palmitoyl-2-arachidonyl-sn-glycero-3-phosphocholine. Therefore, the authors speculate that the myeloperoxidase-catalyzed peroxidation of lipids is required to mark phospholipid containing targets for phagocytosis by CD36 containing cells. In accord with its role as receptor for oxLDL, CD36 is found on macrophages loaded with lipids in arteriosclerotic plaques (Nakata et al., 1999), and smooth muscle cells may develop to foam cells by expression of CD36 in vivo (Ohya et al., 2000).

Lack of CD36 seems to be a protection against arteriosclerosis. Therefore, mice that lack ApoE protein develop arteriosclerotic plaques under a corresponding diet. If the CD36 gene in these mice is also knocked out then, under the same conditions as their CD36 containing control relatives, the mice develop 76% less arteriosclerotic lesions in the aortic tree under a fat rich diet, and 45% less plaques in the aortic sinus under normal diet.

Macrophages of CD36- and ApoE-double knock-out mice internalize less than 40% of copper oxidized LDL and $NO_2$-LDL (Febbraio et al., 2000).

Blocking thrombotic and arteriosclerotic functions of CD36, while simultaneously not affecting the important CD36-mediated uptake of long chain fatty acids in the cell, would be an important step in the fight against vessel diseases.

This problem is solved by the present invention. In the context of the present invention it has been found that cell functions that oxLDL triggers through CD36 can also be triggered by other substances. Surprisingly, these other substances are oxidized proteins, which do not need to have a lipid portion. In the body, proteins are oxidized for defense against infection, in arteriosclerotic plaques, or in acute or chronic inflammations. In the following disclosure, some reactions are mentioned by way of example that are not only triggered by oxLDL, but are also triggered by other oxidized proteins and CD36:

(1) Activation of thrombocytes
 →on the one hand, thrombosis, heart attack, and stroke, but on the other hand, also hemostasis
(2) Damage of endothelial cells
 →ischemia, inflammatory reactions, edema formation, and disturbance of prostacyclin release
(3) Activation of leucocytes, e.g.:
  a) elevated adhesion of leucocytes to endothelial cells;
  b) support of transmigration of leucocytes through endothelium and epithelia;
  c) homing of leucocytes in arteriosclerotic plaques;
  d) priming and triggering of oxidative burst in phagocytes; and
  e) tissue factor expression on monocytes, in particular increase of the reaction triggered by lipopolysaccharide (LPS).
 →damages by inflammatory reaction, thrombosis etc.
(4) Activation of smooth muscle cells (SMCs):
  a) proliferation of SMCs, and
  b) intimal swelling in arteriosclerotic plaques.
 →reocclusion after bypass, stent, PTCA; development of arteriosclerosis
(5) Stimulation of renin release from juxta-glomerulic cells
 →renin dependent high blood pressure in kidney diseases.
(6) Formation of foam cells by stimulation of the uptake of coincubated LDL by macropinocytosis.
 →development/increase of arteriosclerosis
(7) Apoptosis of vessel cells in the center of arteriosclerotic lesions.
 →necrosis, plaque rupture
(8) Stimulation of the expression of matrix metalloproteinases in endothelial cells.
 →stimulation of rupture of arteriosclerotic plaques.

Additionally, it is shown by this invention that not only does IDAAT (immune defense activated antithrombin, patent application No. DE 100 45 047.4) bind to HIV GP120 and to CD4, but it also binds to other oxidized proteins. HIV GP120 comprises a CD26 homologue sequence (Crombie et al., 1998).

It has also been shown by this invention that not only IDAAT but also other oxidized proteins mediate the binding of thrombospondin to cells like thrombocytes, monocytes, endothelial cells, and T cells. Therefore, there is a compelling reason to believe that oxidized proteins in general induce thrombospondin mediated cell reactions, like the inhibition of angiogenesis, the defense of HIV infections, the regulation of inflammatory processes by e.g. down regulation of IL-12 in monocytes, and upregulation of IL-10. Hence, oxidized proteins themselves can have a therapeutically useful activity in certain disease processes.

Further, it has been shown in the context of the present invention that pathological cell functions mediated by oxidized proteins can be inhibited by substances that inhibit the interaction between CD36-oxidized proteins, or which can interfere with TSP bound to CD36.

Examples of such substances include soluble thrombospondin-1 and monoclonal anti-CD36 antibody clones 37, 13, and 7, which were manufactured by us and are disclosed herein.

EXAMPLES

1. Isolation of Human Thrombospondin-1

Isolation of human thrombospondin-1 from thrombocytes was carried out as described in Kehrel et al., 1991. The description of Kehrel et al., 1991 is incorporated herewith by reference. However, in contrast thereto, the platelets were activated with thrombin, and EDTA in the wash buffer was substituted by Na-citrate (0.08 M). Additionally, the aggregation buffer and all buffers for the following purification steps were substituted with $Ca^{2+}$ at a concentration of 2 mM.

2. Hybridoma Culture for the Preparation of Monoclonal Antibodies

The preparation of monoclonal antibodies against CD36 was broadly carried out according to the instructions of Peters and Baumgartner (1990).

8-12 weeks old Balb/c female mice were immunized with purified CD36 (50 µg/boost). For immunization, the long immunization protocol (4 months) according to Baumgartner et al., 1990, was used. Approximately 14 days before the planned fusion time point, blood was taken from the animals, and the IgM and IgG titers against CD36 in the serum of the mice were determined. If the IgG titer was still significantly different from the control at dilutions of 1:100,000, spleen cells were fused with Ag 8,653 cells. Ag 8,653 cells were selected in culture medium containing 0.13 M 8-azaguanine. Lymphocytes from the spleen were prepared and fused with Ag 8,653. Directly after the fusion, fused cells (1×10⁶ spleen cells/ml) were incubated for 24 hours in selection medium (culture medium with the addition of hypoxanthine, 27.2 µg/ml, and azaserine (50 µg/ml)) in a cell culture flask (75 ml). Thereby, macrophages derive from the spleen attach to the plastic surface and no longer interfere with the actual culture of hybridoma in a 96 well plate.

The cloning steps were carried out by limited-dilution-cloning with a seed probability of 0.5 cells per well of the 96 well plate according to Wurzner 1990. Supernatants of hybridoma were tested in an ELISA for the production of IgG and IgM, respectively. IgG positive cell culture supernatants were tested for their specificity against CD36 with different methods:

19 CD36 specific clones were obtained, which did not react with CD36 deficient platelets (description: Kehrel et al., 1993, Saelman et al., 1994, Kehrel et al., 1995), but which showed significant binding to control platelets. This was proven by flow-through cytometry and by the dot blot method and immunoprecipitation. All antibodies tested recognized purified CD36. Three of these clones (clone 37, 13, and 7) inhibited the reaction of oxidized proteins with human cells (see below).

Isolation of CD36

Isolation of CD36 was carried out as described by our group (Kronenberg et al., 1998), by phase separation of the membrane proteins with Triton X-114, and subsequent affinity chromatography using cholesterol-hemisuccinate agarose.

Examples for the Preparation of Oxidized Proteins

348 µg protein (commercially available fibrinogen, human albumin, bovine serum albumin (BSA), or antithrombin) was incubated with 832 µg NaOCl (sodium hypochlorite) in 1 ml phosphate buffered saline with the addition of EDTA (0.1 mM) for 10 minutes on ice. Protein and oxidants were immediately separated after the end of the reaction by a gel filtration at 4° C. with Sepharose G25-Coarse (PD-10 column, Amersham Pharmacia).

Figure 4A:
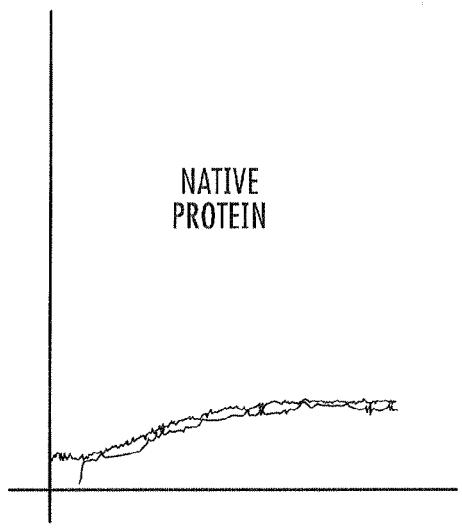
Figure 4A:
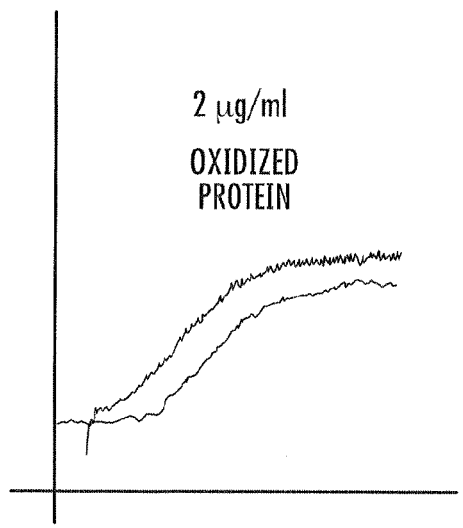
Figure 4A:
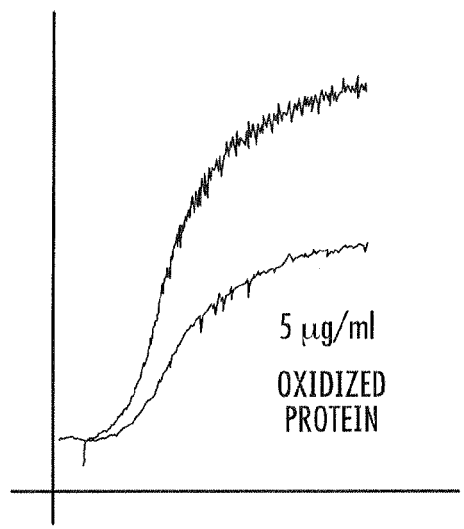
Figure 4A:
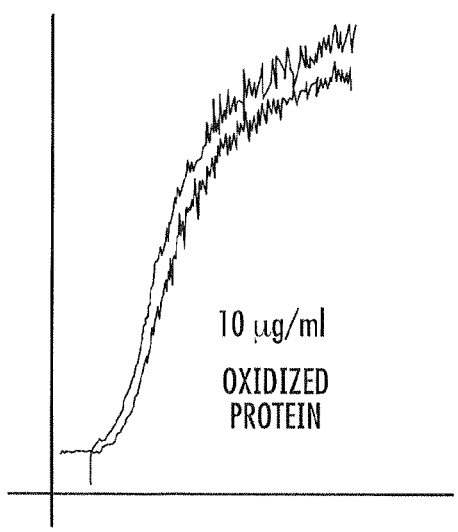
Figure 5A:
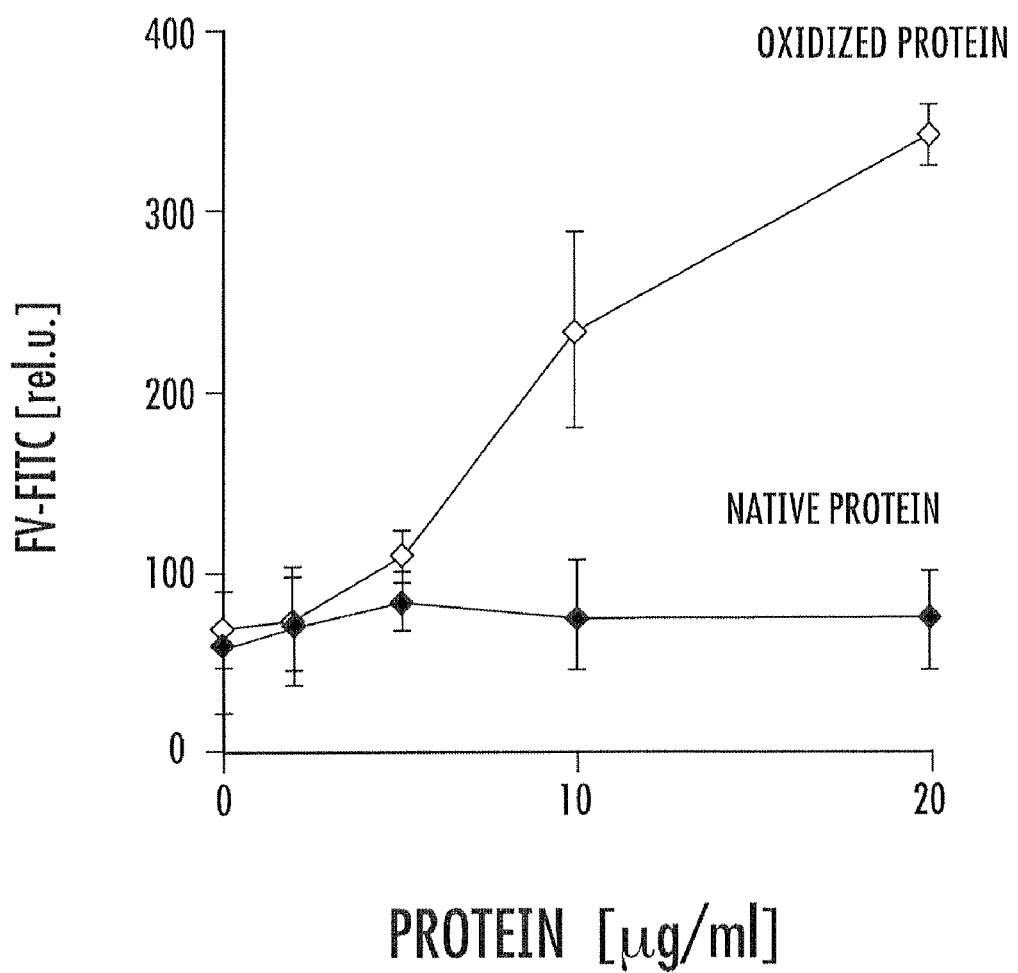

Examples for the activity of the invention:
1. Oxidized proteins (ox fibrinogen, ox antithrombin III, ox BSA, ox human albumin) bind specifically to the CD36 homologue domain of HIV GP120 protein (see FIG. 1). The interaction between oxidized proteins and HIV GP120 was determined by plasmon resonance technique in BIA-CORE System 2000.
2. Oxidized proteins activate thrombocytes. The activation of thrombocytes is inhibited by substances that inhibit the interaction of CD36 with oxidized proteins, or that interfere with thrombospondin bound to CD36.
   a) Oxidized proteins (ox fibrinogen, ox antithrombin III, ox BSA, and ox human albumin) increase, in a dose dependent manner, the adhesion of thrombocytes to adhesion proteins, like thrombospondin, vitronectin, fibrinogen, fibrin, fibronectin, and collagen (see FIG. 2a).
   This increase in adhesion is inhibited by soluble thrombospondin-1 (see FIG. 2b). This increase in adhesion is also inhibited by monoclonal anti-CD36 antibody clones 37, 13, and 7 (see FIG. 2c/d), while VCTG (SEQ ID NO:4) peptide, which inhibits binding of thrombospondin to CD36, has no effect (see FIG. 2e). The commercially available anti-CD36 antibody FA6/152 shows no inhibition (see FIG. 2f).
   b) Oxidized proteins (ox fibrinogen, ox antithrombin III, ox BSA, ox human albumin) induce, in the presence of thrombospondin-1 (10 µg/ml) and in a dose dependent manner, the binding of thrombospondin to thrombocytes (see FIG. 3a). This activation is inhibited by soluble thrombospondin-1 at a concentration of >20 µg/ml (see FIG. 3b). This activation is also inhibited by monoclonal antibodies against CD36, clone 37, 13, and 7 (see FIG. 3c-e).
   c) Oxidized proteins (ox fibrinogen, ox antithrombin III, ox BSA, ox human albumin) cause, in the presence of thrombospondin-1 (10 /ml), the aggregation of platelets (see FIG. 4a). This aggregation is inhibited by monoclonal antibodies against CD36, clones 37, 13, and 7, in a dose dependent manner (see FIG. 4b).
   d) Oxidized proteins (ox fibrinogen, ox antithrombin III, ox BSA, ox human albumin) cause, in the presence of thrombospondin-1 (10 µg/ml), the procoagulant condition of the platelets (see FIG. 5a-c), and lead to micro particle formation (see FIG. 5d). This activation is inhibited by soluble thrombospondin-1 at concentrations of ≧20 µg/ml (see FIG. 5e).
   This activation is also inhibited by monoclonal antibodies against CD36, clones 37, 13, and 7, in a dose dependent manner (see FIGS. 5f and g).
3. Oxidized proteins (e.g. ox fibrinogen, ox antithrombin III, ox BSA, ox human albumin) activate monocytes. This activation is inhibited in a dose dependent manner by certain substances, e.g., soluble thrombospondin or monoclonal antibodies against CD36, which inhibit the interaction between CD36 and oxidized proteins or which interfere with thrombospondin bound to CD36.
   a) Oxidized proteins (e.g. ox fibrinogen, ox antithrombin III, ox BSA, ox human albumin) induce a $Ca^{2+}$ signal in monocytes (see FIG. 6).
   b) Oxidized proteins (e.g. ox fibrinogen, ox antithrombin III, ox BSA, ox human albumin) induce the oxidative burst in PMNL (see FIG. 7).
   c) Oxidized proteins (e.g. ox fibrinogen, ox antithrombin III, ox BSA, ox human albumin) induce an increased transmigration of monocytes, PMNL and lymphocytes through endothelial monolayers (see FIG. 8a). This reaction is inhibited by substances that inhibit the binding of CD36 to oxidized proteins such as soluble thrombospondin or monoclonal antibodies against CD36, clones 37, 13, and 7 (see FIG. 8b).
4. Oxidized proteins (e.g. ox fibrinogen, ox antithrombin III, ox BSA, ox human albumin) play a causal role in the development of arteriosclerosis.
   a) Oxidized proteins (e.g. ox fibrinogen, ox antithrombin III, ox BSA, ox human albumin) induce a homing of macrophages in arteriosclerotic plaques. Homing was carried out according to Patel et al., 1998. In C57BL/6 mice, the migration of monocytes/macrophages into the peritoneum was induced by intraperitoneal injection of thioglycolate. After 4 days, the peritoneum was washed and activated peritoneal macrophages were obtained. In the probes, erythrocytes were lysed. Macrophages were resuspended in RPMI 1640 medium and transferred to cell culture dishes to allow adhesion. Fluorescence-marked microspheres (2 µm yellow-green fluorescence latex microspheres, molecular probes) were opsonized for 30 minutes with 50% mouse serum for better uptake by the macrophages, and were then added to the plated macrophages. The adhered macrophages phagocytosed the microspheres. Non-adhered cells and microspheres were removed from the dish by washing. Macrophages were removed from the dish on ice and were resuspended in Hanks balanced salt solution (HBSS). 50 week old ApoE deficient mice were each injected intraperitoneally with 3 times 50 μg oxidized protein, in this case oxidized antithrombin III, and placebo (only HBSS), respectively, 6 hours before intravenous injection of marked macrophages, 2 hours after injection of macrophages and 10 hours after injection of macrophages. $10 \times 10^6$ macrophages were suspended in 0.2 to 0.3 ml HBSS and injected into the tail vein. 24 hours after macrophage injection, the animals were sacrificed. The heart basis and the aorta ascendens were embedded in OCT, stored at −80° C., and 7 μm cryo-sections were prepared. Fluorescence-marked macrophages of 140 serial sections per mice from a 1 mm range of the aorta ascendens on the level of the sinus valsalva were counted. In comparison to the placebo treated $ApoE^{-/-}$ control mice, the migration of marked macrophages into arteriosclerotic plaques in mice treated with oxidized antithrombin III increased from 100±15% (n=14) to 156±9.2% (n=5) significantly (p=0.008) ("alternate welch test"). As this migration is causal to the development, the progression, and the danger of rupture of arteriosclerotic plaques, this example elucidates the importance of oxidize proteins with respect to arteriosclerosis (FIG. 9).

b) Substances that inhibit the interaction of CD36 and oxidized proteins, or interfere with thrombospondin bound to CD36, prevent/reduce the proarteriosclerotic activity of oxidized proteins. Soluble thrombospondin inhibits adhesion of macrophages to arteriosclerotically altered endothelial cells. This is a prerequisite for migration of microphages into arteriosclerotic plaque. Murine-immortalized endothelial cells were stimulated with β-VLDL (50 μg protein/ml) from plasma of ApoE deficient mice for 6 hours, and then suspended with $2 \times 10^5$ peritoneal monocytes/macrophages per ml with a shear rate of $400s^{-1}$ in a flow through chamber. β-VLDL induced a significant relative increase of the rolling leucocytes by 224±44% in comparison to the control. Addition of 10 μg/ml soluble thrombospondin inhibited this increase of adhesion completely and additionally inhibited partly the basic adhesion of macrophages to the endothelium (75±37% adhesion in comparison to the control, n=4-7; p<0.01) (see FIG. 10a). Significantly induced permanent adhesion of macrophages by β-VLDL was also reduced by thrombospondin-1 after a 5 minute wash period (100±21% control versus 300±119% β-VLDL versus 157±70% β-VLDL+TSP-1; n=4-7; p<0.01) (FIG. 10b).

5. Soluble thrombospondin-1 inhibits inflammatory reaction in vivo. In the ear of Balb/c-mice, an Arthus reaction was induced by local injection of anti-BSA at time point 0 and simultaneous injection of FITC coupled BSA into the peritoneum. Control animals (negative controls) were only injected with FITC (without BSA) into the peritoneum. After 6 hours, animals treated with anti-BSA and BSA-FITC showed a clearly developed inflammatory reaction with ear swelling (edema), FITC incorporation, migration of PMNL and petechial bleeding into the tissue. 18 mice were additionally intraperitoneally injected at time point 0, and after 0+3 hours, with 50 μg thrombospondin-1 in buffer (PBS). 16 control mice received only PBS at time point 0+3 hours. The Arthus reaction was almost completely prevented by thrombospondin. Thrombospondin-treated mice showed significantly less FITC incorporation, significantly less ear thickness (less oedems), and almost no petechia in comparison to PBS treated control animals (see FIGS. 11a-c).

6. Examples for quantification of oxidized proteins
Preparation of monoclonal antibodies that recognize epitopes on proteins or peptides, and that are directly or indirectly modified by oxidation processes:
Human albumin, antithrombin III and fibrinogen were, as described in this dsiclosure, oxidized with HOCl, and 8-12 weeks old Balb/c female mice were immunized therewith. Preparation of hybridoma and hybridoma culture was carried according to classic procedures. Supernatants of hybridoma were tested for the production of IgG and IgM, respectively. IgG positive cell culture supernatants were tested for positive reaction with oxidized protein and simultaneously negative reaction with the unaltered initial protein. Clones that produced antibodies against oxidized protein (ox human albumin, ox antithrombin III, ox fibrinogen) and simultaneously did not react with non-oxidized mother protein, were tested for cross-reaction with other oxidized proteins and peptides.
Quantification of oxidized proteins with the help of monoclonal antibodies, as disclosed above:
Such quantification is easily possible with processes like ELISA, RIA, quantitative flow-through cytometry on cell surfaces, and similar routine procedures. e.g.: quantification of oxidized human albumin with ELISA. A polyclonal antibody from rabbit against human albumin (preparation—routine procedure) was bound to the bottom of an ELISA dish (Nunc-Maxisorb) as catcher antibody. The dish was thoroughly washed with PBS pH 7.4, 0.5% Tween 20, and spaces on the plastic surface were blocked with 3% BSA for 1 hour at room temperature (RT). The dish was washed again and then incubated with differently diluted plasma, sera, supernatants of blood products (e.g. thrombocyte concentrates, erythrocytes concentrates, FFP) or buffer solutions to which defined amounts of ox human albumin have been added, for 1 hour at RT. Probe material and standard solutions, respectively, were removed, the dish was washed thoroughly and incubated with the above-described monoclonal antibody, which recognizes oxidized human albumin and which was marked with biotin, in a dilution of 1:15000 in PBS, 1% NGS (normal goat serum). The dish was again washed thoroughly for several times and incubated with Streptavidin peroxidase (1 hour, RT). After again washing the dish, it was treated with substrate solution (100 μg/well) (20 mg ortho-phenyldiamine, 5% $H_2O_2$ in a buffer of 12.15 ml 0.1 M citric acid and 12.85 ml 0.2 M $Na_2HPO_4$ plus 25 ml $H_2O$ dest.). The extinction at 405 nm, measured in an ELISA photometer, indicated the amount of oxidized human albumin. The reaction was stopped with 50 μl/well 4 N $H_2SO_4$, and the extinction was measured at 490 nm.
HOCl-oxidized human albumin in the probe was quantified with a calibration series.
HOCl-modified fibrinogen and HOCl modified antithrombin III were treated similarly.

7. Example for the documentation of the activated condition of the receptor for oxidized proteins, CD36.
Preparation of polyclonal antibodies against threonine (92) phosphorylated CD36. Peptides (15 AS) (1) Lys, Gln, Arg, Gly, Pro, Tyr, Thr, Tyr, Arg, Val, Arg, Phe, Leu, Ala, Lys (SEQ ID NO:1) and (2) Lys, Gln, Arg, Gly, Pro, Tyr, PhosphoThr, Tyr, Arg, Val, Arg, Phe, Leu, Ala, Lys (as peptide (1), but phosphorylated at threonine) (SEQ ID NO:2), were synthesized and coupled to KLH (Keyhole Limpet Hemocyanin). Polyclonal antibodies from rabbit were prepared according to standard procedures with these coupled peptides. For this, rabbits (New Zealand, white) were essentially immunized with 250 μg peptide 1-KLH and peptide 2-KLH plus the addition of complete Freund adjuvans s.c., respectively, and boostered with 250 μ peptide 1-KLH and peptide 2-KLH with the addition of Alu-Gel-S (1.3% aluminium hydroxide in water, SIGMA) 3 times, respectively. Blood was drained from the ear veins of the animals, and serum was prepared and tested for antibodies against the peptides that were used for the immunization. The antibody against phosphorylated CD36 peptide was cross-absorbed on an affinity column with non-phosphorylated CD36 peptide, so that the resulting antibody mixture only contained antibodies that specifically recognized phosphorylated non-activated CD36 (AK CD36P). (The preparation of specific monoclonal antibodies against threonine phosphorylated/dephosphorylated CD36 is possible with these peptides according to the described preparation of anti-CD36 protein antibodies.)

Figure 12:
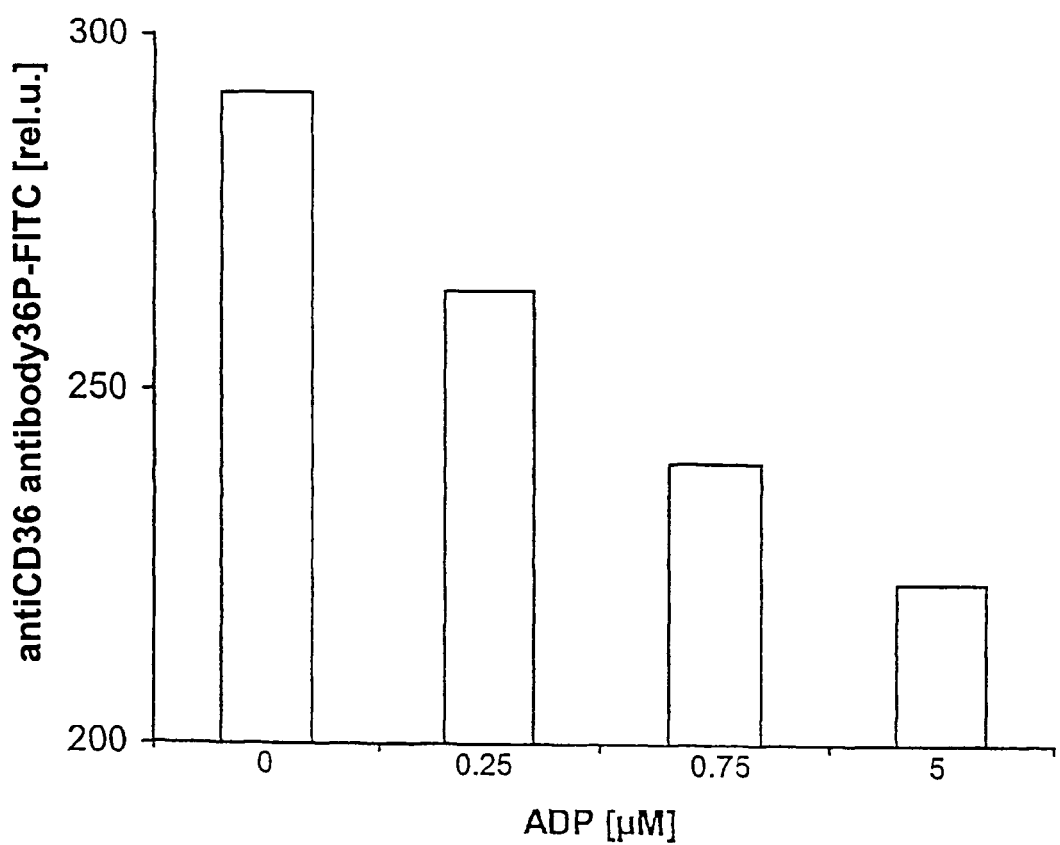

Both monoclonal antisera reacted with CD36 on the surface of platelets in flowthrough cytometry. While antibody "CD36P" directed against phosphorylated CD36 preferably recognizes CD36 on non-activated thrombocytes, antibody "CD36 total" recognizes non-phosphorylated CD36 and phosphorylated CD36. With activation of the thrombocytes, CD36 is dephosphorylated and the binding capacity for antibody "CD36P" decreases (see FIG. 12). Quantitative flow-through cytometry with both antibodies allowed the calculation of the portion of activated CE36.

Figure 13:
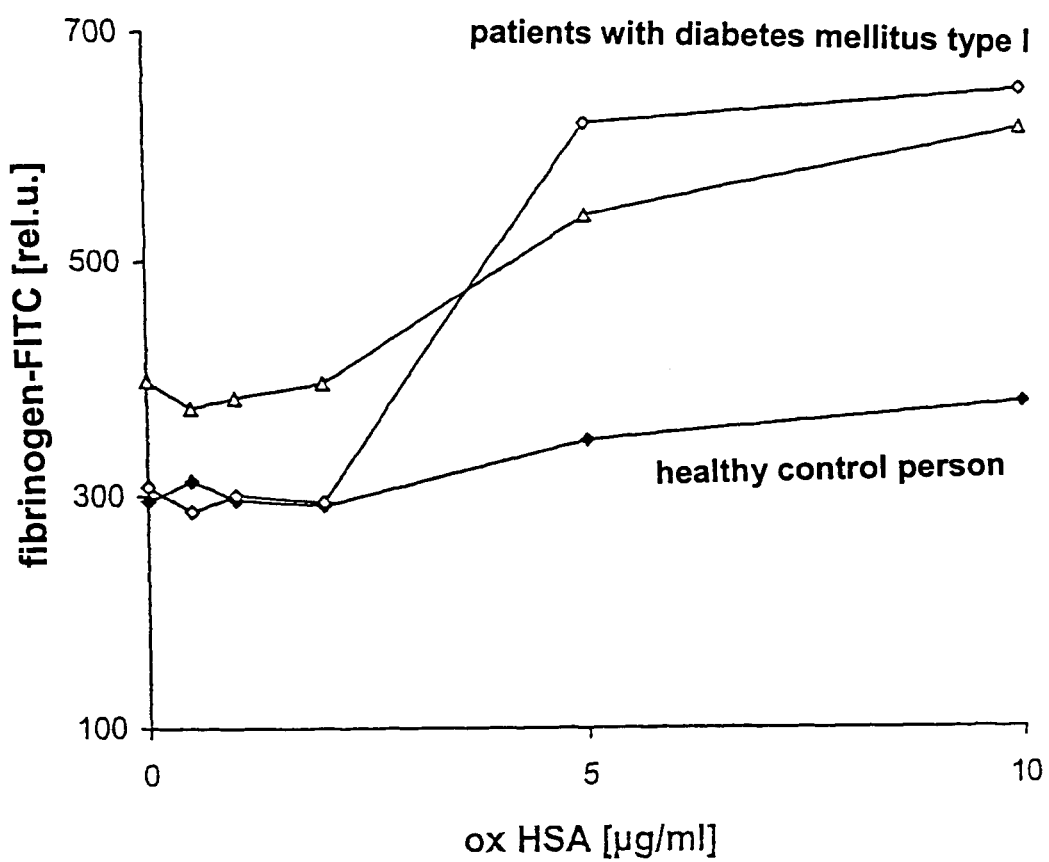

8. The organism of patients with type I diabetes is particularly susceptible to oxidized proteins:
   e.g.: thrombocytes of patients with diabetes type I react more sensitively to oxidized protein as agonist in comparison to thrombocytes of healthy control persons. Activation-dependent fibrinogen binding can be induced on thrombocytes of patients with diabetes with reduced concentrations of ox protein in comparison to thrombocytes of control persons (see FIG. 13).

Figure 14:
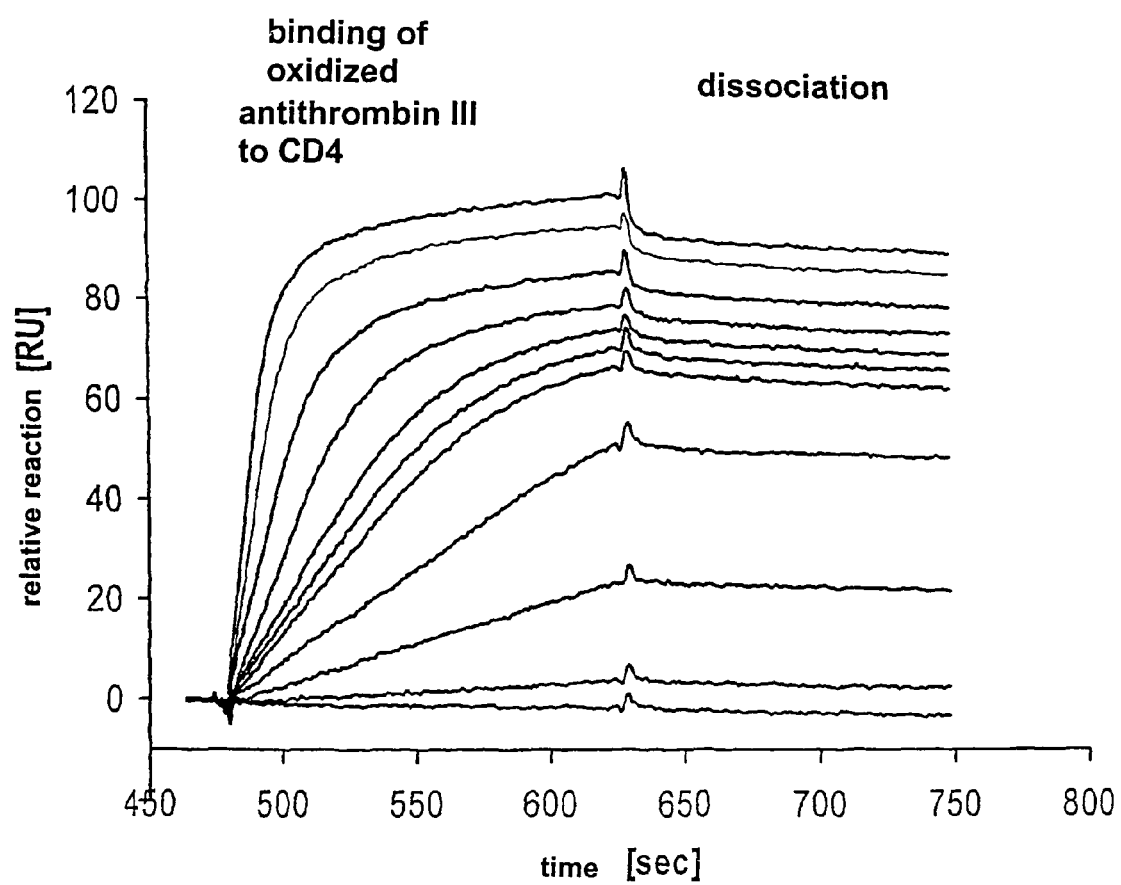
Figure 15:
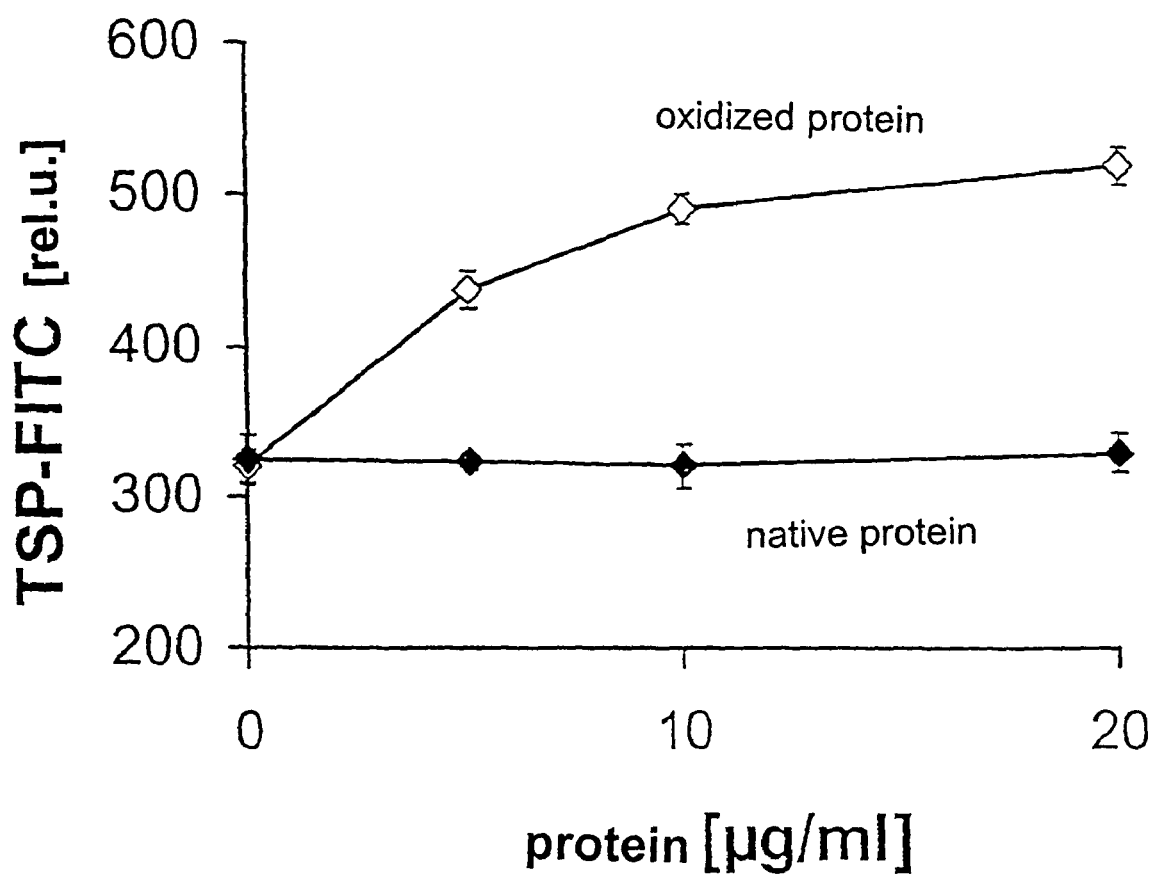

9. Oxidized proteins inhibit HW infection.
   Oxidized protein (ox antithrombin III and ox human albumin were tested) bind with high affinity to both HIV-GP120 and its receptor CD4.
   e.g.: Binding of oxidized antithrombin III and oxidized human albumin to HIV-GP120 and to CD4 was shown using a BIACORE 2000 system. Running buffer: 25 mM Tris; 100 mM NaCl pH 7.4; 1 mM $CaCl_2$; 1 mM $MgCl_2$; 0.005% Surfactant P20.
   Protein HIV-GP120: c=100 μg/ml, 200 μl
   Storage buffer: Tris/HCl, NaCl pH 7.6
   Protein CD4: c=63 μg/ml, 318 μl
   Storage buffer: 10 mM Tris; 300 mM NaCl pH 8
   Protein ox antithrombin III: c=1 mg/ml, 120 μl
   Protein ox human albumin: c=1 mg/ml, 120 μl
   C1-chip (BIACORE AB)
   Amine coupling kit (BIACORE AB)
   HIV-GP120 and CD4 were immobilized on the C1 sensor surface. For this 10 mM NaAc pH 4 was used as coupling buffer.
   Coupling conditions: HIV-GP120: 20 μl; 10 μg/ml GP120 in 10 mM NaAc pH 4; immobilized amount: 1158 RU, 300 pg
   CD4: 30 μl; 6.3 μg/ml CD4 in 10 mM NaAc pH 4; immobilized amount: 568 RU, 148 pg
   The chip surface was saturated with BSA, and the binding of oxidized proteins was investigated. For this, e.g. 50 μl of oxidized antithrombin III were injected in different concentrations at a flow rate of 20 μl/minute. The protein solutions were diluted with sample buffer. With increasing concentrations of oxidized antithrombin III the resulting signals increase. FIG. 14 shows an overlay plot of 12 sensorgrams, which show binding of oxidized antithrombin III to immobilized CD4 and subsequent dissociation.

The quantitative analysis resulted in the following values for the binding of
a) oxidized antithrombin III to HIV-GP120:
$K_{on}$ (1/Ms): $6.38 \times 10^5$
$K_{off}$ (1/s): $4.44 \times 10^4$
and a $K_D[M]$ of $7.01 \times 10^{-10}$,
b) oxidized antithrombin III to CD4:
$K_{on}$ (1/Ms): $7.13 \times 10^5$
$K_{off}$ (1/s): $1.12 \times 10^-$
and a $K_D[M]$ of $1.63 \times 10^{-9}$,
c) non-modified antithrombin III bound neither to HIV-GP120 nor to CD4. Oxidized human albumin bound with a higher affinity to HIV-GP120 and CD4 than to ox antithrombin III. Non-oxidized human albumin bound neither to HIV-GP120 nor to CD4. Oxidized protein inhibited HIV-1 infection of monocyteous cells from peripheral blood (PBMC).

PHA-activated PBMC were incubated together with negative human serum 1:100 (negative control), with neutralizing V3-loop specific antibodies (positive control), with oxidized protein (150 μg/ml) and a CCR5 tropic HIV-1 primary isolate (903) from a patient, and after 5 days the virus production was tested by P24 ELISA. For this, freshly PHA-activated PBMC were suspended in RPMI 1640 medium plus 20% FCS plus 100 U/ml IL-2 in a cell concentration of $2 \times 10^6$ cells/ml, and 200,000 cells/well/ 100 μl were distributed on a 96 well plate. Tested substances for inhibition:

Positive control: neutralizing human anti-V3-loop antibody (1:100)
Negative control: negative human serum 1:100
Experiment: oxidized protein (150 μg/ml)
was added to the cells in RPMI medium and incubated for 30 minutes at 37° C./5% $CO_2$. Subsequently, HIV-1 virus was added to the samples: each contains 10 μl/well of HIV-1 primary isolate 903 supernatant (CCR5 trop) with 20,000 TOCIDSO (50% tissue culture infective dose)/ml≈1000 $TCID_{50}$/ml per well. These samples were incubated overnight at 37° C./5% $CO_2$. The following day, the cells were washed 3 times with RPMI 1640, and new culture medium was added. On day 5 after infection, P24-ELISA tests were carried out.

P24-ELISA:
Anti-P24 antibody (11-G7 [Niedrig, Berlin] and D7320 [Biochrom]) recognize the P24 protein of the primary isolate variant 903. Maxi-Sorb-ELISA plates (Nunc) were overlayed with these antibodies overnight. The virus supernatant from the inhibition assay was inactivated by 1% Triton X-100. After washing the treated cells with PBS, the inactivated virus supernatant and alkaline phosphatase conjugated detection antibody (BC1071-AP[Aalto]) were transferred together in wells and incubated for 5 hours at 37° C. Wells were again washed with PBS, dissolved substrate for alkaline phosphatase p-nitrophenyl-phosphate (Sigma) was added to the wells, and the color development was measured after 20 minutes at 405 nm in an ELISA photometer. The parallel values in the P24-ELISA varied up to 0.02 optical density (OD) units about a common mean value. While OD 405 nm for the negative control≙no inhibition was at 0.8, the neutralizing antibody (positive control) reduced the OD to 0.12. 150 µg/ml oxidized protein reduced the OD to 0.10. The addition of oxidized proteins effectively inhibited HIV-1 infection of PBMCs.

10. Oxidized proteins induced TSP binding to cells

Oxidized proteins (for example, ox human albumin, ox antithrombin III, and ox fibrinogen, were used herein) induced specific and dose dependent binding of TSP-1 to CD36 containing cells (see FIGS. 15a-d).

Therefore, on the one hand, objects of the present invention are medicaments comprising substances that inhibit the binding of oxidized proteins to CD36 or inhibit the functions of CD36 that are induced by the interaction of CD36 with oxidized proteins.

In a preferred embodiment of the invention, the medicaments comprise antibodies that inhibit binding of oxidized proteins to CD36, comprising particularly preferred monoclonal antibodies and antibody fragments like F(ab)$_2$, F(ab), or of the antibody recognition region.

In a further preferred embodiment, the medicament comprises peptides of CD36, peptide mimetics, or peptide analogues that inhibit binding of CD36 to oxidized proteins or that inhibit cell functions of CD36 induced by interaction of CD36 with oxidized proteins. Preferably, these substances are identified and selected by monoclonal anti-CD36 antibodies disclosed in this invention, and in particular, they react with clones 37, 13, or 7, or inhibit binding of oxidized proteins/peptides to CD36, or inhibit a characteristic function of CD36, induced by oxidized protein/peptide as, but not limited to, the functions described in the examples.

In further preferred embodiment, the medicament comprises proteins or protein components that inhibit binding of CD36 to oxidized proteins or that interfere with thrombospondin bound to CD36. In a particularly preferred embodiment, such protein is soluble thrombospondin.

In a further preferred embodiment, the medicament comprises peptides or peptide mimetics that bind to CD36 and thereby inhibit the interaction of CD36 with oxidized proteins. Such peptides or peptide mimetics can be easily identified, e.g. using the so-called "phage display" procedure.

On the other hand, the object of the present invention is the use of medicaments according to the invention for prophylaxis of thrombosis, in particular in inflammatory diseases, for support of an anti-thrombotic therapy, for preventing a transplant rejection, for preventing transplantation associated arteriosclerosis, for preventing high blood pressure in kidney diseases, and in particular renin associated high blood pressure, for preventing the development and the progression of arteriosclerotic (atherosclerotic) diseases, for the treatment of chronic inflammatory reactions, for preventing early vessel reocclusion after bypass surgery, stent, PTCA, or the like, for preventing of vessel restenosis after bypass surgery, stent, PTCA, or the like, for preventing reperfusion damages, such as, but not limited to myocardial ischemia, organ transplantation, stroke, peripheral occlusive disease after surgery, and/or multi organ failure after successful reanimation, for preventing vessel damage, in particular in patients with diabetes mellitus, for preventing the inhibition of endothelial proliferation and angiogenesis induced by oxidized proteins through CD36/TSP-1, and for supporting wound healing.

Still another object of the present invention is a method for quantifying oxidized proteins (in particular ox antithrombin III, ox human albumin or ox fibrinogen), individually or together, for the evaluation of individual indications for therapies with medicaments according to the present invention, for the diagnosis of diseases, in which inflammatory reactions play a role, such as, but not limited to, arteriosclerosis, diabetic vasculopathy, rheumatic arthritis, Goodpasture Syndrome, sepsis, Colitis ulcerosa, graft-versus-host diseases, pemphigus, cancer, neurodermatitis, HIV infections, ARDS, glomerulonephritis, reperfusion damages, and for quality control of blood products.

Another object is the characterization of the activated condition of CD36, which is the receptor for oxidized proteins, as a diagnostics for diseases in which inflammatory reactions play a role such as, but not limited to, arteriosclerosis, diabetic vasculopathy, rheumatic arthritis, Goodpasture syndrome, sepsis, Colitis ulcerosa, graft-versus-host diseases, pemphigus, cancer, neurodermatitis, HIV infections, ARDS, glomerulonephritis, reperfusion damages or for monitoring a CD36/ox protein inhibition therapy with medicaments according to the present invention, by measuring the phosphorylation condition of CD36.

Still another object of the present invention is a medicament that comprises oxidized protein/oxidized proteins, oxidized peptide, oxidized structural analogues or structural mimetics thereof. Medicaments according to the present invention are also characterized in that they may contain further pharmaceutically acceptable fillers and/or excipients. The medicaments according to the present invention are preferably suitable for local, intradermal topical, intraperitoneal, intravenous, oral or intramuscular administration, or they can be applied as vesicles. Further, it is preferred that the medicaments according to the present invention further comprise substances as e.g. antibiotics, immunosuppressants, or interaction partners of oxidized proteins in the body. By the addition of such substances, the activities of the medicaments according to the present invention can be further supported and assisted.

In the context of the present invention, oxidized proteins or peptides are generated according to the present invention preferably by reaction with HOCl or peroxynitrites.

A further use of the medicaments according to the present invention, and in particular of a medicament comprising oxidized proteins/peptides or analogues or mimetics thereof, lies in the prophylaxis or therapy of acute infections, the inhibition of angiogenesis, and for the improvement of hemostasis. Thereby, the medicament is preferably used for the prophylaxis or therapy of an HIV infection. In another preferred embodiment, the use of a medicament according to the present invention comprising oxidized protein inhibits tumor angiogenesis by means of induction of TSP binding to CD36.

In still another preferred embodiment, the medicament is used for hemostasis, in particular in patients with innate or acquired blood coagulation disorders, or innate or acquired thrombocytopathia, under anticoagulation therapy or thrombosis prophylaxis, or is used in surgery under heart-lung-machine.

Figure 16A:
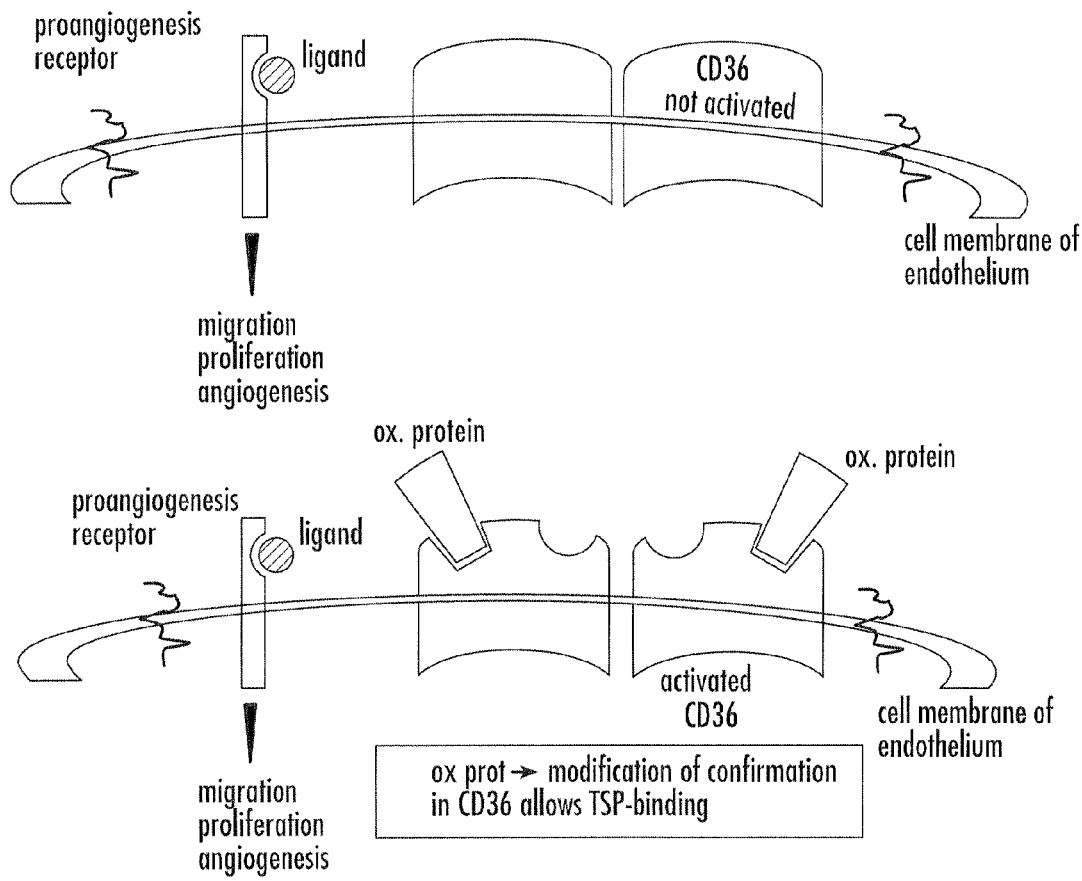
Figure 16A:
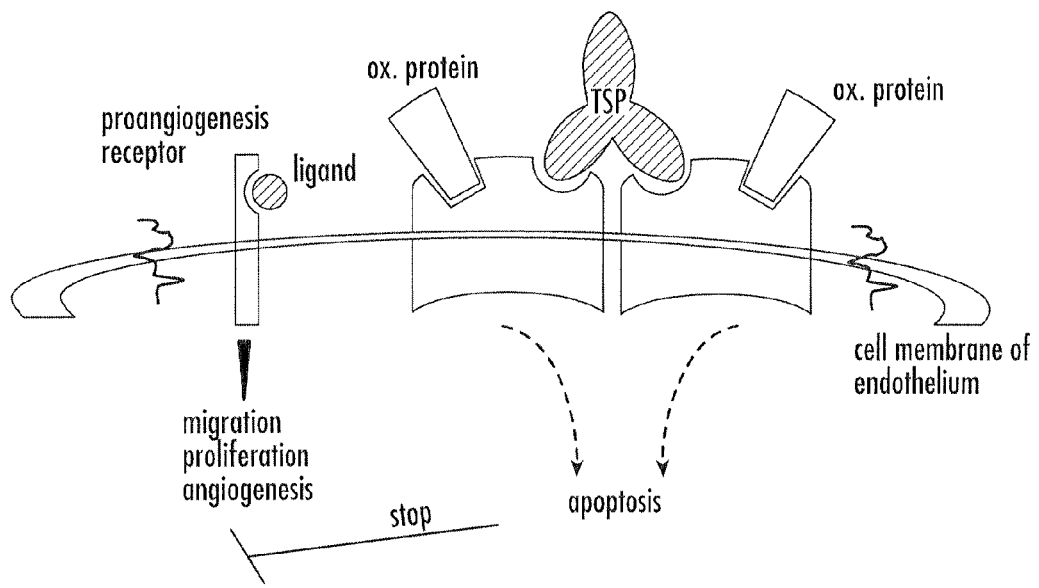

Because oxidized proteins induced TSP binding, medicaments according to claim 21 inevitably induce indirect effects of TSP bound to cell surfaces, as, e.g., inhibition of angiogenesis (see FIG. 16a) or inhibition of HIV infection. On the other hand, inhibition of the interaction between oxidized proteins and CD36 consequently induces the repression of functions that are induced by the reaction chain ox protein-CD36 cell bound TSP. Inhibitors according to claims 1-5 thereby also inhibit TSP-mediated processes, as the inhibition of angiogenesis and therefore are proangiogenetic (see FIG. 16b).

Legends of the Figures:

FIG. 1: Oxidized Proteins Bind to a CD36 Homologue Domain in HIV-1 GP120 Protein 1) Overlay-plot of 12 sensorgrams, which show the binding of oxidized antithrombin III to immobilized HIV-GP120 and the dissociation of oxidized antithrombin III. HIV-GP120 is immobilized (300 pg); the concentration of oxidized antithrombin III varied (from the bottom to the top: 0 nM; 1 nM; 5.1 nM; 10.2 nM; 17 nM; 20.4 nM; 23 nM; 34 nM; 40.8 nM; 51 nM; 85 nM; 119 nM). With an increasing concentration of oxidized AT III the resulting signal increases.

FIG. 2: Oxidized Proteins Are Hemostatic/Prothrombotic—Increase of Thrombocyte Adhesion/Inhibition of This Reaction 2a) Oxidized proteins increase platelet adhesion to collagen type I. Adhesion of thrombocytes was carried out according to Santoro et al., 1994. A 96 well cell culture plate was coated with collagen type I (25 µg/ml; 100 µl/well) overnight at 4° C., and the plates were blocked with BSA. Human thrombocytes were purified from plasma proteins by gel filtration in HEPESTyrode buffer pH 7.4 with the addition of 2 mM $Mg^{2+}$, 1 mM $Mn^{2+}$, 0.9% glucose and 0.35% BSA. 100 µl gel-filtered platelets (300000/µl) were incubated with and without oxidized proteins for 1 hour at RT in a humid chamber in the wells. Non-adhered thrombocytes were thoroughly washed away. The number of adhered platelets with determined after lysis of the platelets with Triton X-100 and determination of the lyzosomal enzyme hexosaminidase. For calibration of the adhesion assay, a calibration series with known increasing platelets number is given on a microtiter plate, and the extinction of the substrate P-nitrophenyl-N-acetyl-β-D-glucosamide is determined in relation to the number of platelets. Oxidized antithrombin III increased the thrombocyte adhesion in a dose dependent manner.

2b) Thrombocytes were used in the above-described adhesion assay and were activated with 50 µg/ml oxidized ATIII. Addition of soluble purified thrombospondin inhibited increased thrombocyte adhesion mediated by oxidized ATIII in a dose dependent manner.

2c) Thrombocytes were used in the above described adhesion assay, and were activated with oxidized ATIII. Antibodies that inhibit binding of oxidized proteins to CD36, like clones 37, 13, and 7, inhibit the activity of oxidized ATIII. All experiments for the measurement of the influence of antibodies on the thrombocyte functions were carried out in the presence of saturating, completely blocking, concentrations of Fab fragments of an antibody against the FcRIIA receptor (clone IV.3), in order to avoid Fc receptor effects.

2d) This effect is dose dependent.

2e) Inhibition of thrombocyte adhesion by soluble thrombospondin-1 is not mediated directly through its binding site on CD36 (peptide VTCG) (SEQ ID NO:4). VTCG (SEQ ID NO:4) shows no influence on the increase of thrombocyte adhesion by oxidized proteins (herein oxidized ATIII).

2f) Antibodies against CD36 that do not inhibit binding of CD36 to oxidized proteins, like clone FA6/152, however, do not induce any significant inhibition. All experiments to determine the influence of antibodies on thrombocyte functions were carried out in the presence of saturated, completely blocking, concentrations of Fab fragments of an antibody against the FcRIIA receptor (clone IV.3) in order to avoid Fc receptor effects.

Figure 3:
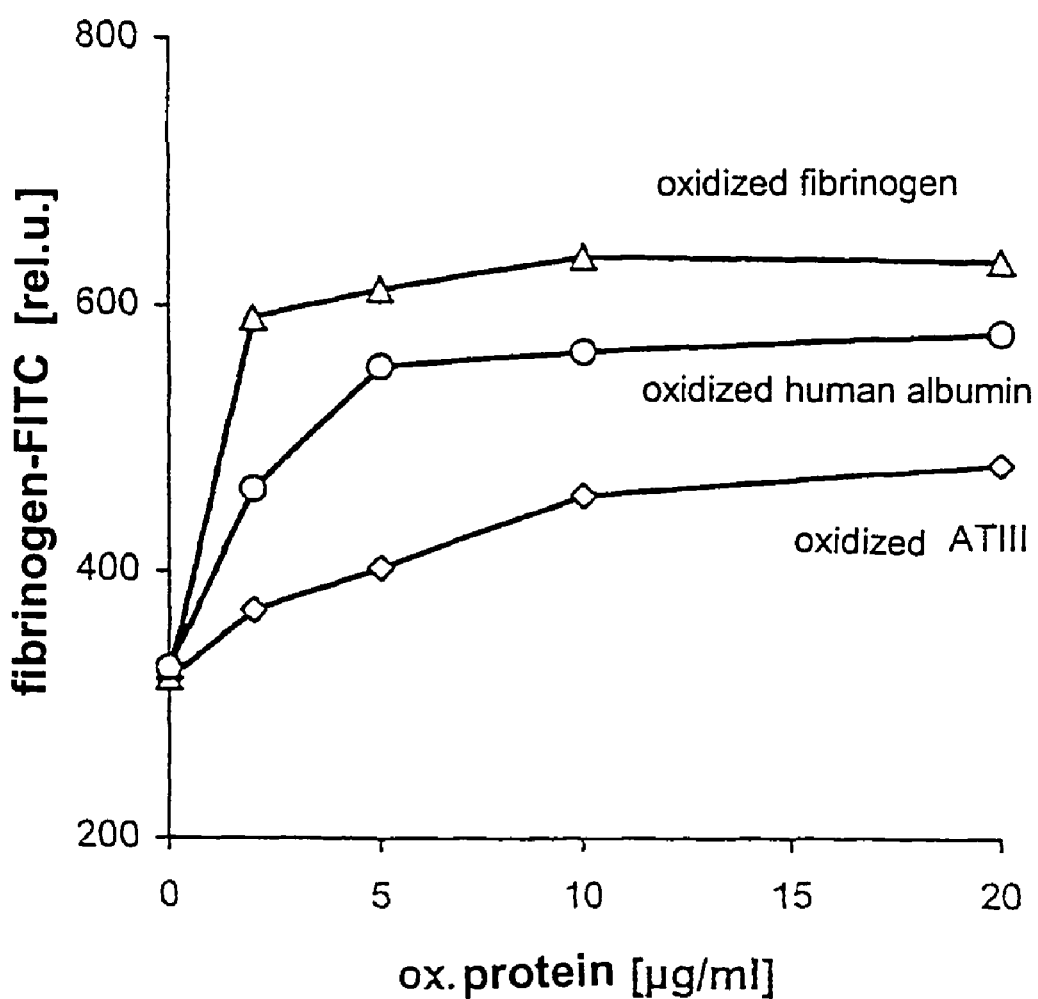

FIG. 3: Oxidized Proteins Are Hemostatic/Prothrombotic—Increase of Fibrinogen Binding to Thrombocytes/Inhibition of This Reaction FITC-conjugated fibrinogen and 10 µg/ml thrombospondin was added to gel-filtered platelets (50000/µg) in HEPES-Tyrode-BSA buffer. A portion of the sample was added with oxidized proteins in increasing concentrations. After incubation for 30 minutes at RT, the fibrinogen binding was determined in flow-through cytometry.

3a) Oxidized proteins (herein as examples, oxidized fibrinogen, oxidized human albumin, and oxidized antithrombin III) increase the fibrinogen binding to thrombocytes.

3b) Soluble thrombospondin-1 inhibits fibrinogen binding induced by ox. protein in a dose-dependent manner.

3c) Antibodies that inhibit binding of oxidized proteins to CD36, inhibit in a dose dependent manner the fibrinogen binding to thrombocytes induced by oxidized proteins.
Oxidized protein: oxidized ATIII;
antibody: anti-CD36 antibody, clone 37.

3d) Oxidized protein: oxidized fibrinogen;
antibody: anti-CD36 antibody, clone 37.

3e) Oxidized protein: oxidized human albumin
antibody: anti CD36 antibody, clone 37.

All experiments for the determination of the influence of antibodies on thrombocyte functions were carried out in the presence of saturated, completely blocking, concentrations of Fab fragments of an antibody against the FcRIIA-receptor (clone IV.3), in order to avoid Fc receptor effects.

FIG. 4: Oxidized Proteins Act Hemostatic/Prothrombotic/Induction of Thrombocyte Aggregation/Inhibition of This Reaction 4a) Oxidized proteins induce thrombocyte aggregation. Thrombocyte aggregation was carried out according to Born 1962. To gel-filtered platelets (20000/µl) in HEPES-Tyrode buffer pH 7.4 with 100 µg/ml fibrinogen, TSP-1 (25 µg/ml) was pipetted in an aggregation cuvette. Soluble TSP-1 alone did not induce aggregation. Simultaneous addition of oxidized proteins (herein oxidized fibrinogen or oxidized antithrombin III) led to a strong aggregate formation. Soluble thrombospondin inhibits in high concentrations >50 µg/ml the aggregation induced by oxidized proteins.

4b) Antibodies that inhibit binding of oxidized proteins to CD36, inhibit in a dose dependent manner the platelet aggregration induced by oxidized proteins. All experiments concerning the influence of antibodies on thrombocyte functions were carried out in the presence of saturating, completely blocking, concentrations of Fab fragments of an antibody against the FcRIIA receptor (clone IV.3) in order to avoid Fc receptor effects.

FIG. 5: Oxidized Proteins Act Hemostatic/Prothrombotic—Induction of the Pro-coagulated Condition of Thrombocytes and Microparticle Formation/Inhibition of This Reaction 5a) Oxidized proteins (herein as an example oxidized fibrinogen) induce binding of factor V/Va to thrombocytes. Factor V/Va binding was carried out as described in Dörmann et al., 1998.

5b) Oxidized proteins (herein as an example oxidized fibrinogen) induced binding of factor X/Xa to thrombocytes. Factor X/Xa binding was carried out as described by us according to Dörmann et al., 1998.

5c) Oxidized proteins (herein as an example oxidized fibrinogen) induce phospholipid flip-flop in the membrane and binding of annexin V to thrombocytes. Annexin V binding was carried out described by us according to Dörmann et al., 1998.

5d) Oxidized proteins (herein as an example oxidized fibrinogen) induce microparticle formation of thrombocytes. Gel-filtered platelets (50000/µl) were incubated with oxidized protein for 30 minutes at RT under slight agitation. Then, the platelets and microparticles resulting from platelets were incubated for 30 minutes with an anti-GPIX-PE antibody, and the number of resulting microparticles was measured in the ratio to 5000 counted particles in a flow through cytometer.

5e) Soluble thrombospondin inhibits microparticle formation induced by oxidized proteins. In this experimental example microparticle formation from thrombocytes was induced by oxidized human albumin. Gel-filtered platelets in HEPES-Tyrode buffer pH 7.4 were activated with each 50 g/ml oxidized human albumin for 1 h at RT. Before activation, the platelet suspension was added with soluble TSP in concentrations as depicted. Microparticle formation was analyzed as described in 5d). Soluble thrombospondin inhibited the formation of microparticle in a dose dependent manner.

5f) Anti-CD36 clone 37 inhibits the ox protein-induced formation of the pro-coagulated condition of the platelets. Annexin V binding as an indicator for the formation of a procoagulated membrane surface of the thrombocytes, was measured as described under 5c). Preincubation of the platelets with anti-CD36 antibodies (30 minutes, RT), which inhibits binding of oxidized proteins to CD36, inhibited the subsequent activation of these platelets by oxidized proteins (herein as an example oxidized fibrinogen). All experiments regarding the influence of antibodies on thrombocyte functions were carried out in the presence of saturating completely blocking concentrations of Fab fragments of an antibody against the FcRIIA receptor (clone IV.3) in order to avoid Fc receptor effects.

5g) Anti-CD36 clone 37 inhibits the oxidized protein induced microparticle formation of thrombocytes. Microparticle formation was determined as described under 5d). Preincubation of platelets with anti-CD36 antibodies (30 minutes, RT), which inhibit binding of oxidized proteins to CD36, before activation with oxidized proteins (herein as an example oxidized fibrinogen) inhibits microparticle formation.

Figure 6:
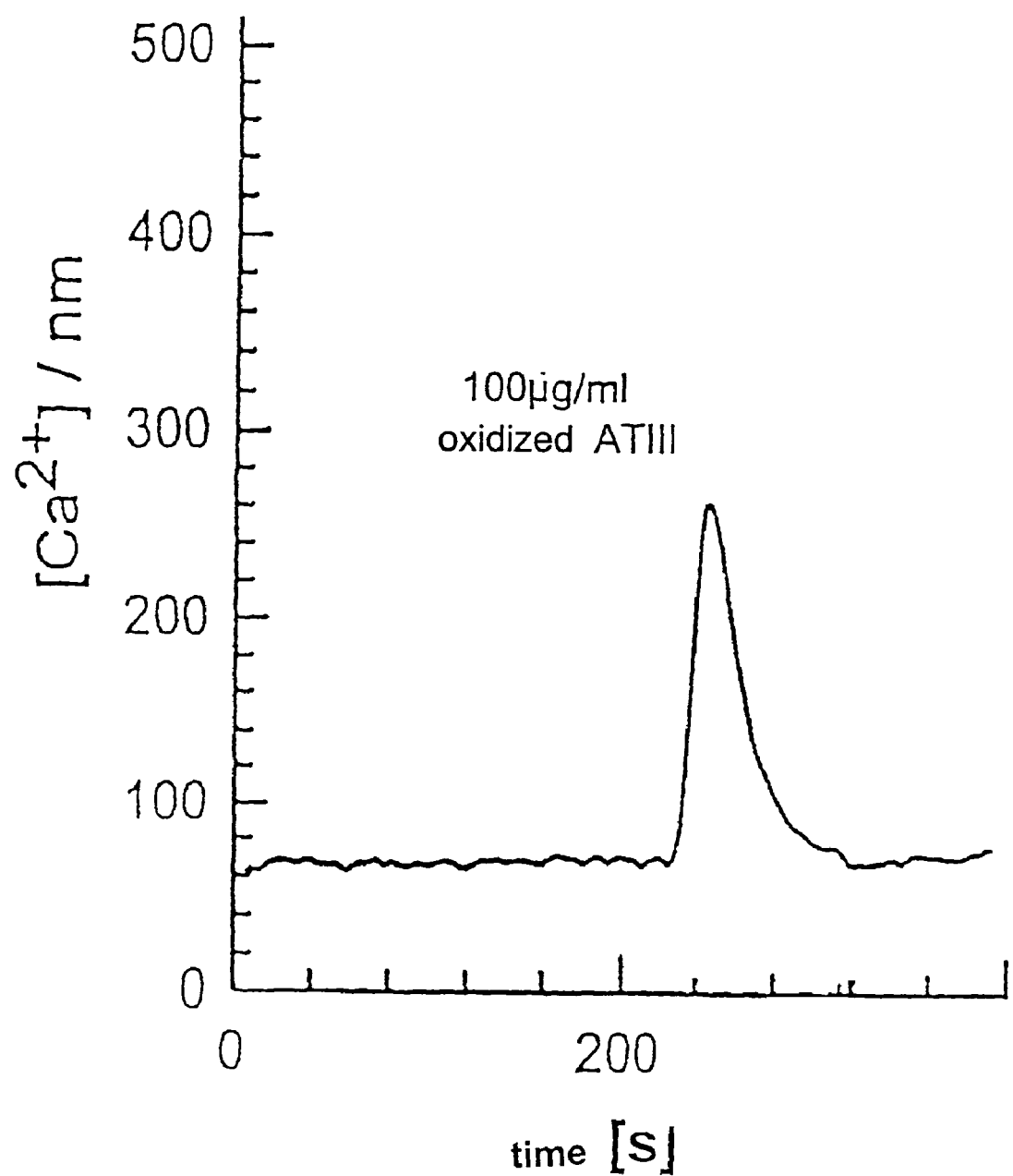

FIG. 6: Oxidized Proteins Activate Leucocytes—$Ca^{2+}$ Signal

Oxidized proteins (shown herein oxidized antithrombin III) induce a $Ca^{2+}$ signal in monocytes. The $Ca^{2+}$ measurement was carried out according to Sozzani et al., 1993. Eluted monocytes ($5\times10^6$/ml) were washed at RT with HEPES-Tyrode buffer pH 7.4 and subsequently marked for 15 minutes with 1 µM Fura2/AM at 37° C., washed twice with HEPES-Tyrode buffer without $Ca^{2+}$ and then suspended in HEPES-Tyrode with 1 mM $Ca^{2+}$. $Ca^{2+}$ signal, induced by oxidized proteins and as positive or negative control effective substances were fluorimetrically determined in Hitachi F-2000. Oxidized antithrombin III (100 µg/ml) activates monocytes and induces a clear $Ca^{2+}$ signal.

Figure 7:
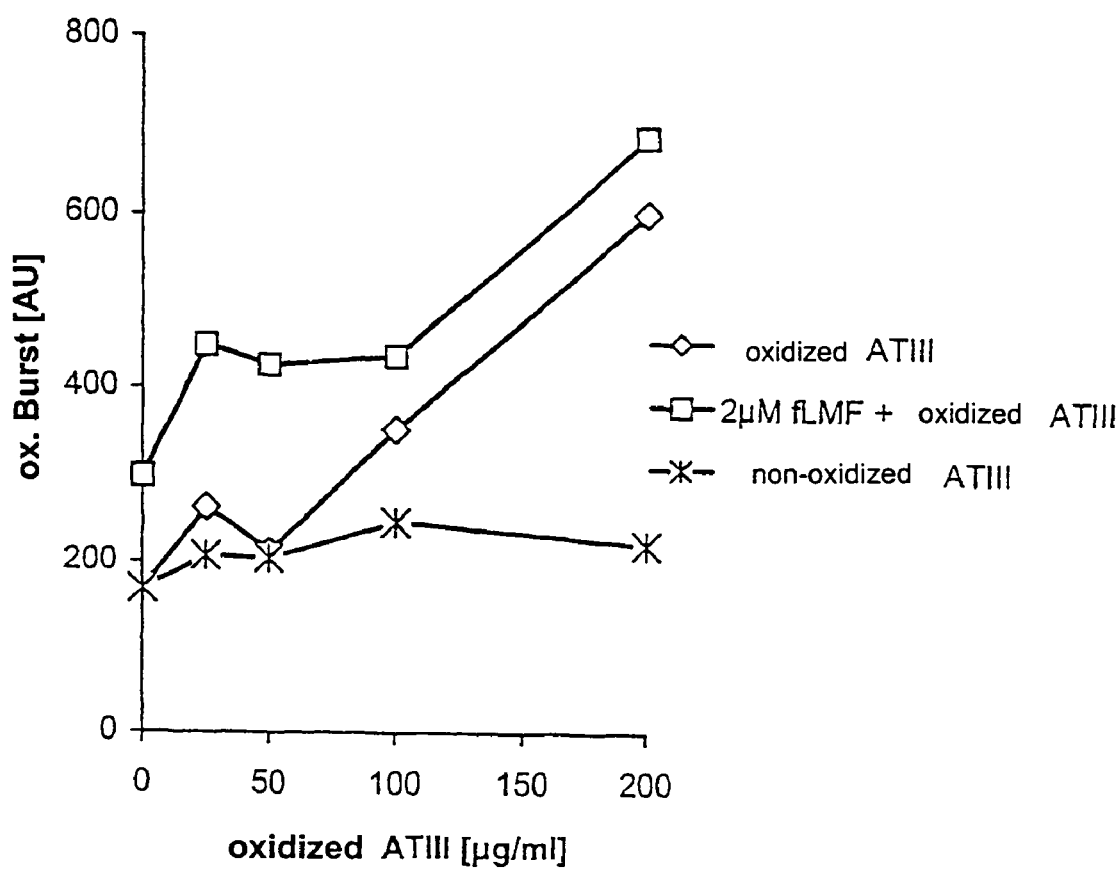

FIG. 7: Oxidized Proteins Activate Leucocytes—Oxidative Burst

Oxidized proteins increase, in a dose-dependent manner, the activating effect of fMLF on the oxidative burst of PMNL, and they even induce oxidative burst as autonomous, independent agonists. Induction of oxidative burst was essentially carried out according to the manufacturers instructions with phagotest/burst test of the company Orpegen (Heidelberg) using a flow-through cytometer. However, PMNL were first incubated with substrate DHR123 and then PMNL were activated. Oxidized antithrombin III increased the activating effect of fIMF and itself induced an ox. burst reaction.

Figure 8:
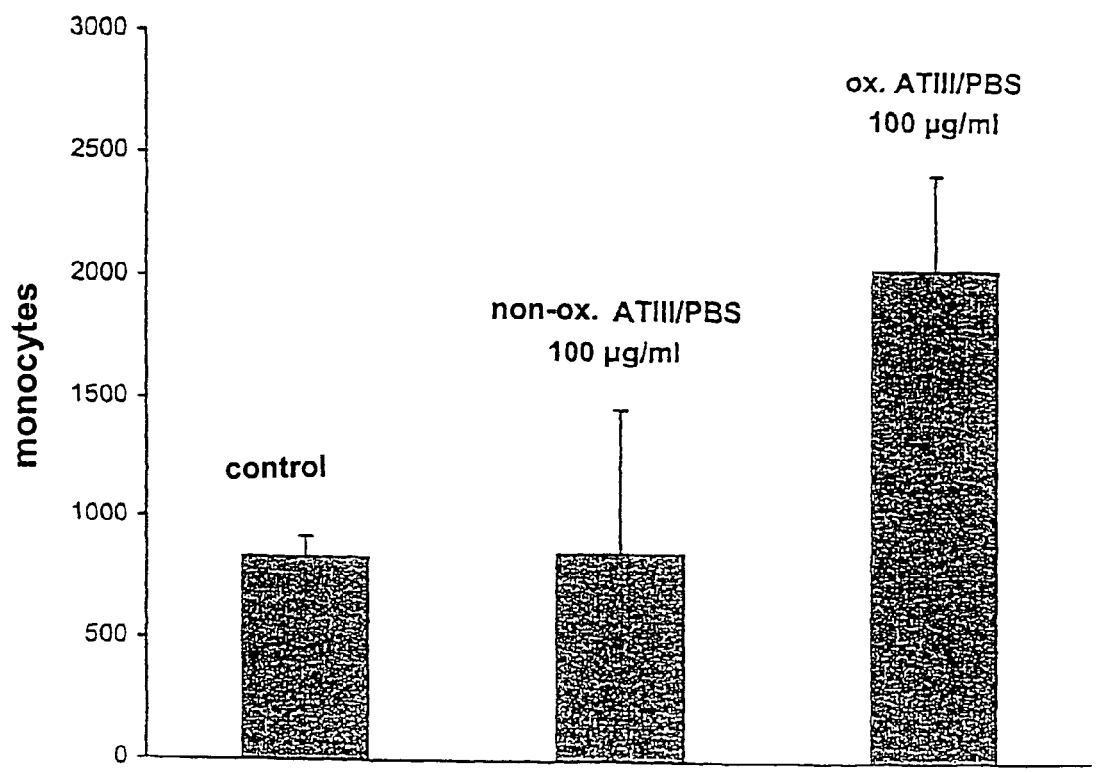
Figure 9:
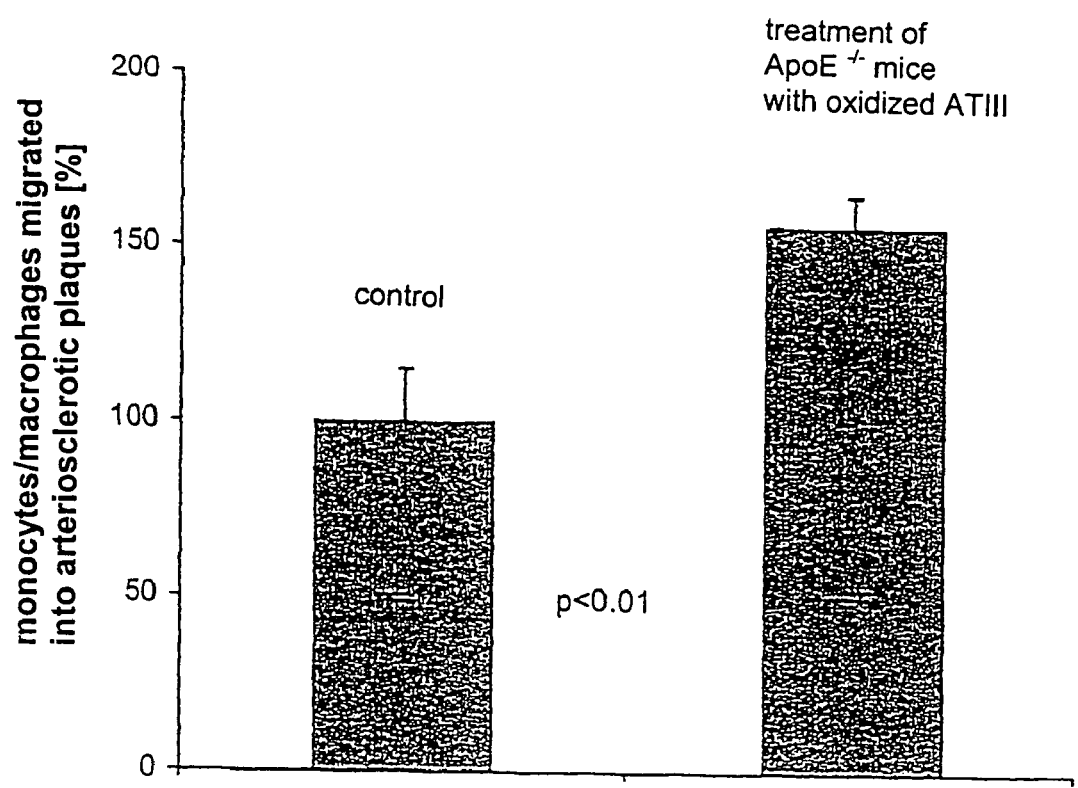

FIG. 8: Oxidized Proteins Activate Leucocytes—Transmigration Through the Endothelium/Inhibition of This Reaction 8a) In a transwell cell culture chamber (Costar, Bodenheim) a transwell insert spanned with a microporous polycarbonate membrane was placed on each of the 24 wells. The polycarbonate membrane with a pore size of 5 µm was coated with fibronectin and human microvascular endothelial cells (HMEC-1) were cultured until confluence. Human monocytes isolated by density-gradient-centrifugation (200 µl with $2\times10^7$ cells/ml in DMEM from peripheral blood) were incubated as 37° C., 7% $CO_2$ with the HMEC-1 monolayer. As a degree for the transmigration rate, the number of monocytes in the lower transwell compartment below the transwell insert was determined. In order to investigate the influence of different oxidized proteins, of thrombospondin, or of anti-CD36 antibodies, the test substances were added to the medium in the upper transwell chamber, or the endothelial cells were preincubated for 10 minutes with the test substances and washed. After 4-7 hours of transmigration time the inserts were carefully removed, the cell culture plate were placed on ice for 30 minutes to remove adhered monocytes, and the number of transmigrated monocytes was counted. Oxidized protein (herein oxidized ATIII) promotes the transmigration of monocytes through the HMEC-1 monolayer while the non-oxidized parent protein did not show this reaction (transmigration period 4 h).

8b) Preincubation of the endothelial layers for 10 minutes with TSP-1 and addition of TSP-1 to the cell culture medium during the transmigration experiment, respectively could significantly inhibit the transmigration of monocytes (transmigration period 7 h).

FIG. 9: Oxidized Proteins Induce Processes That Promote Arteriosclerosis

Oxidized antithrombin III increases homing of macrophages in arteriosclerotic plaques. The realization of the experiment was described in detail in the description of the example.

Figure 10:
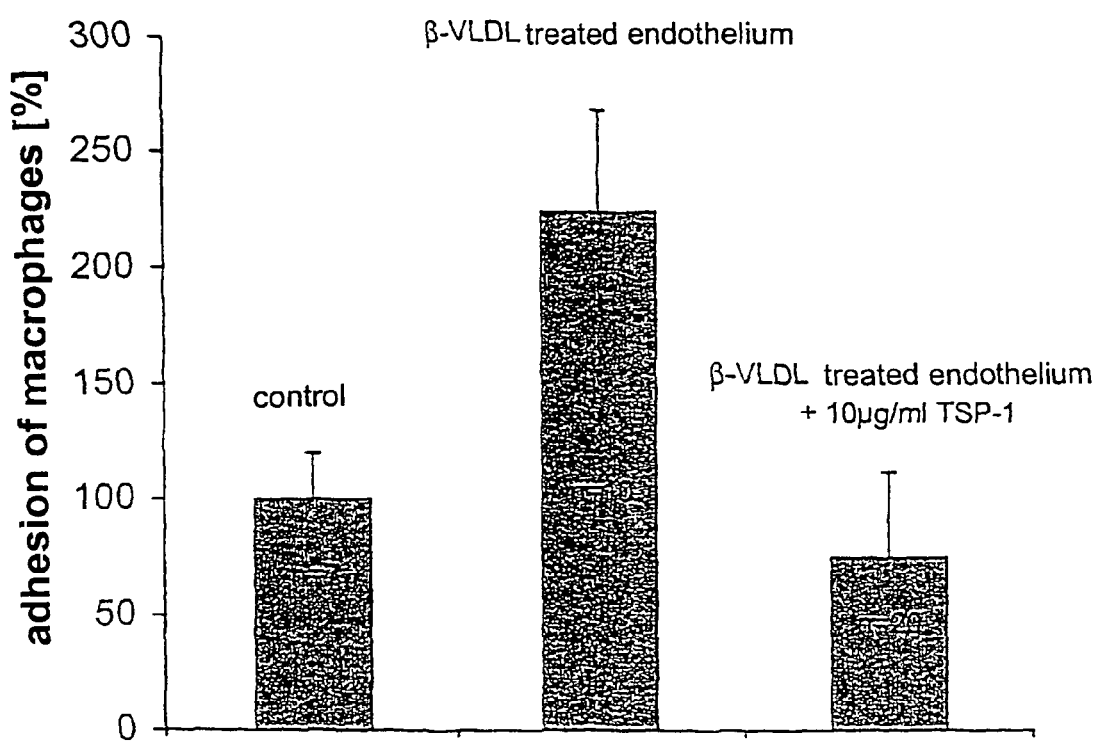

FIG. 10: Thrombospondin Inhibits Proarteriosclerotic Processes

Thrombospondin inhibits the adhesion of macrophages, to arteriosclerotically altered endothelial cells. The realization of the experiment is described in detail in the description of the example.

10a) Thrombospondin-1 inhibits the transient adhesion of macrophages, which is characterized by rolling of macrophages to arteriosclerotically altered endothelium.

10b) Thrombospondin inhibits the permanent stable adhesion of macrophages to arteriosclerotically altered endothelium.

Figure 11:
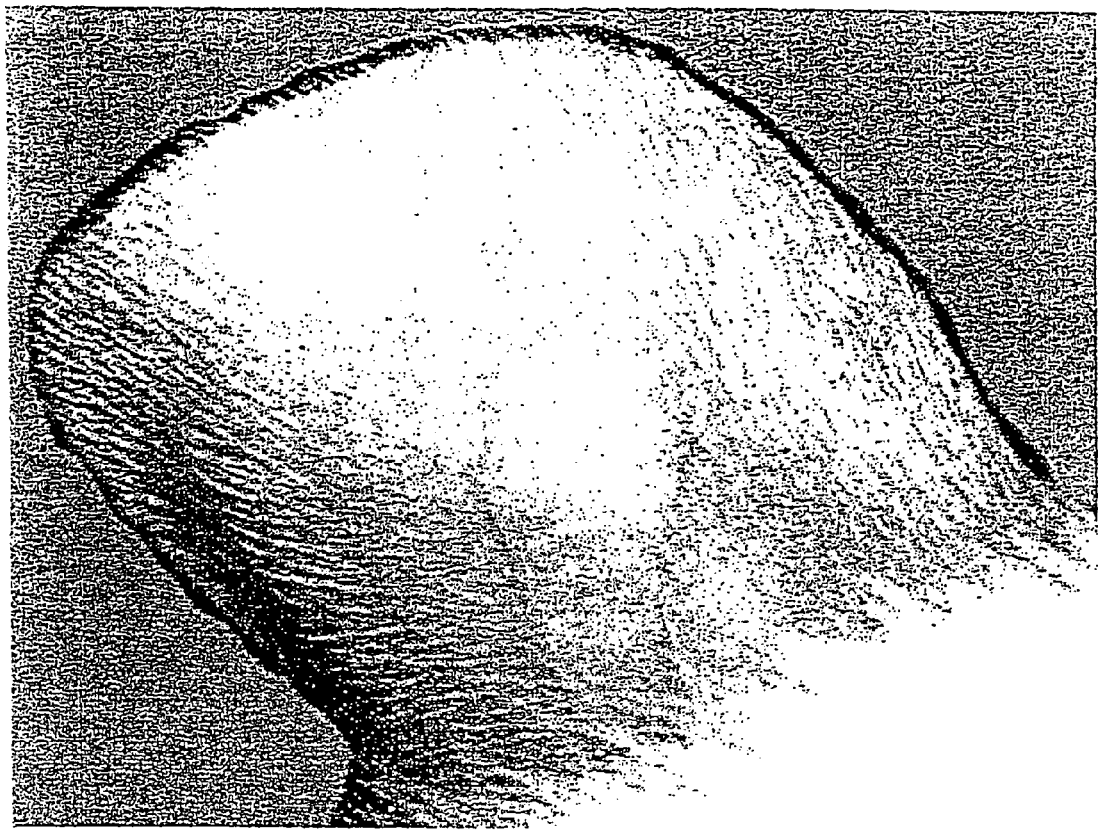

FIG. 11: Thrombospondin Inhibits Inflammatory Processes In Vivo

Soluble thrombospondin-1 inhibits the Arthus reaction in the ear of Balb/c mice.

11a) Mouse treated twice at time point 0 and 0+3 hours with each 50 µg TSP-1 i.p.—inhibits Arthus reaction in left ear.

11b) Mice treated twice at time point 0 and 0+3 hours with control buffer i.p.—Arthus reaction in left ear.

11c) Incorporated BSA-FITC in the ear as a measure for the Arthus reaction in mice treated with TSP-1 and control buffer—Arthus reaction in left ear.

FIG. 12:

Gel filtered human thrombocytes were diluted with Hepes-Tyrode buffer pH 7.4 to 50000/µl and activated at room temperature. In order to avoid Fc receptor effects on the platelets by antibodies, the experiments were carried out in the presence of completely saturating blocking concentrations of Fab fragments of an antibody against the FcRIIA receptor (clone IV.3). After activation, thrombocytes were fixed with 0.1% paraformaldehyde in HepesTyrode buffer pH 7.4 for 30 minutes and washed. Fixed, resting, and activated thrombocytes were incubated overnight anti- CD36 "AK36P" and anti-CD36 "AK36-total" in saturating concentrations overnight, respectively, and the thrombocytes were washed and incubated with a secondary, FITC-marked antibody (goat anti-rabbit IgG-FITC, "minimal X reaction with human IgG") for 1 h at RT. The thrombocytes were again washed and the binding of anti-CD36 "AK36P" and anti-CD36 "AK36-total" antibodies, respectively, were quantified by FITC fluorescence in a flow-through cytometer (FACScan-Becton Dickinson) (according to Dörmann et al., 1998).

Decrease of binding of anti-CD36 "AK36P" to thrombocytes by activation.

FIG. 13:

Blood was drained from patients with diabetes mellitus type I and control persons, and the blood was coagulated with citrate. Platelet-rich plasma (PRP) was prepared by centrifugation. PRP of patients and healthy control persons was mixed with fibrinogen (150 µg/ml) that was coupled to FITC, and the thrombocytes were activated with oxidized protein (herein oxidized human albumin) in increasing concentrations for 30 minutes. Fibrinogen binding was measured in flow-through cytometer as described above in detail. The figure shows a characteristic example of the simultaneous determination of activation with PRP of patients with diabetes mellitus type I in comparison to controls. Thrombocytes of patients with diabetes mellitus type I are particularly sensitive for the activation with oxidized proteins.

FIG. 14:

The interaction of oxidized proteins and HIV receptor CD4 was determined as described in detail in the description of the example by plasmon resonance technique in the BIA-CORE system 2000.

Overlay plot of 12 sensorgrams that show the binding of oxidized antithrombin III to immobilized CD4 and the dissociation of oxidized antithrombin III. CD4 is immobilized (148 pg); the concentration of oxidized antithrombin III was varied (from the bottom to the top: 0 nM; 1 nM; 5.1 nM; 10.2 nM; 17 nM; 20.4 nM; 23 nM; 34 nM; 40.8 nM; 51 nM; 85 nM; 119 nM). With increasing concentrations of oxidized AT III, the resulting signal increases.

FIG. 15:

15a) Oxidized protein mediates TSP-1 binding to thrombocytes

Gel-filtered human thrombocytes were diluted with Hepes-Tyrode buffer pH 7.4 to 50000/11 and FITC-conjugated purified thrombospondin-1 (50 µg/ml) was added. The thrombocytes were incubated for 1 h at RT with oxidized protein (herein oxidized fibrinogen), and TSP-1 binding to thrombocytes was measured in flow through cytometer. Oxidized proteins induce TSP-1 binding to thrombocytes.

15b) Oxidized protein (herein oxidized antithrombin III) induces binding of thrombospondin to endothelial cells.

Human microvascular endothelial cells (HMEC-1) were dissolved from the cell culture plate according to standard procedure, dissolved, and the suspension was incubated for 1 h at RT with oxidized protein and oxidized protein plus TSP-1 addition, respectively. The cells were washed and bound TSP-1 was marked with mAK anti-TSP-1 (clone P10) coupled to phycoerythrin (PE) and quantified in a flow-through cytometer. Oxidized protein induced TSP-1 binding to endothelial cells.

15c) While without the addition of purified TSP-1 and without addition of oxidized antithrombin III only approximately 1% of the eluted monocytes were detected by an antibody (clone P10), which recognizes TSP-1 on the cell surface, in flow-through cytometer, the amount increased by the addition of purified TSP-1 (10 µg/ml) to approximately 5%. The addition of oxidized AT III (without the addition of exogenous TSP-1) mediates binding of endogenous TSP-1 to monocytes. About 18% of the monocytes were TSP-1 positive. By the simultaneous addition of TSP-1 and oxidized ATIII almost all of the peripheral blood monocytes were strongly positive for TSP-1.

15d) Oxidized protein induces binding of TSP-1 to T cells. Cultured human T cells (Jurkat cells) were incubated for 1 h at RT with oxidized protein (herein oxidized antithrombin III) or oxidized protein plus TSP-1 addition (25 µg/ml). TSP-1 bound to T cells was marked by the monoclonal PE conjugated anti-TSP antibody (clone P10) and was measured in the flow-through cytometer. Oxidized proteins induced binding of endogenously present and exogenously added TSP to T cells.

FIG. 16:

This figure shows the mechanism by which medicaments as described herein inhibit or mediate functions that are induced by the reaction of thrombospondin with CD36 (example angiogenesis). The working group of N. Bouck identified thrombospondin-1 and derivatives thereof as a potent endogenous inhibitor of tumor angiogenesis, and they showed that this reaction is mediated by CD36 (Dawson et al., 1997; Jimenez et al., 2000).

16a) It has been shown by this invention that oxidized proteins mediate binding of thrombospondin to CD36. Medicaments as described herein therefore induce reactions that are mediated by this binding, as e.g. inhibition of angiogenesis, a process which can be therapeutically used for the treatment of tumors.

16b) In this invention, substances are disclosed that inhibit the interaction of oxidized proteins with CD36 and therefore processes that are induced in the body by oxidized proteins by CD36. Medicaments as described herein inhibit these reactions and prevent angiogenesis inhibition that is induced by the reaction chain oxidized proteins (CD36-conformational change-thrombospondin binding to CD36-CD36→ for angiogenesis inhibition. This reaction can be therapeutically used if angiogenesis is desired, e.g. in the heart muscle in the event of an attack.

REFERENCE LIST

1. Abumrad N, Coburn C, Ibrahimi A: Membrane proteins implicated in long-chain fatty acid uptake by mammalian cells: CD36, FATP and FABPm. Biochim. Biophys. Acta 1441: 4-13, 1999
2. Abumrad N A, el Maghrabi M R, Amri E Z, Lopez E, Grimaldi P A: Cloning of a rat adipocyte membrane protein implicated in binding or transport of long-chain fatty acids that is induced during preadipocyte differentiation. Homology with human CD36. J. Biol. Chem. 268:17665-17668,1993
3. Acton S L, Scherer P E, Lodish H F, Krieger M: Expression cloning of SR-BI, a CD36-related class B scavenger receptor. J. Biol. Chem. 269: 21003-21009,1994
4. Aiken M L, Ginsberg M H, Byers-Ward V, Plow E F: Effects of OKM5, a monoclonal antibody to glycoprotein IV, on platelet aggregation and thrombospondin surface expression [see comments]. Blood 76: 2501-2509,1990
5. Alberts G L, Pregenzer J F, Im W B: Contributions of cysteine 114 of the human D3 dopamine receptor to ligand binding and sensitivity to external oxidizing agents. Br. J. Pharmacol. 125: 705-710, 1998
6. Alessio M, Roggero S, Bussolino F, Saitta M, Malavasi F: Characterization of the murine monoclonal antibody NL07 specific for the human thrombospondin receptor (CD36 molecule). Curr. Stud. Hematol. Blood Transfus. 182-186, 1991
7. Alessio M, Greco N J, Primo L, Ghigo D, Bosia A, Tandon N N, Ockenhouse C F, Jamieson G A, Malavasi F: Platelet activation and Inhibition of malarial cytoadherence by the anti-CD36 IgM monoclonal antibody NL07. Blood 82: 3637-3647, 1993
8. Asch A S, Barnwell J, Silverstein R L, Nachman R L: Isolation of the thrombospondin membrane receptor. J. Clin. Invest 79:1054-1061, 1987
9. Asch A S, Nachman R L: Thrombospondin: phenomenology to function. Prog. Hemost. Thromb. 9:157-176, 1989
10. Asch A S, Liu 1, Briccetti F M, Bamwell J W, Kwakye-Berko F, Dokun A, Goldberger J, Pemambuco M: Analysis of CD36 binding domains: ligand specificity controled by dephosphorylation of an ectodomain. Science 262: 1436-1440, 1993
11. Babior B M: Oxygen-dependent microbial killing by phagocytes (second of two parts). N. Engl. J. Med. 298: 721-725, 1978
12. Babior B M: Oxygen-dependent microbial killing by phagocytes (first of two parts). N. Engl. J. Med. 298: 659-668, 1978
13. Bamwell J W, Asch A S, Nachman R L, Yamaya M, Aikawa M, Ingravallo P: A human 88-kD membrane glycoprotein (CD36) functions in vitro as a receptor for a cytoadherence ligand on *Plasmodium falciparum*-infected erythrocytes. J. Clin. Invest 84: 765-772, 1989
14. Baruch D I, Ma X C, Pasloske B, Howard R J, Miller L H: CD36 peptides that block cytoadherence define the CD36 binding region for *Plasmodium falciparum*-infected erythrocytes. Blood 94: 2121-2127, 1999
15. Berendt A R, Ferguson D J, Gardner J, Turner G, Rowe A, McCormick C, Roberts D, Craig A, Pinches R, Elford B C: Molecular mechanisms of Sequestration in malaria. Parasitology 108 Suppl: S19-S28,1994
16. Bosmans J L, Holvoet P, Dauwe S E, Ysebaert D K, Chapelle T, Jürgens A, Kovacic V, Van Marck E A, De Broe M E, Verpooten G A: Oxidative modification of Low-density lipoproteins and the outcome of renal allografts at 1½ years. Kidney Int. 59: 2346-2356,
17. Boullier A, Gillotte K L, Horkko S, Green S R, Friedman P, Dennis E A, Witztum J L, Steinberg D, Quehenberger O: The binding of oxidized low density lipoprotein to mouse CD36 is mediated in part by oxidized phospholipids that are associated with both the lipid and protein moieties of the lipoprotein. J. Biol. Chem. 275: 9163-9169, 2000
18. Brown Miss., Goldstein J L: A receptor-mediated pathway for cholesterol homeostasis. Science 232: 34-47, 1986
19. Calvo D, Vega M A: Identification, primary structure, and distribution of CLA-1, a novel member of the CD36/LIMPII gene family. J. Biol. Chem. 268:18929-18935, 1993
20. Carr A C, McCall M R, Frei B: Oxidation of LDL by myeloperoxidase and reactive nitrogen species: reaction pathways and antioxidant protection. Arterioscler. Thromb. Vasc. Biol. 20: 1716-1723, 2000
21. Clemetson K J: Biochemistry of platelet membrane glycoproteins. Prog. Clin. Biol. Res. 283: 33-75, 1988
22. Crombie R, Silverstein R L, MacLow C, Pearce S F A, Nachman R L, Laurence J: Identification of a CD36-related thrombospondin 1-binding domain in HIV-1 envelope glycoprotein gp120: relationship to HIV-1-specific inhibitory factors in human saliva. J. Exp. Med. 187: 25-35,1998
23. Daniel J L, Dangelmaier C, Strouse R, Smith J B: Collagen induces normal Signal transduction in platelets deficient in CD36 (platelet glycoprotein IV). Thromb. Haemost. 71: 353-356, 1994
24. Davies J M, Horwitz D A, Davies K J: Potential roles of hypochlorous acid and Nchloroamines in collagen breakdown by phagocytic cells in synovitis. Free Radic. Biol. Med. 15: 637-643, 1993
25. Dawson D W, Pearce S F, Zhong R, Silverstein R L, Frazier W A, Bouck N P: CD36 mediates the In vitro inhibitory effects of thrombospondin-1 on endothelial cells. J. Cell Biol. 138: 707-717,1997
26. Dörmann D, Kardoeus J, Zimmermann R E, Kehrel B: Flow cytometric analysis of agonist-induced annexin V, factor Va and factor Xa binding to human platelets. Platelets 9:171-177, 1998
27. Dutta-Roy A k., Crosbie L C, Gordon M J, Campbell F M: Platelet membrane glycoprotein IV (CD36) is involved in arachidonic acid induced-platelet aggregation. Biochem. Soc. Trans. 24:167S, 1996
28. Fadok V A, Warner M L, Bratton D L, Henson P M: CD36 is required for phagocytosis of apoptotic cells by human macrophages that use either a phosphatidylserine receptor or the vitronectin receptor (alpha v beta 3). J. Immunol. 161: 6250-6257, 1998
29. Fadok V A, Bratton D L, Konowal A, Freed P W, Westcott J Y, Henson P M: Macrophages that have ingested apoptotic cells in vitro inhibit proinflammatory cytokine production through autocrine/paracrine mechanisms involving TGF-beta, PGE2, and PAF. J. Clin. Invest 101: 890-898, 1998
30. Febbraio M, Abumrad N A, Hajar D P, Sharma K, Cheng W, Pearce S F, Silverstein R L: A null mutation in murine CD36 reveals an important role in fatty acid and lipoprotein metabolism. J. Biol. Chem. 274: 19055-19062,1999
31. Febbraio M, Podrez E A, Smith J D, Hajar D P, Hazen S L, Hoff H F, Sharma K, Silverstein R L: Targeted disruption of the class B scavenger receptor CD36 protects against atherosclerotic lesion development in mice [see comments]. J. Clin. Invest 105: 1049-1056, 2000
32. Frieda S, Pearce A, Wu J, Silverstein R L: Recombinant GST/CD36 fusion proteins define a thrombospondin binding domain. Evidence for a single calcium-dependent binding site on CD36. J. Biol. Chem. 270: 2981-2986,1995
33. Glaser C B, Morser J, Clarke J H, Blasko E, McLean K, Kühn 1, Chang R J, Lin J H, Vilander L, Andrews W H,.: Oxidation of a specific methionine in thrombomodulin by activated neutrophil products blocks cofactor activity. A potential rapid mechanism for modulation of coagulation. J. Clin. Invest 90: 2565-2573, 1992
34. Greenwalt D E, Watt K W, So O Y, Jiwani N: PAS IV, an integral membrane protein of mammary epithelial cells, is related to platelet and endotnelial cell CD36 (GP IV). Biochemistry 29: 7054-7059, 1990
35. Greenwalt D E, Lipsky R H, Ockenhouse C F, Ikeda H, Tandon N N, Jamieson G A: Membrane glycoprotein CD36: a review of its roles in adherence, signal transduction, and transfusion medicine. Blood 80: 1105-1115,1992
36. Hansson M, Asea A, Ersson U, Hermodsson S, Hellstrand K: Induction of apoptosis in NK cells by monocyte-derived reactive oxygen metabolites. J. Immunol. 156: 42-47, 1996
37. Hazell L J, Arnold L, Flowers D, Waeg G, Malle E, Stocker R: Presence of hypochlorite-modified proteins in human atherosclerotic lesions. J. Clin. Invest 97: 1535-1544, 1996
38. Holvoet P. Collen D: Oxidized lipoproteins in atherosclerosis and thrombosis. FASEB J. 8: 1279-1284, 1994

39. Holvoet P, Collen D: Oxidation of low density lipoproteins in the pathogenesis of atherosclerosis. Atherosclerosis 137 Suppi: S33-S38, 1998
40. Holvoet P, Stassen U M, Van Cleemput J, Collen D, Vanhaecke J: Oxidized low density lipoproteins in patients with transplant-associated coronary artery disease. Arterioscler. Thromb. Vasc. Biol. 18: 100-107,1998
41. Holvoet P, Van Cleemput J, Collen D, Vanhaecke J: Oxidized low density lipoprotein is a prognostic marker of transplant-associated eoronary artery disease. Arterioscler. Thromb. Vasc. Biol. 20: 698-702, 2000
42. Holvoet P, Mertens A, Verhamme P, Bogaerts K, Beyens G, Verhaeghe R, Collen D, Muls E, Van de W F: Circulating oxidized LDL is a useful marker for identifying patients with coronary artery disease. Arterioscler. Thromb. Vasc. Biol. 21: 844-848, 2001
43. Huang M M, Bolen J B, Barnwell. J W, Shattil S J, Brügge J S: Membrane glycoprotein IV (CD36) is physically associated with the Fyn, Lyn, and Yes protein-tyrosine kinases in human platelets. Proc. Natl. Acad. Sci. U.S.A 88: 7844-7848, 1991
44. Jimenez B, Volpert O V, Crawford S E, Febbraio M, Silverstein R L, Bouck N: Signals leading to apoptosis-dependent Inhibition of neovascularization by thrombospondin-1. Nat. Med. 6: 4148, 2000
45. Kehrel B, Kronenberg A, Schwippert B, Niesing-Bresch D, Niehues U, Tschope D, van de L J, Clemetson K J: Thrombospondin binds normally to glycoprotein IIIb deficient platelets. Biochem. Biophys. Res. Commun. 179: 985-991,1991
46. Kehrel B, Kronenberg A, Rauterberg J, Niesing-Bresch D, Niehues U, Kardoeus J, Schwippert B, Tschope D, van de L J, Clemetson K J: Platelets deficient in glycoprotein IIIb aggregate normally to collagens type 1 and III but not to Collagen type V. Blood 82: 3364-3370,1993
47. Kehrel B: Platelet-collagen interactions. Semin. Thromb. Hemost. 21: 123-129,1995
48. Kieffer N, Bettaieb A, Legrand C, Coulombel L, Vainchenker W, Edelman L, Breton-Gorius J: Developmentally regulated expression of a 78 kDa erythroblast membrane glycoprotein immunologically related to the platelet thrombospondin receptor. Biochem. J. 262: 835-842,1989
49. Kielbassa K, Schmitz C, Gerke V: Disruption of endothelial microfilaments selectively reduces the transendothelial migration of monocytes. Exp. Cell Res. 243: 129-141, 1998
50. Knowles D M, Tolidjian B, Marboe C, D'Agati V, Grimes M, Chess L: Monoclonal antihuman monocyte antibodies OKM1 and OKM5 possess distinctive tissue distributions including differential reactivity with vascular endothelium. J. Immunol. 132: 2170-2173,
51. Kronenberg A, Grahl H, Kehrel B: Human platelet CD36 (GPIIIb, GPIV) binds to cholesteryl-hemisuccinate and can be purified by a simple two-step method making use of this property. Thromb. Haemost. 79: 1021-1024, 1998
52. Leung L L, Li W X, McGregor J L, Albrecht G, Howard R J: CD36 peptides enhance or inhibit CD36-thrombospondin binding. A two-step process of ligand-receptor interaction. J. Biol. Chem. 267:18244-18250,1992
53. Li W X, Howard R J, Leung L L: Identification of SVTCG in thrombospondin äs the conformation-dependent, high affinity binding site for its receptor, CD36. J. Biol. Chem. 268: 16179-16184, 1993
54. Lian EC, Siddiqui F A, Jamieson G A, Tandon N N: Platelet agglutinating protein p37 causes platelet agglutination through its binding to membrane glycoprotein IV. Thromb. Haemost. 65: 102-106, 1991
55. McGregor J L, Clemetson K J, James E, Luscher E F, Dechavannne M: Characterization of human blood platelet membrane proteins and glycorproteins by their isoelectric point (pl) and apparent molecular weight using two-dimensional electrophoresis and surface-labelling techniques. Biochiin. Biophys. Acta 599: 473483, 1980
56. McGregor J L, Clemetson K J, James E, Capitanio A, Greenland T, Luscher E F, Dechavanne M: Glycoproteins of platelet membranes from Glanzmanr's thrombasthenia. A comparison with normal using carbohydrate-specific or protein-specific labelling techniques and high-resolution two-dimensional gel electrophoresis. Eur. J. Biochem. 116: 379-388,1981
57. Nakata A, Nakagawa Y, Nishida M, Nozaki S, Miyagawa J, Nakagawa T, Tamura R, Matsumoto K, Kameda-Takemura K, Yamashita S, Matsuzawa Y: CD36, a novel receptor for oxidized low-density lipoproteins, is highly expressed on lipid-laden macrophages in human atherosclerotic aorta. Arterioscler. Thromb. Vasc. Biol. 19:1333-1339, 1999
58. Nguyen-Khoa T, Massy Z A, Witko-Sarsat V, Canteloup S, Kebede M, Lacour B, Drueke T, Descamps-Latscha B: Oxidized low-density lipoprotein induces macrophage respiratory burst via its protein moiety: A novel pathway in atherogenesis" Biochem. Biophys. Res. Commun. 263: 804-809,1999
59. Nicholson A C, Frieda S, Pearce A, Silverstein R L: Oxidized LDL binds to CD36 on human monocyte-derived macrophages and transfected cell lines. Evidence implicating the lipid moiety of the lipoprotein as the binding site. Arterioscler. Thromb. Vasc. Biol. 15: 269-275, 1995
60. Nozaki S, Kashiwagi H, Yamashita S, Nakagawa T, Kostner B, Tomiyama Y, Nakata A, Ishigami M, Miyagawa J, Kameda-Takemura K: Reduced uptake of oxidized low density lipoproteins in monocyte-derived macrophages from CD36-deficient subjects. J. Clin. Invest 96: 1859-1865,1995
61. Nozaki S, Tanaka T, Yamashita S, Sobmiya K, Yoshizumi T, Okamoto F, Kitaura Y, Kotake C, Nishida H, Nakata A, Nakagawa T, Matsumoto K, Kameda-Takemura K, Tadokoro S, Kurata Y, Tomiyama Y, Kawamura K, Matsuzawa Y: CD36 mediates long-chain fatty acid transport in human myocardium: complete myocardial accumulation defect of radiolabeled long-chain fatty acid analog in subjects with CD36 deficiency. Mol. Cell Biochem. 192:129-135, 1999
62. Ockenhouse C F, Tandon N N, Magowan C, Jamieson G A, Chulay J D: Identification of a platelet membrane glycoprotein as a falciparum malaria sequestration receptor [see comments]. Science 243: 1469-1471,1989
63. Oquendo P, Hundt E, Lawler J, Seed B: CD36 directly mediates cytoadherence of *Plasmodium falciparum* parasitized erythrocytes. Cell 58: 95-101, 1989
64. Patel S S, Thiagarajan R, Willerson J T, Yeh E T: Inhibition of alpha4 integrin and ICAM-1 markedly attenuate macrophage homing to atherosclerotic plaques in ApoE-deficient mice. Circulation 97: 75-81, 1998
65. Pearce S F, Roy P, Nicholson AC, Hajjar D P, Febbraio M, Silverstein R L: Recombinant glutathione S-transferase/CD36 fusion proteins define an oxidized low density lipoprotein-binding domain. J. Biol. Chem. 273: 34875-34881, 1998
66. Podrez E A, Febbraio M, Sheibani N, Schmitt D, Silverstein R L, Hajjar D P, Cohen P A, Frazier W A, Hoff H F, Hazen S L: Macrophage scavenger receptor CD36 is the major receptor for LDL modified by monocyte-generated reactive nitrogen species [see comments] [published erratum appears in J Clin Invest 2000 May;105(10):1483]. J. Clin. Invest 105: 1095-1108, 2000
67. Puente N, Daviet L, Ninio E, McGregor J L: Identification on human CD36 of a domain (155-183) implicated in binding oxidized low-density lipoproteins (Ox-LDL). Arterioscler. Thromb. Vasc. Biol. 16:1033-1039,1996
68. Ricciarelli R, Zingg J M, Azzi A: Vitamin E reduces the uptake of oxidized LDL by inhibiting CD36 scavenger receptor expression in cultured aortic smooth muscle cells. Circulation 102: 82-87, 2000
69. Rigotti A, Acton S L, Krieger M: The class B scavenger receptors SR-B1 and CD36 are receptors for anionic phospholipids. J. Biol. Chem. 270:16221-16224,1995
70. Roberts D D, Sherwood J A, Spitalnik S L, Panton U, Howard R J, Dixit V M, Frazier W A, Miller L H, Ginsburg V: Thrombospondin binds falciparum malaria parasitized erythrocytes and may mediate cytoadherence. Nature 318: 64-66, 1985
71. Ryeom S W, Sparrow J R, Silverstein R L: CD36 participates in the phagocytosis of rod outer segments by retinal pigment epithelium. J. Cell Sci. 109 (R 2): 0.387-395, 1996
72. Saelman E U, Kehre! B, Hese K M, de Groot P G, Sixma J J, Nieuwenhuis H K: Platelet adhesion to collagen and endothelial cell matrix under flow conditions is not dependent on platelet glycoprotein IV. Blood 83: 3240-3244, 1994
73. Samanta A, Das D K, Jones R, George A, Prasad M R: Free radical scavenging by myocardial fatty acid binding protein. Free Radic. Res. Commun. 7: 73-82, 1989
74. Schraufstatter I U, Browne K, Harris A, Hyslop P A, Jackson J H, Quehenberger O, Cochrane C G: Mechanisms of hypochlorite injury of target cells. J. Clin. Invest 85: 554-562,1990
75. Schuepp B J, Pfister H, Clemetson K J, Silverstein R L, Jungi T W: CD36-mediated signal transduction in human monocytes by anti-CD36 antibodies but not by anti-thrombospondin antibodies recognizing cell membrane-bound thrombospondin. Biochem. Biophys. Res. Commun. 175: 263-270,1991
76. Shah M M, Aust S D: Oxidation of halides by peroxidases and their subsequent reductions: Arch. Biochem. Biophys. 300: 253-257, 1993
77. Shattil S J, Brügge J S: Protein tyrosine phosphorylation and the adhesive functions of platelets. Curr. Opin. Cell Biol. 3: 869-879,1991
78. Silverstein R L, Baird M, Lo S K, Yesner L M: Sense and antisense cDNA transfection of CD36 (glycoprotein IV) in melanoma cells. Role of CD36 as a thrombospondin receptor. J. Biol. Chem. 267:16607-16612,1992
79. Smith M A, Rottkamp C A, Nunomura A, Raina A K, Perry G: Oxidative stress in Alzheimer's disease. Biochim. Biophys. Acta 1502: 139-144, 2000
80. Stadtman E R: Protein oxidation and aging. Science 257: 1220-1224, 1992
81. Steinberg D: Low density lipoprotein oxidation and its pathobiological significance. J. Biol. Chem. 272: 20963-20966, 1997
82. Tandon N N, Kralisz U, Jamieson G A: Identification of glycoprotein IV (CD36) äs a primary receptor for platelet-collagen adhesion. J. Biol. Chem. 264: 7576-7583, 1989
83. Tandon N N, Ockenhouse C F, Greco N J, Jamieson G A: Adhesive functions of platelets lacking glycoprotein IV (CD36). Blood 78: 2809-2813, 1991
84. Vega M A, Segui-Real B, Garcia J A, Cales C, Rodriguez F, Vanderkerckhove J, Sandoval IV:.Cloning, sequencing, and expression of a cDNA encoding rat LIMP II, a novel 74-kDa lysosomal membrane protein related to the surface adhesion protein CD36. J. Biol. Chem. 266: 16818-16824, 1991
85. Volf 1, Bielek E, Moeslinger T, Koller F, Koller E: Modification of protein moiety of human low density lipoprotein by hypochlorite generates strong platelet agonist. Arterioscler. Thromb. Vasc. Biol. 20: 2011-2018, 2000
86. Weiss S J: Tissue destruction by neutrophils. N. Engl. J. Med. 320: 365-376,1989
87. Witztum J L, Steinberg D: Role of oxidized low density lipoprotein in atherogenesis. J. Clin. Invest 88: 1785-1792, 1991
88. Yamaguchi A, Yamamoto N, Akamatsu N, Saldo T C, Kaneda M, Umeda M, Tanoue K: PS-liposome and ox-LDL bind to different sites of the immunodominant domain (#155-183) of CD36: a study with GS95, a new anti-CD36 monoclonal antibody. Thromb. Res. 97: 317-326,2000

What is claimed is:

1. A method for therapy of HIV infections, inhibition of angiogenesis, or improvement of hemostasis, said method comprising administering to an animal or human in need thereof an effective amount of a medicament comprising an oxidized protein wherein the oxidation is carried out with hypochloric acid (HOCl).

2. The method of claim 1, wherein said angiogenesis is a tumor angiogenesis, and wherein said angiogenesis is inhibited by said oxidized protein inducing TSP binding to CD36.

3. The method of claim 1, wherein said hemostasis is improved in a human or animal having an innate or acquired blood coagulation disorder, or an innate or acquired thrombocytopathia, or is undergoing anticoagulation therapy, thrombosis prophylaxis, or surgery under a heart-lung-machine.

4. The method of claim 1, wherein the medicament further comprises a pharmaceutically acceptable filler or excipient.

5. The method of claim 1 wherein the medicament is formulated for local, intradermal, topical, intraperitoneal, intravenous, oral, or intramuscular administration, or formulated as vesicles.

6. The method of claim 1, wherein the medicament further comprises immunosuppressants or interaction partners of oxidized proteins in the body.

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial
<220> FEATURE:
<223> OTHER INFORMATION: Chemically synthesized.

<400> SEQUENCE: 1

Lys Gln Arg Gly Pro Tyr Thr Tyr Arg Val Arg Phe Leu Ala Lys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Chemically synthesized.
```

```
-continued

<220> FEATURE:
<221> NAME/KEY: MOD_RES
<222> LOCATION: (7)..(7)
<223> OTHER INFORMATION: PHOSPHORYLATION

<400> SEQUENCE: 2

Lys Gln Arg Gly Pro Tyr Thr Tyr Arg Val Arg Phe Leu Ala Lys
1               5                   10                  15

<210> SEQ ID NO 3
<211> LENGTH: 5
<212> TYPE: PRT
<213> ORGANISM: ARTIFICIAL
<220> FEATURE:
<223> OTHER INFORMATION: Sequence of thrombospondin that binds to CD36
      with high affinity.

<400> SEQUENCE: 3

Ser Val Thr Cys Gly
1               5

<210> SEQ ID NO 4
<211> LENGTH: 4
<212> TYPE: PRT
<213> ORGANISM: artificial
<220> FEATURE:
<223> OTHER INFORMATION: Thrombospondin binding site on CD36.

<400> SEQUENCE: 4

Val Thr Cys Gly
1
```